US007419806B2

(12) United States Patent
Minion et al.

(10) Patent No.: US 7,419,806 B2
(45) Date of Patent: Sep. 2, 2008

(54) IMMUNOGENIC *MYCOPLASMA HYOPNEUMONIAE* POLYPEPTIDES

(75) Inventors: F. Chris Minion, Ames, IA (US); Steven P. Djordjevic, Emu Heights (AU)

(73) Assignee: Iowa State University Research Foundation, Inc., Ames, IA (US)

( * ) Notice: Subject to any disclaimer, the term of this patent is extended or adjusted under 35 U.S.C. 154(b) by 131 days.

(21) Appl. No.: 10/607,631

(22) Filed: Jun. 27, 2003

(65) Prior Publication Data

US 2004/0091901 A1 May 13, 2004

Related U.S. Application Data

(60) Provisional application No. 60/392,632, filed on Jun. 28, 2002.

(51) Int. Cl.
*C12P 21/04* (2006.01)
*G01N 33/53* (2006.01)
*C07H 21/04* (2006.01)
*A61K 39/02* (2006.01)

(52) U.S. Cl. ......................... 435/69.7; 435/69.5; 435/6; 435/7.2; 435/810; 530/350; 538/23.7; 538/23.5; 424/264.1

(58) Field of Classification Search .............. 424/264.1, 424/185.1, 192.1; 435/69.5, 69.7, 6, 7.2, 435/810; 536/23.5, 23.7; 514/2, 12; 530/350
See application file for complete search history.

(56) References Cited

U.S. PATENT DOCUMENTS

| | | | |
|---|---|---|---|
| 4,894,332 | A | 1/1990 | Schaller et al. |
| 5,459,048 | A | 10/1995 | Kuner et al. |
| 5,580,859 | A | 12/1996 | Felgner et al. |
| 5,589,466 | A | 12/1996 | Felgner et al. |
| 5,703,055 | A | 12/1997 | Felgner et al. |
| 5,836,905 | A | 11/1998 | Lemelson et al. |
| 6,162,435 | A | 12/2000 | Minion et al. |
| 2002/0068289 | A1 | 6/2002 | Moore et al. |

FOREIGN PATENT DOCUMENTS

| | | |
|---|---|---|
| WO | WO 00/31115 | 6/2000 |

OTHER PUBLICATIONS

Uniprot_03, Accession No. Q9KGX7 or. Q9KGX9.*
Zhang et al Infect. Immun., Mar. 1995, 1013-1019, vol. 63, No. 3.*
Giron et al Infect. Immun., Jan. 1996, p. 197-208 vol. 64, No. 1.*
Burgess et al., The Journal of Cell Biology, 111:2129-2138, 1990.*
Roitt et al (Immunology, 1993, Mosby, St. Louis, p. 7.7-7.8).*
Holmes (Exp. Opin.Invest. Drugs, 2001, 10(3):511-519).*
Rudinger et al, in "Peptide Hormones", edited by Parsons, J.A., University Park Press, Jun. 1976.*
Bowie et al (Science, 1990, 257:1306-1310).*
Herbert et al (The Dictionary of Immunology, Academic Press, 3rd Edition, London, 1985, pp. 58-59).*
Greenspan et al (Nature Biotechnology, 1999, 7:936-937.*
Coleman et al. (Research in Immunology, 1994; 145(1): 33-36).*
Abaza et al. (Journal of Protein Chemistry, vol. 11, No. 5, 1992, pp. 433-444.*
Bordier, "Phase Separation of Integral Membrane Proteins in Triton X-114 Solution," *J. Biol. Chem.*, 1981, 256:1604-1607.
Cordwell et al., "Characterization of basic proteins from *Spiroplasma melliferum* using novel immobilised pH gradients," *Electrophoresis*, 1997, 18:1393-1398.
Djordjevic et al., "Serum and mucosal antibody responses and protection in pigs vaccinated against *Mycoplasma hyopneumoniae* with vaccines containing a denatured membrane antigen pool and adjuvant," *Aust. Vet. J.*, 1997, 75:504-511.
Djordjevic et al., "An improved enzyme linked immunosorbent assay (ELISA) for the detection of porcine serum antibodies against *Mycoplasma hyopneumoniae," Vet. Microbiol.*, 1994, 39:261-274.
Dybvig and Yu, "Regulation of a restriction and modification system via DNA inversion in *Mycoplasma pulmonis," Mol. Microbiol.*, 1994, 12:547-560.
Friis, "Mycoplasmas Cultivated from the Respiratory Tract of Danish Pigs," *Acta Vet. Scand.*, 1971, 12:69-79.
Glew et al., "pMGA Phenotypic Variation in *Mycoplasma gallisepticum* Occurs In Vivo and Is Mediated by Trinucleotide Repeat Length Variation," *Infect. Immun.*, 2000, 68:6027-6033.
Gobom et al., "Sample Purification and Preparation Technique Based on Nano-scale Reversed-phase Columns for the Sensitive Analysis of Complex Peptide Mixtures by Matrix-assisted Laser Desorption/ Ionization Mass Spectrometry," *J. Mass Spectrom.*, 1999, 34:105-116.
Guerreiro et al., "New *Rhizobium leguminosarum* Flavonoid-Induced Proteins Revealed by Proteome Analysis of Differentially Displayed Proteins," *Mol. Plant Microbe Interact.*, 1997, 10:506-516.
Hsu and Minion, "Molecular analysis of the p97 cilium adhesin operon of *Mycoplasma hyopneumoniae," Gene*, 1998, 214:13-23.
Hsu and Minion, "Identification of the Cilium Binding Epitope of the *Mycoplasma hyopneumoniae* P97 Adhesin," *Infect. Immun.*, 1998, 66:4762-4766.
Hsu et al., "Cloning and Functional Analysis of the P97 Swine Cilium Adhesin Gene of *Mycoplasma hyopneumoniae," J. Bacteriol.*, 1997, 179:1317-1323.

(Continued)

*Primary Examiner*—Shanon A. Foley
*Assistant Examiner*—Padma v Baskar
(74) *Attorney, Agent, or Firm*—Fish & Ricahrdson P.C.

(57) ABSTRACT

*Mycoplasma hyopneumoniae* polypeptides and nucleic acids, as well as nucleic acid expression vectors and host cells containing nucleic acid vectors are provided. In addition, compositions containing *M. hyopneumoniae* polypeptides and nucleic acids are provided for use in methods of treating swine to prevent enzootic pneumonia. Furthermore, the invention provides diagnostic tests for the detecting of *M. hyopneumoniae* infection in swine herds.

13 Claims, 23 Drawing Sheets

OTHER PUBLICATIONS

Kim et al., "Identification and Mapping of an Immunogenic Region of *Mycoplasma hyopneumoniae* p65 Surface Lipoprotein Expressed in *Escherichia coli* from a cloned Genomic Fragment," *Infect. Immun.*, 1990, 58:2637-2643.

Laemmli, "Cleavage of Structural Proteins during the Assembly of the Head of Bacteriophage T4," *Nature*, 1970, 227:680-685.

Liu et al., "GAA Trinucleotide Repeat Region Regulates M9/pMGA Gene Expression in *Mycoplasma gallisepticum," Infect. Immun.*, 2000, 68:871-876.

Luo and Lin, "Generation of Moderate Amounts of Polyclonal Antibodies in Mice," *BioTechniques*, 1997, 23:630, 632.

Lysnyansky et al., "Phenotypic Switching of Variable Surface Lipoproteins in *Mycoplasma bovis* Involves High-Frequency Chromosomal Rearrangements," *J. Bacteriol.*, 1996, 178:5395-5401.

Meier et al., "Immunodetection of Biotinylated Lymphocyte-Surface Proteins by Enhanced Chemiluminescence: A Nonradioactive Method for Cell Surface Protein Analysis," *Anal. Biochem.*, 1992, 204:220-226.

Minion et al., "R1 Region of P97 Mediates Adherence of *Mycoplasma hyopneumoniae* to Swine Cilia," *Infect. Immun.*, 2000, 68:3056-3060.

Noormohammadi et al., "A novel mechanism for control of antigenic variation in the haemagglutinin gene family of *Mycoplasma synoviae," Mol. Microbiol.*, 2000, 35:911-923.

Nouwens et al., "Complementing genomics with proteomics: The membrane subproteome of *Pseudomonas aeruginosa* PAO1," *Electrophoresis*, 2000, 21:3797-3809.

Probert et al., "Mapping the Ligand-Binding Region of *Borrelia burgdorferi* Fibronectin-Binding Protein BBK32," *Infect. Immun.*, 2001, 69:4129-4133.

Rabilloud et al., "Modified silver staining for immobilized pH gradients," *Electrophoresis*, 1992, 13:264-266.

Rocha et al., "Identification and Characterization of a Novel Fibronectin-Binding Protein on the Surface of Group A Streptococci," *Infect. Immun.*, 1999, 67:2720-2728.

Rosengarten and Wise, "Phenotypic Switching in Mycoplasmas: Phase Variation of Diverse Surface Lipoproteins," *Science*, 1990, 247:315-318.

Sachse et al., "Epitope Mapping of Immunogenic and Adhesive Structures in Repetitive Domains of *Mycoplasma bovis* Variable Surface Lipoproteins," *Infect. Immun.*, 2000, 68:680-687.

Scarman et al., "Identification of novel species-specific antigens of *Mycoplasma hyopneumoniae* by preparative SDS-Page ELISA profiling," *Microbiology*, 1997, 143:663-673.

Schorey et al., "Characterization of the fibronectin-attachment protein of *Mycobacterium avium* reveals a fibronectin-binding motif conserved among mycobacteria," *Mol. Microbiol.*, 1996, 21:321-329.

Simecka et al., "Mycoplasma Diseases of Animals," *Mycoplasmas: Molecular Biology and Pathogenesis*, 1992, Maniloff et al. (eds.), Washington, D.C., American Society for Microbiology, pp. 391-415.

Southern, "Detection of Specific Sequences Among DNA Fragments Separated by Gel Electrophoresis," *J. Mol. Biol.*, 1975, 98:503-517.

Stevens and Krause, "Localization of the *Mycoplasma pneumoniae* Cytadherence-Accessory Proteins HMW1 and HMW4 in the Cytoskeletonlike Triton Shell," *J. Bacteriol.*, 1991, 173:1041-1050.

Strasser et al., "Cloning and Expression of a Species-Specific Early Immunogenic 36-Kilodalton Protein of *Mycoplasma hyopneumoniae* in *Escherichia coli," Infect. Immun.*, 1991, 59:1217-1222.

Talay et al., "Co-operative binding of human fibronectin to Sfbl protein triggers streptococcal invasion into respiratory epithelial cells," *Cell Microbiol.*, 2000, 2:521-535.

Thacker et al., "Potentiation of PRRSV pneumonia by dual infection with *Mycoplasma hyopneumoniae," The Conference of Research Workers in Animal Diseases*, 1997, Ellis (ed.), Iowa State University Press, Ames, IA, #190.

Theiss and Wise,"Localized Frameshift Mutation Generates Selective, High-Frequency Phase Variation of a Surface Lipoprotein Encoded by a Mycoplasma ABC Transporter Operon," *J. Bacteriol.*, 1997, 179:4013-4022.

Towbin et al., "Electrophoretic transfer of proteins from polyacrylamide gels to nitrocellulose sheets: Procedure and some applications," *Proc. Natl. Acad. Sci. USA*, 1979, 76:4350-4354.

Wilton et al., "Reiterated repeat region variability in the ciliary adhesin gene of *Mycoplasma hyopneumoniae," Microbiology*, 1998, 144:1931-1943.

Yogev et al., "Increased Structural and Combinatorial Diversity in an Extended Family of Genes Encoding V1p Surface Proteins of *Mycoplasma hyorhinis," J. Bacteriol.*, 1995, 177:5636-5643.

Young et al., "Isolation and Characterization of High and Low Adherent Clones of *Mycoplasma hyopneumoniae," IOM Letters. 10th International Congress of the International Organization for Mycoplasmology*, 1994, vol. 3, Bordeaux, France, pp. 684-685, #260.

Zhang et al., "Identification and Characterization of a *Mycoplasma hyopneumoniae* Adhesin," *Infect. Immun.*, 1995, 63:1013-1019.

Zhang and Wise, "Molecular Basis of Size and Antigenic Variation of a *Mycoplasma hominis* Adhesin Encoded by Divergent *vaa* Genes," *Infect. Immun.*, 1996, 64:2737-2744.

Zhang and Wise, "Localized reversible frameshift mutation in an adhesin gene confers a phase-variable adherence phenotype in mycoplasma," *Mol. Microbiol.*, 1997, 25:859-869.

Accession No. AAA56853 dated Oct. 20, 2000, 2 pages.

Accession No. AAB05967 dated Oct. 20, 2000, 2 pages.

Minion et al., "The Genome Sequence of *Mycoplasma hyopneumoniae* Strain 232, the Agent of Swine Mycoplasmosis," *J. Bacteriol.*, 2004, 186(21):7123-7133.

Adams et al., "In Vivo Expression Analysis of the P97 and P102 Paralog Families of *Mycoplasma hyopneumoniae," Infection and Immunity*, 2005, 73(11):7784-7787.

* cited by examiner

ATGAAAAAAA TACCTAATTT TAAAGGATTT TTTAATAAAC CAGCAAAAAT TGTAACTAGC ATTTTGCTTC TAAGTGGTAT TATAACTATT
TCAACTGCAA TTCCTTTAGG TATTTGGTCA TATAATCGCG CTTATTATCA AAAATTAAAT GAAAAATCAC AAAATTTAAG TATTAGTCAA
ACTGAAAATC CCTTTGAAAA TAATCTTGGA AAATTCTTTG ATAATTTATT CATTAGTAAT CAATTCAAAG AATTATCAGC TAGTACAGCA
TTTGAATTAG CAAAAAGCAA GATTTATAAT CTTGACCTTT TAACGTTAAT TAATCTTGAT AAACTATACC AAAAAAATTA CCAAATTAGT
TATGATCTAA GTAATGCAAC AGCAAGTGGA ACTGCAATTA AAAATATTGT ATTTTTTATA AGAACTAGCG ATCAACGGCA AATTTTTTCA
AAAGCAGTTG AAATTAAAGG TTTTTCTGAT AAAAATATTG AAAAAAATCT TGCTAAATTT GAAATTGATG AAAAAAAATC ATCAATTTCA
ATTAAACCGC AAAATTTTTT AAGTTTTGCT GAGTTTAGCA AGGAATTACA AAATCAATTT ATTAAAACTA GCAAAACCCA AAAACAAACA
TTTATTGCTT TTGAAGAGGC GCTTATTCAA CTTGGAGGTT CGTATAATTT AGTTAACAGT CTCGGCTTAC CAACTTTTAT TCATAAAGGG
CAAATTTTAG AACCAAAAAT TTTTGATAAT AATCTTAATT TTACAAACCA AGGGAATAAA AATTACCTTA ATTTTATCTT CACAAATGAA
GGAAAAAAAA CAGAAATTCC CTTAGAAATT AACGGAATAA CCCCTGATTT AGAGATTAAA AATGAAATAA TTAAGTGAAT AAAAGCGGAA
CTAGAAGAAA AAATCAAGCT CAAGGAAAGT ATTCAAGCTG AATTAATTAG GGAAAATTTA TCACTTGCAA AATCATTTTA TGTTGATAAA
AATAATAATC CTTTGATATC AACAACAAAA AATTTTGAAA ACTTATTTGA TTATGTACAA AGCGAGCATC TAATTAATAC TAATAAAATA
AAAAATTATA TCACAAACAT AAATTTTAAA ATCAAAAAAA ATAGTGAAAT ACCTGCTTTA GAACTTAATA ATTTGCTAAA AGATGATAAA
ATTCGGCTTG AAATAAATGT TGATATCTCA AAGTGAGTCC AACAAAAACT AATTAAAATT TTAAATTTTA AGTTTGATTG GGACCTAAAA
CCAGACCTGA ATCAGTATGC CAGGATTTTT GCACAAAATC TACCCGAGCC AAAATCTGAG GTATTCTTAC TAAAAAAAGA TGAAAATTCA
GCAGCGTGAA CTAGTAAAAA ACTAGTAAAT ATAATAAATA AAATTAAGGA ATTTAACAAT GAATTAGACC CAGAAAATCC TGATATAAAG
CTAGTTAGCC AACTTTATTT ACTTGATTTT GGCAAAATTG GTGATGAAAT TGCTATAGAA AATTATAAAA GAGAATTAAT AATAACTGCT
AAAATCCTTA AAAATCAACT AGTTAAAGTC CAAGAATTTA GTGATGATCA GGTTAATAAA GCACAAAACA ATGAAAAAAG TTTAGGAAAA
GCAATTTGAA AAGTGCTTAA TATTCAGCGT AATTTAATAA ATGATGATAT AAGCTCTGAT TTTATCCTTG ATAATAAGGA AGGTGATTTT
ACTATCGAAT TTAGTCTAAT TTCAAATAAA AATAAGCAAA AATTAGCCAC AAGAAAGATT AAAATTTCAA ATATTGTCAG TTCTGAAATG
AGCGCTTTTG ATGATGCAGC TAAATTTTAT CCAACTTTTT TTCTTGATGG CAAGTCATCT TTTTCAAAAT CAGACAATAA AAAAGGCTAT
GAAATTATAG ATTTATCTGA TAATAATATT CATTTTGAGG ATGATTTAGA TAGTAAAAAT CAACTAACTC AAGAAGGTTT TAAACTAACA
AATCCGATTA AATTTCAGCA AAACCAATCA AAAACAAAAG AAAATATTGC CAGAACAGTC AATATAAGTA GCCCAAGTTT CAAATCAGCA
CCATTTTCAC GGCTTGATTC AGGGCTAATT TATTTAGCAT TTAAACCAAA AAATATCAAT GACTATAAAA AACATTACCT ACTTGCAGAC
TCAGATGGAA ACGGTCTTTT TATTCAAAAG ATTAAAAATT TTAAATTTAT AAATAAAAAT ACCACAATCC AAGGGATTGC AGGACTAAAA
ACTGAAAAAA CTACGCAAAA TTCGGATATT ACCTTTATCA AACCCGAAAA TTTAGACCAA AAAAACAAAG ATGAAACACA ACAAAAACAA
GTTGATGGTT ATTTTATCGG ACTTGACTTT AAACAGATAA AAAATTTTAA ATCATTTCAG TCATATTTGT ACCAGAACAA AAAAAGCCTT
TATTCCTTAG CTAATTTATT CCCACCTGAA TTAATTGATA AGCAAGCAGT AATTCTTGGG CCTAATTCCT GAAAGCCAAT AAAAAATTTT
AGCGCTGAAA TAAATCAAAA TTTAGACAAT CTAGCCATAG TTGAACTTGC AAATCGAATT GGCGAAAATC GTTTTTATCG CCAGGAACTA
AGAAATTCTA GTCCTTTTTC ACTTGAAAAA AGTAAAGAAA TAATCGAAGA AGACCAAGAT ATTGTCCTTG AAATTATCAA AACTCCGTGA
TCAGTTGAAA TTAGTGCTTT TTCATCATCA AATTATCAAC TAAATTCAAA AACATCACTT AATTTAAATG GAAAAACTAT CTATAATATT
AACCCTGTAA GTCAAAAATG GTCACCATTT CCGAATTATC TAAATCTTGA CTGGGCCCAA ATTGGGCCAA ATCCAAAAAA AACAACGGAT
AAAAATGGTT CTAACAACGA AAAAATTAAC AAAAATAGCA GCATAATTTT AAAAGGAATA GCAGTTTATA ACGATCCAGA ATTAACAACA
AAGACAAGAA ATTTTGCCCG CGATCAAATA AGAAACGCCT TTATTAAAGC ATATATAAAA (SEQ ID NO:1)

Fig. 1

MKKIPNFKGF FNKPAKIVTS ILLLSGIITI STAIPLGIWS YNRAYYQKLN EKSQNLSISQ TENPFENNLG KFFDNLFISN QFKELSASTA
FELAKSKIYN LDLLTLINLD KLYQKNYQIS YDLSNATASG TAIKNIVFFI RTSDQRQIFS KAVEIKGFSD KNIEKNLAKF EIDEKKSSIS
IKPQNFLSFA EFSKELQNQF IKTSKTQKQT FIAFEEALIQ LGGSYNLVNS LGLPTFIHKG QILEPKIFDN NLNFTNQGNK NYLNFIFTNE
GKKTEIPLEI NGITPDLEIK NEIIKWIKAE LEEKIKLKES IQAELIRENL SLAKSFYVDK NNNPLISTTK NFENLFDYVQ SEHLINTNKI
KNYITNINFK IKKNSEIPAL ELNNLLKDDK IRLEINVDIS KWVQQKLIKI LNFKFDWDLK PDLNQYARIF AQNLPEPKSE VFLLKKDENS
AAWTSKKLVN IINKIKEFNN ELDPENPDIK LVSQLYLLDF GKIGDEIAIE NYKRELIITA KILKNQLVKV QEFSDDQVNK AQNNEKSLGK
AIWKVLNIQR NLINDDISSD FILDNKEGDF TIEFSLISNK NKQKLATRKI KISNIVSSEM SAFDDAAKFY PTFFLDGKSS FSKSDNKKGY
EIIDLSDNNI HFEDDLDSKN QLTQEGFKLT NPIKFQQNQS KTKENIARTV NISSPSFKSA PFSRLDSGLI YLAFKPKNIN DYKKHYLLAD
SDGNGLFIQK IKNFKFINKN TTIQGIAGLK TEKTTQNSDI TFIKPENLDQ KNKDETQQKQ VDGYFIGLDF KQIKNFKSFQ SYLYQNKKSL
YSLANLFPPE LIDKQAVILG PNSWKPIKNF SAEINQNLDN LAIVELANRI GENRFYRQEL RNSSPFSLEK SKEIIEEDQD IVLEIIKTPW
SVEISAFSSS NYQLNSKTSL NLNGKTIYNI NPVSQKWSPF PNYLNLDWAQ IGPNPKKTTD KNGSNNEKIN KNSSIILKGI AVYNDPELTT
KTRNFARDQI RNAFIKAYIK (SEQ ID NO:2)

Fig. 2

ATGCAGGCTA ATTTGATTGG CAGATTTATC AAAAATAAAA AAGCAATTTT GGTACTAGCT TCAACTTTTG CTGGGTTAAT TTTATTTACT
ACTTCTGTCG GAATTAGTTT AACAATTAAA TATAATGGTT CTCACCCGCG GGCAAAAGTT AATGAATTTG CACAAAAAAT TAGTTTTGTT
AGTTTTAAAC CTGAGCAAAT TAGTAAAAAT AGTAATTTCT GAAAAATAAA AGAAAAATTG TTTTCCGGTG ATCAGCTTAA AAAAGAAATA
AATCTTGAAG AGTATCTCCA ATTTTATATT TTTGATAAAA ATTCTAATGA TTTGGTTAAA TTCTCAAAAG ATTCAAATCC TTTTTCTATT
GAATTTGAAT TTAGTGATTT AAAATTTGAT GATTTAAACC AAAATTTTAA TCTTAAATTT CGTGTTAGGC AAAAACAAAA AAATAATCAA
TATGCATATT CGGATTTTTT CAGCCAACCA ATTACATTTT ATGAATCAAA TAAATTTTTA AAAGCAGATT TTAACTTTGT TCTTCAAAAA
ATGTTTCGCC AAATTAATGA AAATATTTTA AATATAGGTA ATTTTACCAC AAATTTTTCT GATCAAACTA GTAAAAAAAA ATTAAAAAAG
TTATACAGAG CAATTGATTT TGCGCAAGAA GTTAATAAAA TTGAAAATCC AAACGAGGTT GAGGTCAAAA TAAATGAAAT TTTCCCTGAA
TTATCTAACT TGATTTTACA AGCACGCGAA TCGAAAGATA ATAAAATTGG AAAAACAGAA AATCCGATTT TTAGTCTTAA ATTTATAAAA
AATAAAACTA ATAATCAATT TGTAAATCTA CAAGATAATA TCCCAACTAT GTATCTTGAG GCAAAATTAA CTGATCAAGC CGCAAAAATG
TTAGGTGATA TTGGTCAAAA CTTTAGCGAA AAAATCTTTG AAATTAGATT TGAAACTAAT GATAAAAAAT CATTATTTTT CAATGTTGAG
AATTTTTTTC AAAATATTAA ACTAAAACCA CTAAAATTTA ACACTGAAGA AAAAGACGGA AAATTAATAA TAACTAAACT GAATCCTTTT
GACATATTTT CAAAAATTAA ATCCGGAATT TTATCTGCCA ATACTAACCA AAATTACATA AAAGGGGTTA TTAATTCTTT ATTAGAAGAG
GATTTAGCTC TAGATTTTGG GCCGACTTCA AAACTAATTC CACAAAATCA AAACGGAATT AGTTTTGAAA TTATCCAACA AAATGCTAAA
TTAAAAAATG AAAATGATAA TTATATAATT GAAATTCCCT ATAAAATTTT CCTTAGAGAA TCCTTATTTA AACCTGGTTC ACAAAAAATT
ATCTATGAAA AAGAGTTGTT TTTAAGTATT GGCGGCTTTG GTATATCAAA TAAAAATGGT CAAAATCTAA TAATTCCAGG AAGCCAGAAA
GCTTTAATTT ATCGGAGAAA TTCACTTTTT AATGATGAGG AAAGTCCTGA AAATAAATTT ATTTCAACTT TTGGTCAACC GGTCATTTCG
AATAATCCCT TAAAAAAAGA AGAAATTGAT AATTTATTAT TGCAACAAGA TTATAAAGGT TTAGAAAGAC AGCTAAATTC ATTATCACGG
TATAATTTTA ATTTTGATAA TTTTGAGGCC AAAGTTCGGG CTTGATCTGG TAAGACATAC TTACCTAGTT TAACAGAAAT TGCAAATTTT
CGATTAAATC AACAAAAAAT TGATATAAAT TCACAAAATC AAGAGCAAAA AATTGAACTA AAAACACTAC ATTCACAAAG TTTTTTTATA
AATCCTTCGG ATGTAACAGC TTTTTTTGCT GATTTAATTC AGAAAAAACC AAGCCAAATA GCAAATAGTT TTTTCTTAAT TGCAAAGGCT
TTTGGACTTT TAAATCAAAA TCGGACTGCT TCGCAAATTT TTAATAACCT GGCTGGAGAA AATATCTTTG AAGCTAGTTC AAAAATTGAT
TTTGATAATA AAACTACAAA TATTTTAAGT TTTAATAATC ATTTCGCTGA TTTTTATAAT CAAGGGTTTT TTTCATCCCT TTTTCTTCCA
AAATCAATAA AAGATAAATT CAATAATCTA AAAAGCAAGT CAATTTCTGA TGTAATTAGT ATTTTAGAAG ACCAAGAACT TTTTAAAGAA
ACAGCTAGAA AATTTACAAG ACAACAAATT GAGGAAAACC TAAAATCAAG TGTTAAATTC ACAACATTGG CCGACCTTCT TTTAGCTTTT
TATTATAAGG CTAGTCAACT TGATAATTTT TTAGGGTGAA CAAAATTAGA TACCAATTTA GATTATCAAA TTGTGTTTCA AAAAGAAAAT
GAAATTTCAA AAGCTCGTTA TGATTCTGAA ATTCAGAAGC TAAAAAAACC CGAATTAAAT TCTTTAGAAA AACAGGAAAA CTTAAATAAA
AATTCTGAAA TTCAACCAGA ATCTAAAAAT TTAGACTCTG ATAATAACAT AAAAAAATCA ATAAATGGAA ATTTAGAAAA AGATAATACT
TATAATGCCA ATGTTGATAA TGAATATCTA ACATTAAATT TTTACTATAT TATTGGTGAT TCTAGTCAGA AAAAATTTTT CTTTCAAAGC
CCAATTCAAA AAATTTTAAT AAATTTCTCA ACTCAAAAAA TTGATGAAAA TTCTAAAATA CAAGAAAAAT TCGATAAGGT AGTTGAAAGT
GTTCCGGCTG ATTTGTTAAA TTATAGTGTC AGTGAAGAAA ATTTTAAAAA AATTAAGGAA AAATTAACAA ATAAGCATTC ACCTGAACCA
AAAAATAATG ACAATAATAA CGATTTAGAT TTATATTTTA AAGAAACTTC CATAAATATT GATAAAATTA GTTCTTATTT TAAAGAACAA
TTTCCCAAAG AGGAGACAAA ATTTTTACTT GAACCAAGTT TTGAAAACTC ACTAAATACG GATAAACTAA CCTTTTTAAT AAGTTTTTAT
CTTAATAAGA AGGATAAAAA TCCCAAAGAT TTAAAAGCTG ATAATAAAAA TGATGAAAAT AGCCCGATAA ATCCAATTAT TGCAAGGCAG
AAATTAAAAA TTATAATAAC AAAAAATTCT AAAAAT (SEQ ID NO:3)

Fig. 3

MQANLIGRFI KNKKAILVLA STFAGLILFT TSVGISLTIK YNGSHPRAKV NEFAQKISFV SFKPEQISKN SNFWKIKEKL FSGDQLKKEI
NLEEYLQFYI FDKNSNDLVK FSKDSNPFSI EFEFSDLKFD DLNQNFNLKF RVRQKQKNNQ YAYSDFFSQP ITFYESNKFL KADFNFVLQK
MFRQINENIL NIGNFTTNFS DQTSKKKLKK LYRAIDFAQE VNKIENPNEV EVKINEIFPE LSNLILQARE SKDNKIGKTE NPIFSLKFIK
NKTNNQFVNL QDNIPTMYLE AKLTDQAAKM LGDIGQNFSE KIFEIRFETN DKKSLFFNVE NFFQNIKLKP LKFNTEEKDG KLIITKLNPF
DIFSKIKSGI LSANTNQNYI KGVINSLLEE DLALDFGPTS KLIPQNQNGI SFEIIQQNAK LKNENDNYII EIPYKIFLRE SLFKPGSQKI
IYEKELFLSI GGFGISNKNG QNLIIPGSQK ALIYRRNSLF NDEESPENKF ISTFGQPVIS NNPLKKEEID NLLLQQDYKG LERQLNSLSR
YNFNFDNFEA KVRAWSGKTY LPSLTEIANF RLNQQKIDIN SQNQEQKIEL KTLHSQSFFI NPSDVTAFFA DLIQKKPSQI ANSFFLIAKA
FGLLNQNRTA SQIFNNLAGE NIFEASSKID FDNKTTNILS FNNHFADFYN QGFFSSLFLP KSIKDKFNNL KSKSISDVIS ILEDQELFKE
TARKFTRQQI EENLKSSVKF TTLADLLLAF YYKASQLDNF LGWTKLDTNL DYQIVFQKEN EISKARYDSE IQKLKKPELN SLEKQENLNK
NSEIQPESKN LDSDNNIKKS INGNLEKDNT YNANVDNEYL TLNFYYIIGD SSQKKFFFQS PIQKILINFS TQKIDENSKI QEKFDKVVES
VPADLLNYSV SEENFKKIKE KLTNKHSPEP KNNDNNNDLD LYFKETSINI DKISSYFKEQ FPKEETKFLL EPSFENSLNT DKLTFLISFY
LNKKDKNPKD LKADNKNDEN SPINPIIARQ KLKIIITKNS KN (SEQ ID NO:4)

Fig. 4

ATGAACCAAT TTGACGAAAA AGAGAAACAA CATAATAAAG CAAAAGCAAT TCTTTCAACC GGATTTTCGG TTACATCAAT TGCAACTACA
GTTGTAGCAG TCCCAATTGG ACTAACAATT TTTGAGAAAT CATTTAGTTC CCAAGTTTCA GGAGGAGTCG ATAAGAACAA AGTTGTGGAT
TTAAAATCAG ATTCAGATCA AATCTTCTCA GAAGAAGATT TTATAAGAGC AGTTGAGAAT CTTAAACTTT TTGATAAATA TAGACATCTA
ACAGCAAGAA TGGCATTAGG TCTTGCCAGG GAAGCAGCTA ATGCCTTTAA CTTTTTAGAT ACTTACGACT ACACCCCAAT TACAAAGCAT
TCATTTAAGA TTTCTTTGGA TATTTCCGAT GCCTTTGCGG CTAATAAAGA AGTAAAAGCG GTAGTAGTTA GTGCATATTC CCAAAAATAT
CAAGTTACCT ATTCAAGACT AACTTCTCTA AAAGGTTGAA AAGAAGAAGA TGATTTTGGC GATGATATTA TAGATTATCA AATTAATCAA
GAGCTTTCAG GTCTATCACT TTCTTCCCTA GCCCCTGAAA GCGCGCATCT TTTAGCCTCA GAAATGGCTT TTCGGCTTGA TAATGACTTT
CAAGTTGCAT ATAAAAAAAC AGGATCAAGA GCCGAGGCTT TTCGCCAGGC CTTGATAAAA AATTATCTTG GTTATAACTT AGTTAACCGC
CAAGGTTTGC CCACTATGCT CCAAAAGGGT TATGTGCTAG CCCCCAAAAC AATTGAAAAT AAAAATGCAA GCGAAGAAAA ATTAGTAAAT
ATAAATGAAA ATGACCGTGC AAGGGTTAAT AAACTACAAA AAGTAGAAAA TCTAGCCTTT AAAAACTTAA GCGATCCAAA TGGAACGCTT
TCTATTACTT TTGAACTCTG AGATCCAAAT GGTAAATTAG TATCCGAATA CGATTTTAAA ATTAAGGGAA TCAAAAAACT TGATTTTGAT
CTTAAAAAAC AAGAGGAAAA AGTACTTCAA AAGGTAACTG AATTTGTTGA GATTAAACCT TATGTTCAAT TAGGTTTAAT CCGTGATAAT
TTATCATTGT CTGAAATTAT CTATAAAAGT GATAATAATC CGGAGTATCT TAGGAAAATA TTAGCTAAAC TAAAAGAACA CAATAACAAC
AAAAGGGTGG ATAATAATAC ATCCACTACT AAATTTCAAG AAGAGGATCT TAAAAACGAA CCAAATTCTA ATGGATCAGA ACAAGATTCT
TTCGAGAAAG CAAAGGAAAA TTTCCTTAGT TTTTTTGATC TAAGATCGAG ACTAATTCCA ATTCCCGATC TTCCTTTATA TTATCTTAAA
GTTAATTCAA TTAATTTTGA TAGAAATATT GAAGAAAATG AAAAAGAAAA ATTATTAAAA AATGAACAAG TAGTACTCAA AGTAGATTTT
AGTCTTAAAA AAGTTGTTAG CGATATTAGA GCCCCTTATT TAGTTTCTAG TCAGGTTAGA TCAAATTATC CCCCGGTTTT GAAAGCTTCG
CTAGCAAAAA TAGGTAAGGG GTCAAATTCA AAAGTTGTCC TTTTAGATCT TGGAAATTTA TCTTCAAGAT TTAAAGTTCA ACTTGATTAT
AGTGCAAAAC AAAGAGAAAT AATTAATACT TTATTAAAGG AAAATCCAGA AAGAGAAAAA GAATTACAAG CTAAAATTGA AAGTAAGACG
TTTAGTCCAA TAGATCTTAA CAATGATGAT CTATTAGCAA TCGAATTTCA ATATGAGGAT AACCCTGAAG GAGATTGAAT AACTTTAGGG
AGAATGGAAA AGTTAGTCAA AGAGGTTATC CAATATAAAA AGGAAGGTAA AAGCTTCCTA GATGATGAAG TCGCTAAAAC ACTTTATTAT
TTAGATTTCC ATCATCTACC TCAAAGTAAA AAAGACCTCG AAGAATATAA AGAAAAACAC AAAAACAAGT TTATTAACGA AATAAAACCT
GCTACACCAG CAAGTCAAGC AAAACCAGAT CAAGCAAAAA ATGAAAAAGA AGTAAAACCT GAATCAGCCC AAGCAGAATC TTCATCTTCA
AATTCTAATG ATTCTAATAG TAAAACCACT TCTTCTTCAA GTATGATGGC GGGTACAACC CAAACAAATA ATTCCTCTAC AGAAACAACA
AATTCAAATT CAGCAACAAC AACTTCAACA ACAACACAAG CAGCAGCAAC TTCAGCCTCT TCGGCTAAAG TAAAAACAAC TAAATTCCAA
GAACAAGTAA AAGAACAAGA ACAAAAACAA GAAAAAGCAA AAGAAACTAA CCAATTATTA GATACTAAAA GAAATAAAGA AGACTCAGGG
CTTGGATTAA TTCTTTGGGA TTTCCTAGTA AATTCAAAAT ATAAAACTCT ACCAGGAACT ACCTGAGATT TCCATGTTGA ACCAGATAAT
TTCAATGATC GTCTAAAAAT AACAGCGATT CTAAAAGAAA ATACATCCCA GGCAAAGTCA AATCCAGATA GTAAAAACCT AACTTCCCTA
TCGCGAAACC TTATAATAAA AGGGGTTATG GCTAATAAAT ACATTGACTA CTTAGTCCAA GAAGATCCAG TACTTCTTGT AGATTATACA
AGAAGAAACC AGATTAAAAC CGAAAGAGAA GGACAACTAA TTTGAAATCA GTTAGCTTCC CCTCAAATGG CATCTCCTGA AACTAGTCCC
GAAAAGGCTA AGCTCGAGAT CACCGAGGAA GGACTCCGTG TTAAAAAAGG TGGCACTAAG ATAAAAGAGA CAAGAAAAAG CACAACCAGC
AATGCTAAAA GCAATACTAA CTCCAAACCA AATAAAAAGT TAGTCCTACT AAAAGGGTCT ATAAAAAACC CGGGAACAAA AAAGGAATGA
ATTCTTGTAG GATCTGGGAA TAACGCCACC AAAAACGGAA GCTCCAGCAA CAACTCCAAT ACCCAAATAT GAATAACCAG ACTAGGAACA
TCTGTTGGTT CATTAAAAAC CGAAGGTGAG ACAGTCCTTG GAATTTCAAA TAATAATTCC CAAGGTGAAG TTCTCTGAAC TACTATTAAA
TCCAAACTCG AAAACGAAAA TCAATCAGAT AACAATCAAA TCCAATACTC CCCAAGTACG CATAGTTTAA CAACCAATTC TCGATCAAAT
ACCCAACAAT CAGGGCGAAA TCAAATTAAA ATTACAAACA CTCAAAGAAA AACAACTACT TCGCCGGCCC AAAGCCCAAT ACAAAATCCT
GATCCGAACC AAATTGATGT AAGACTTGGT CTACTAGTAC AAGACAAAAA ACTTCATCTT TGGTGGATTG CTAATGATAG CTCTGATGAG
CCTGAGCATA TAACAATTGA TTTCGCTGAA GGGACAAAAT TTAATTATGA TGATTTAAAT TATGTCGGAG GGCTTTTAAA AAATACTACA
AATAATACCA ATACCCAAGC CCAAGACGAT GAAGGTGATG GATATCTGGC CCTAAAAGGA TTAGGGATCT ATGAATTTCC TGATGATGAA
AGTATTGATC AAGCCGCTAC TGTTGAAAAA GCAGAGAGAT TATATAAACA CTTTATGGGG CTATTTAGGG AA (SEQ ID NO:5)

Fig. 5

MNQFDEKEKQ HNKAKAILST GFSVTSIATT VVAVPIGLTI FEKSFSSQVS GGVDKNKVVD LKSDSDQIFS EEDFIRAVEN LKLFDKYRHL
TARMALGLAR EAANAFNFLD TYDYTPITKH SFKISLDISD AFAANKEVKA VVVSAYSQKY QVTYSRLTSL KGWKEEDDFG DDIIDYQINQ
ELSGLSLSSL APESAHLLAS EMAFRLDNDF QVAYKKTGSR AEAFRQALIK NYLGYNLVNR QGLPTMLQKG YVLAPKTIEN KNASEEKLVN
INENDRARVN KLQKVENLAF KNLSDPNGTL SITFELWDPN GKLVSEYDFK IKGIKKLDFD LKKQEEKVLQ KVTEFVEIKP YVQLGLIRDN
LSLSEIIYKS DNNPEYLRKI LAKLKEHNNN KRVDNNTSTT KFQEEDLKNE PNSNGSEQDS FEKAKENFLS FFDLRSRLIP IPDLPLYYLK
VNSINFDRNI EENEKEKLLK NEQVVLKVDF SLKKVVSDIR APYLVSSQVR SNYPPVLKAS LAKIGKGSNS KVVLLDLGNL SSRFKVQLDY
SAKQREIINT LLKENPEREK ELQAKIESKT FSPIDLNNDD LLAIEFQYED NPEGDWITLG RMEKLVKEVI QYKKEGKTFL DDEVAKTLYY
LDFHHLPQSK KDLEEYKEKH KNKFINEIKP ATPASQAKPD QAKNEKEVKP ESAQAESSSS NSNDSNSKTT SSSSMMAGTT QTNNSSTETT
NSNSATTTST TTQAAATSAS SAKVKTTKFQ EQVKEQEQKQ EKAKETNQLL DTKRNKEDSG LGLILWDFLV NSKYKTLPGT TWDFHVEPDN
FNDRLKITAI LKENTSQAKS NPDSKNLTSL SRNLIIKGVM ANKYIDYLVQ EDPVLLVDYT RRNQIKTERE GQLIWNQLAS PQMASPETSP
EKAKLEITEE GLRVKKGGTK IKETRKSTTS NAKSNTNSKP NKKLVLLKGS IKNPGTKKEW ILVGSGNNAT KNGSSSNNSN TQIWITRLGT
SVGSLKTEGE TVLGISNNNS QGEVLWTTIK SKLENENQSD NNQIQYSPST HSLTTNSRSN TQQSGRNQIK ITNTQRKTTT SPAQSPIQNP
DPNQIDVRLG LLVQDKKLHL WWIANDSSDE PEHITIDFAE GTKFNYDDLN YVGGLLKNTT NNTNTQAQDD EGDGYLALKG LGIYEFPDDE
SIDQAATVEK AERLYKHFMG LFRE (SEQ ID NO:6)

Fig. 6

ATGAAAAACA AAAAATCAAC ATTACTATTA GCCACAGCGG CAGCAATTAT TGGTTCAACT GTTTTTGGAA CAGTTGTTGG TTTGGCTTCA AAAGTTAAAT ATCGGGGTGT
AAATCCAACT CAAGGAGTAA TATCTCAATT AGGACTGATT GATTCTGTTG CATTTAAACC TTCGATTGCA AATTTTACAA GCGATTATCA AAGTGTTAAA AAAGCACTTT
TAAATGGGAA AACCTTTGAT CCAAAAAGTT CAGAATTTAC TGATTTTGTC TCAAAATTTG ACTTTTTGAC TAATAATGGG AGAACCGTTT TGGAGATCCC GAAAAAATAT
CAGGTGGTTA TCTCGGAATT TAGCCCCGAG GATGATAAAG AACGTTTTCG TCTTGGATTT CATCTAAAAG AAAAACTTGA AGATGGAAAT ATAGCTCAAT CAGCAACTAA
ATTTATTTAT CTTTTACCAC TTGATATGCC CAAAGCGGCC CTGGGTCAAT ATTCTTATAT CGTTGATAAA AATTTTAATA ATTTAATTAT CCATCCTTTA TCTAATTTTT
CTGCTCAATC AATAAAGCCG CTTGCACTGA CCCGTTCAAG TGATTTTATA GCAAAACTTA ATCAGTTTAA CAATCAGGAC GAGCTTTGAG TTTATCTGGA AAAATTCTTT
GATCTTGAAG CTCTAAAAGC AAATATTCGC TTACAGACAG CCGATTTTAG TTTTGAAAAA GGCAATTTAG TTGATCCTTT TGTTTATTCT TTTATTAGAA ATCCGCAAAA
TCAAAAAGAA TGAGCTAGTG ATCTTAATCA AGATCAAAAA ACTGTCAGAC TTTATCTTCG AACCGAATTT AGTCCTCAGG CTAAAACCAT TTTAAAAGAC TATAAATACA
AAGATGAGAC TTTCTTAAGT AGTATCGATT TAAAAGCAAG TAATGGAACT AGTTTATTTG CTAATGAAAA TGATCTAAAA GATCAATTAG ATGTTGATCT TTTAGATGTC
TCTGATTATT TTGGAGGCCA ATCAGAGACA ATTACTAGTA ATTCCGAAGT TAAACCTGTC CCTGCTAGTG AGAGATCTTT AAAAGACCGG GTTAAATTTA AAAAAGATCA
GCAAAAACCA AGAATTGAGA AATTTAGTTT ATATGAATAT GATGCTCTAA GTTTTTATTC CCAACTTCAA GAATTAGTTT CTAAACCTAA TTCAATTAAA GATTTAGTTA
ATGCAACTTT AGCTCGTAAT CTTCGGTTTT CATTAGGAAA ATATAATTTT CTTTTTGATG ATTTAGCCAG TCATCTTGAT TATACTTTTT TAGTTTCAAA AGCAAAAATT
AAACAAAGTT CAATTACAAA AAAATTATTC ATTGAATTAC CAATCAAAAT TAGTCTTAAA TCTTCAATTT TAGGTGATCA AGAACCTAAT ATTAAAACTT TATTCGAAAA
AGAAGTGACT TTTAAATTAG ATAACTTCCG TGATGTTGAA ATCGAAAAAG CTTTTGGACT TTTATATCCA GGTGTTAATG AAGAACTTGA ACAAGCCCGA AAAGCTCAAA
GAGCAAGCTT TGAAAAAGAA AAATCGAAAA AAGGTCTTAA AGAATTTAGT CAACAAAAAG AAGAAAATTC AAAAGCGATA AACAATCAAG AGGGTCTTGA AGAAGATGAT
AATATTACTG AAAGACTTCC TGAGAATTCC CCGATTCAAT ATCAGCAAGA AAATGCCGGT TTAGGTGCAA GTCCGGATAA ACCTTATATG ATAAAGGATG TCCAAAATCA
ACGTTATTAT CTAGCAAAAT CACAAATTCA AGAACTAATT AAGGCCAAAG ATTATACCAA ATTAGCCAAA CTTTTATCCA ATAGACATAC TTATAATATT TCTTTAAGAT
TAAAAGAACA ACTTTTTGAT GTAAATCCAA GAATTCCGAG CTCTAGAGAT ATAGAAAAGG CAAAATTTGT TCTTGATAAA ACCGAAAAGA ATAAATACTG GCAGATTTAT
TCAAGTGCTT CTCCTGTTTT CCAAAATAAA TGATCACTTT TTGGATATTA CCGTTATTTA TTAGGTCTTG ATCCAAAACA AACAATCCAC GAATTAGTAA AATTAGGACA
AAAAGCGGGT CTTCAATTTG AAGGATATGA AAATCTTCCT TCTGATTTCA ATCTTGAGGA TCTTAAGAAT ATTAGGATTA AAACACCTTT ATTTAGTCAA AAAGATAATT
TCAAATTATC TTTACTTGAT TTTAATAATT ATTATGACGG TGAAATTAAA GCCCCAGAAT TTGGTCTTCC TTTATTTTTG CCAAAAGAAT TAAGAAGAAA TAGTTCAAAT
TCTGGTGGTT CTCAAAACTC TAATAGCCCT TGAGAACAAG AAATTATTAG CCAATTTAAA GATCAAAATC TATCTAATCA GGATCAGTTA GCCCAGTTTA GTACTAAAAT
CTGGGAAAAA ATCATTGGTG ATGAAAACGA ATTTGATCAA AATAACAGAC TTCAGTATAA ACTTTTAAAA GATCTTCAAG AATCTTGGAT TAATAAAACC CGCGATAATC
TTTATTGGAC TTATCTAGGT GATAAACTTA AAGTTAAACC AAAAAATAAT TTAGAGGCTA AATTTAGACA AATTTCCAAT TTACAAGAGC TTTTAACTGC TTTTTATACT
TCAGCTGCTC TTTCTAATAA CTGAAATTAT TATCAAGATT CAGGAGCAAA GTCAACTATT ATTTTTGAAG AAATAGCTGA GCTAGATCCA AAAGTAAAAG AAAAAGTTGG
AGCTGATGTT TATCAATTAA AATTCCATTA TGCAATCGGT TTTGATGATA ATGCTGGTAA GTTTAATCAA GAAGTAATTC GTTCTTCAAG TAGAACAATT TATCTTAAAA
CCTCAGGGAA ATCCAAATTA GAAGCAGATA CAATTGATCA ACTTAATCAA GCAGTTAAAA ATGCACCTTT AGGTCTTCAA AGTTTTTATC TTGATACTGA AAGATTTGGG
GTTTTCCAAA AATTAGCCAC TTCCTTAGCA GTTCAACATA AACAAAAAGA AAAAACACTA CCTAAAAAAC TAAATAATGA TGGCTATACT TTAATTCATG ATAAACTTAA
AAAACCAGTA ATTCCCCAAA TTAGTTCAAG TCCAGAAAAA GACTGATTTG AAGGTAAATT AAACCAAAAC GGGCAAAGCC AAAATGTAAA TGTCTCAACT TTTGGCTCAA
TAATCGAGTC CCCTTATTTT AGTACTAATT TCCAAGAAGA TGCTGACTTA GACCAGGATG GACAAGATGA TTCAAGACAA GGAAATAATA GTCTAGATAA TCAAGAAGCA
GGTCTTTTAA AACAAAAACT GGCAATTTTA TTAGGTAATC AATTTATCCA ATATTATCAA CAAAATGATA AAGAAATTGA ATTCGAGATT ATCAATGTTG AGAAAGTTTC
AGAGCTTAGT TTCCGCGTTG AATTTAAATT AGCAAAAACT CTTGAAGACA ACGGAAAAAC TATTCGAGTT TTATCAGATG AGACAATGTC ATTAATGTTT AATACTACAA
TTGAAAAAAC ACCAGAAATG AGTGCGGTTC CCGAAGTATT TGATACTAAA TGGGTTGAGC AATATGATCC AAGAACCCCG CTTGCGGCAA AGACAAAGTT TGTCTTAAAA
TTCAAAGATC AAATACCAGT GGATGGCAGT GGAAATATTT CTGATAAATG ACTAGCAAGT ATTCCTTTGG TGATTCACCA ACAAATGTTG CGTCTTAGTC CTGTGGTTAA
AACGATAAGA GAGCTCGGTC TAAAGACCGA ACAACAACAA CAACAACAAC AACAACAACA ACAACAACAA CCCCAAAAGA AAGCTGTTAG AAAAGAGGAA GAACTAGAAA
CCTATAATCC AAAAGACGAG TTTAATATTC TTAATCCTTT GACAAAAGCT CACCGCCTTA CCTTATCAAA TTTGGTAAAT AATGATCCAA ATTATAAAAT TGAAGATTTA
AAAGTAATCA AAAATGAAGC TGGTGACCAT CAATTAGCAT TTTCTCTAAG AGCTAATAAT ATCAAAAGAT TAATGAATAC ACCAATTACT TTTGCTGATT ATAATCCCTT
TTTCTATTAT AATGAAGACT GAAGAAGTAT AGATAAATAT TTAAATAATA AAGGAAATGT GAGTTCTCAC CAACAACAAG CAGCCGGGGG TAATCAAGGC TCGGGTCTAA
TCCAAAGACT TAATAAAAAT ATTAAGCCCG AAACTTTTAC CCCCGCACTC ATAGCTCTTA AACGAGATAA TAATACTAAT CTTTCTAACT ATTCTGATAA AATAATAATG
ATCAAACCAA AATATTTGGT TGAACGATCA ATTGGTGTTC CCTGATCAAC CGGCCTTGAT GGTTATATTG GTTCAGAACA AACCAAGGAC GGAACTTCCT CAAGCAGTCA
ACAAAAGGGA TTTAAGCAAG ATTTTATTCA GGCTTTAGGT CTTAAAAACA CTGAATATCA TGGTAAACTA GGTCTTTCAA TTAGAATTTT TGATCCTGGA AATGAACTAG
CAAAAATTAA GGATGCTTCA AATAAAAAAG GGGAAGAAAA GCTGTTAAAA TCATATGATT TATTTAAAAA CTATTTAAAT GAATATGAGA AAAAATCCCC TAAAATTGCT
AAGGGATGAA CAAATATTCA TCCTGATCAA AAAGAATATC CAAATCCAAA TCAAAAACTA CCTGAAAATT ATCTTAACCT AGTTTTAAAT CAACCTTGAA AGGTTACTTT
ATATAATTCA AGTGATTTTA TTACTAATTT ATTTGTTGAA CCTGAAGGCT CAGATCGTGG ATCAGGAACA AAATTAAAAC AAGTAATCCA GAAGCAAGTT AATAATAACT
ATGCTGACTG GGGGTCTGCA TATCTCACGT TCTGGTATGA TAAAAATATC ATTACCAATC AGCCAAATGT TATAACTGCA AACATTGCTG ATGTCTTTAT TAAAGATGTA
AAAGAACTTG AAGATAATAC AAAACTAATT GCTCCAAATA TTACTCAATG ATGGCCAAAT ATTAGCGGCT CAAAAGAGAA ATTTTATAAG CCAACAGTGT TTTTTGGTAA
TTGAGAAAAT GAAAACAGCA GTATGAATTC CCAGGCGCAG ACCCCTACCT GGGAGAAGAT CAGAGAAGGA TTTGCTCTCC AAGCGCTTAA ATCCAGCTTT GATCAAAAAA
CAAGGACATT TGTCCTTACA ACAAATGCTC CTTTACCTTT ATGAAAATAC GGACCATTAG GTTTCCAAAA TGGGCCGAAT TTCAAAACAC AAGATTGAAG GCTTGTTTTC
CAAAATGATG ATAACCAAAT AGCCGCGCTA AGAGTCCAGG AGCAAGATCG CCCAGAAAAA TCAAGCGAAG ATAAAGACAA GCAAAAATGG ATTAAATTTA AAGTTGTTAT
CCCTGAAGAA ATGTTTAATT CCGGTAATAT ACGTTTTGTT GGGGTAATGC AGATCCAAGG TCCTAATACT TTATGACTTC CAGTGATTAA TTCTTCGGTT ATCTATGACT
TCTATCGCGG AACAGGAGAT TCTAATGATG TCGCCAATCT TAATGTAGCT CCTTGACAGG TTAAAACAAT CGCATTTACA AATAACGCCT TTAATAATGT TTTCAAAGAG
TTTAATATCT CTAAAAAAAT AGTAGAA (SEQ ID NO:7)

Fig. 7

MKNKKSTLLL ATAAAIIGST VFGTVVGLAS KVKYRGVNPT QGVISQLGLI DSVAFKPSIA NFTSDYQSVK KALLNGKTFD PKSSEFTDFV SKFDFLTNNG RTVLEIPKKY
QVVISEFSPE DDKERFRLGF HLKEKLEDGN IAQSATKFIY LLPLDMPKAA LGQYSYIVDK NFNNLIIHPL SNFSAQSIKP LALTRSSDFI AKLNQFNNQD ELWVYLEKFF
DLEALKANIR LQTADFSFEK GNLVDPFVYS FIRNPQNQKE WASDLNQDQK TVRLYLRTEF SPQAKTILKD YKYKDETFLS SIDLKASNGT SLFANENDLK DQLDVDLLDV
SDYFGGQSET ITSNSQVKPV PASERSLKDR VKFKKDQQKP RIEKFSLYEY DALSFYSQLQ ELVSKPNSIK DLVNATLARN LRFSLGKYNF LFDDLASHLD YTFLVSKAKI
KQSSITKKLF IELPIKISLK SSILGDQEPN IKTLFEKEVT FKLDNFRDVE IEKAFGLLYP GVNEELEQAR KAQRASFEKE KSKKGLKEFS QQKEENSKAI NNQEGLEEDD
NITERLPENS PIQYQQENAG LGASPDKPYM IKDVQNQRYY LAKSQIQELI KAKDYTKLAK LLSNRHTYNI SLRLKEQLFD VNPRIPSSRD IEKAKFVLDK TEKNKYWQIY
SSASPVFQNK WSLFGYYRYL LGLDPKQTIR ELVKLGQKAG LQFEGYENLP SDFNLEDLKN IRIKTPLFSQ KDNFKLSLLD FNNYYDGEIK APEFGLPLFL PKELRRNSSN
SGGSQNSNSP WEQEIISQFK DQNLSNQDQL AQFSTKIWEK IIGDENEFDQ NNRLQYKLLK DLQESWINKT RDNLYWTYLG DKLKVKPKNN LEAKFRQISN LQELLTAFYT
SAALSNNWNY YQDSGAKSTI IFEEIAELDP KVKEKVGADV YQLKFHYAIG FDDNAGKFNQ EVIRSSSRTI YLKTSGKSKL EADTIDQLNQ AVKNAPLGLQ SFYLDTERFG
VFQKLATSLA VQHKQKEKTL PKKLNNDGYT LIHDKLKKPV IPQISSSPEK DWFEGKLNQN GQSQNVNVST FGSIIESPYF STNFQEDADL DQDGQDDSRQ GNNSLDNQEA
GLLKQKLAIL LGNQFIQYYQ QNDKEIEFEI INVEKVSELS FRVEFKLAKT LEDNGKTIRV LSDETMSLIV NTTIEKTPEM SAVPEVFDTK WVEQYDPRTP LAAKTKFVLK
FKDQIPVDGS GNISDKWLAS IPLVIHQQML RLSPVVKTIR ELGLKTEQQQ QQQQQQQQQQ PQKKAVRKEE ELETYNPKDE FNILNPLTKA HRLTLSNLVN NDPNYKIEDL
KVIKNEAGDH QLAFSLRANN IKRLMNTPIT FADYNPFFYY NEDWRSIDKY LNNKGNVSSH QQQAAGGNQG SGLIQRLNKN IKPETFTPAL IALKRDNNTN LSNYSDKIIM
IKPKYLVERS IGVPWSTGLD GYIGSEQTKD GTSSSSQQKG FKQDFIQALG LKNTEYHGKL GLSIRIFDPG NELAKIKDAS NKKGEEKLLK SYDLFKNYLN EYEKKSPKIA
KGWTNIHPDQ KEYPNPNQKL PENYLNLVLN QPWKVTLYNS SDFITNLFVE PEGSDRGSGT KLKQVIQKQV NNNYADWGSA YLTFWYDKNI ITNQPNVITA NIADVFIKDV
KELEDNTKLI APNITQWWPN ISGSKEKFYK PTVFFGNWEN ENSSMNSQAQ TPTWEKIREG FALQALKSSF DQKTRTFVLT TNAPLPLWKY GPLGFQNGPN FKTQDWRLVF
QNDDNQIAAL RVQEQDRPEK SSEDKDKQKW IKFKVVIPEE MFNSGNIRFV GVMQIQGPNT LWLPVINSSV IYDFYRGTGD SNDVANLNVA PWQVKTIAFT NNAFNNVFKE
FNISKKIVE (SEQ ID NO:8)

Fig. 8

TTGATTTTAA TTGAAGAAAT TAAGGAAATC AAAAAATTTA TGGAAAACAC CAACTTGCAC TACAAAAAAA AAAAAAAAAA
AAGCACTAAC CTTTCTAGAA AAAATCTTTT AACAATTGGG GCCGCAGTTT TTTTCGGAAT TGCAATAATC ACAATTCCGC
TTGTCACCGT TGCTAATTGA AAGATCAAAG ATCCACGACT TCAAGTACAA AATCAAGCAA AATTAATTAC AAATATTCAA
CTAAAAGATG AGTATCAAAA TGGAAATTTA AGCTATTTTG ATCTTAAAAA ACAGCTTTTT AATGCTGATA ATACTAAAAA
AACTGGGATT GACTATAGCC AGTTTTTTGA TTTTTACCAA AAAAATAACA CGAGCCTACC AATTAATTTT GCCACTGATT
ATGGCTGAAA TCGTTACAAA CTTGATGTTT TTGATCTAAA ACCACTTGAT CAAGAACAAT CTTTTGAAAT TTATTATCGT
TTAGTATATC AACTACCTGA TGATAAAAAG GCAATTTCTG ATCTTTTAAC CCAAAAAGTT ATCTGAAATT ATCTCCCTGA
TTATTCACTT GCTAATTTCG CTAATTTTTC AAGTTCAAAA TTGGAAAAAC TAAGAGCTTA TACCAACAAG GAATTTAGTT
TATCAACCAA AAAAGAACTT ACAAAATTAG TAAAATTAGA AGACTTTGAA AAGCAAGTAA ACTGGGCAAT AAATAATAAT
GAAGCCCGCA AAATTATTAA TAAATATTTT AATTTAGAAG AAATTATTGC CGAGATTCTT AATAATAAAG AATTTTCTTA
TCTAGATGAA AGTGGAATAT GAAATCCGCA ATATCAGATT GAACTTGTAA GAGATCAAAT TTTAGGTCAG GATTTTTTAG
CAAAAACAGG TCAAAAAGGA ATTTATAAAT TAACATTTTA TGCTGCTTTT TCGCCGAATT TTGCTAAAAA AATTGCGGCT
GATCTCAATA AAAGTTCAAA GTTTCATTTT GGAATTAACA TTGATCTTAA TAATCTTTTC CTTGATAAAA CAGTCGCTGA
AAATATTAAA ATAACTGAAT TTTCTGAAGA TGATTATTAC CCACAAATAA ATTTTGAAAA AAATTTAGAA GCCGAAATTA
ATGGTTGAGA TTTTCTAAAT TATTACAATA ACCAAATTTT TGCAACTCAA AACGAGAGAG AAGATTTTCT CAAGAACCTT
ATAGCAAAAA TTGTTAGAAC TCCGCTTCTG AAAAAAGTTG AATTTGAAAA TAAATTATCC GGTATTGATT ATGCAAAATT
TTTAAAATAT TTAAAATTAG ATATTAAATT AGATGCTAAT TCAACTAAAT TGGCTTTTAA AAATAACCAA ATTGTTGCCA
AAATTTTCGG AAAAATTATT CTTAGAAATG CTGAAAATCA AATTGTCGCT GAAAAAAACT TTTCCCAAAC TATTGAACAT
CTAAACCGTC TCGGGCAAAA TGATGCTGAA TTAGTAAAGC AAATTAAACA GACAAAATTT GAATTTAAAC CAGAAACTAG
AAAAAAAATT GCAAACCAAA AGGGTGCGCC AAAATCAGAA ATTCTTGCAC TCTTAAATGC CAATAAATTT GATAAATTAA
AAAATATCCT TGAAAATGGT GATTATTATG GCTATGAATT TAACGAAGAT CGCTTAAAAT TATTAGTTCA TAATTCACAA
TTACCTAATG TTGAAGAATT TGCAAAATTA AGTGTAGTTC CTGAGAAAAT GTCTGAGGGA ATTATTAATC TTTGGAATAA
GTCATTTAAA ACAAATCAAG AGGTTAGTAC ATTTTTATCT TTACTTGCAA AAAGGGATAT CAGTTTTGTT GCAAAATATT
GATATGATCT TTTAAATAAA TTTAAATTAA TTGATCCAAA AACACAATGG CCTGAAAATC TTGACCAAAA TAGTTTATTT
AAACATTTAA GTCAAATAAA AATTCAGCCT CCTGAGAAAA AAGCAGTTTC ACTGACCTCC GATTTTTGAC TTTTTTCATT
AAATAATGAC TACCTAATTT CCCCTGATTA TCTTAATAAT AGTTTTTACC TTCACTCAAA TTTAAAAAAT ACTTTGGACT
TAATCAAAAC TGAAAGCGCA TTTAACACGA GAGATTTTGT CGAACATATA AGAGAACTTG CAAAATCAAT TAAACCAAAA
GATTTTATCC AAGAAAAAGG TAAAAATCCA ATTACAAATC TTAGTGAATT TCTAGTTGCT TTTTATTCGC TTATTTATTC
AAAGGATCAA GGACTTCTTG CTGAATCACT CGGGCAAAAT TTAGACTATA AAATTCAGTT TGAACTCGAA CCTATAAGCC
TAAATGTAGC AGTTAGTCAG GAAAAAACTA ATCCAAATAA TAATTTAAGA TTAAATAATA ATTTAAGATT AAAATATTGA
TATAAAATTG GTTCAGTTGA TCAAAATGGG AATTTAATTC AAGTGATTTA CCAAACAAAA AAAGAAACTT TGGATCTTGT
AGTTAATGAA AATAATAAAT TGCTTAGTGA AGATGTAGAA AAATTAAATG AAATTGCTAC TAATTTTCCA AGTGCAGACC
AAATTATTTT CCTTAAAAAA GAAGATTATA CCCAACTTGT TGATAGTATA AAACAAGTAA TTAAAACGGA AAATACTCCA
GTTAAAATTG ATAATCAGAT CAAAAATCTA CCTTTTAGTC AATTTTTTGA AAATAATTAC CCAGATTATG GTTTTTATAT
AATAAAAACA AGTAAAAATT TAGAAAGTAG TAAACCTGAA GCAGCAAAAG TTGCTGCAAA ACCTTCAGCA GCCAAGCCAG
TAGCAGCTAA ACCAGAACAA CAAGAAATTC ATCAAAGCGA AGAAATTCCC GGAGTTCTTA CTAATACAAT ATCTCAACTT
GGCAATCAGA TACGACATAA TTTTGATTTA TATGTATACA AAAAAGATCA GCCACAGATT CACTCAAGTA AGCCAGTTAG
GGTAATTATT ATTGAAAGTT CAGAATCACT ATTTGCTTTA AAA (SEQ ID NO:9)

Fig. 9

MILIEEIKEI KKFMENTNLH YKKKKKKSTN LSRKNLLTIG AAVFFGIAII TIPLVTVANW KIKDPRLQVQ NQAKLITNIQ
LKDEYQNGNL SYFDLKKQLF NADNTKKTGI DYSQFFDFYQ KNNTSLPINF ATDYGWNRYK LDVFDLKPLD QEQSFEIYYR
LVYQLPDDKK AISDLLTQKV IWNYLPDYSL ANFANFSSSK LEKLRAYTNK EFSLSTKKEL TKLVKLEDFE KQVNWAINNN
EARKIINKYF NLEEIIAEIL NNKEFSYLDE SGIWNPQYQI ELVRDQILGQ DFLAKTGQKG IYKLTFYAAF SPNFAKKIAA
DLNKSSKFHF GINIDLNNLF LDKTVAENIK ITEFSEDDYY PQINFEKNLE AEINGWDFLN YYNNQIFATQ NEREDFLKNL
IAKIVRTPLL KKVEFENKLS GIDYAKFLKY LKLDIKLDAN STKLAFKNNQ IVAKIFGKII LRNAENQIVA EKNFSQTIEH
LNRLGQNDAE LVKQIKQTKF EFKPETRKKI ANQKGAPKSE ILALLNANKF DKLKNILENG DYYGYEFNED RLKLLVHNSQ
LPNVEEFAKL SVVPEKMSEG IINLWNKSFK TNQEVSTFLS LLAKRDISFV AKYWYDLLNK FKLIDPKTQW PENLDQNSLF
KHLSQIKIQP PEKKAVSLTS DFWLFSLNND YLISPDYLNN SFYLHSNLKN TLDLIKTESA FNTRDFVEHI RELAKSIKPK
DFIQEKGKNP ITNLSEFLVA FYSLIYSKDQ GLLAESLGQN LDYKIQFELE PISLNVAVSQ EKTNPNNNLR LNNNLRLKYW
YKIGSVDQNG NLIQVIYQTK KETLDLVVNE NNKLLSEDVE KLNEIATNFP SADQIIFLKK EDYTQLVDSI KQVIKTENTP
VKIDNQIKNL PFSQFFENNY PDYGFYIIKT SKNLESSKPE AAKVAAKPSA AKPVAAKPEQ QEIHQSEEIP GVLTNTISQL
GNQIRHNFDL YVYKKDQPQI HSSKPVRVII IESSESLFAL K (SEQ ID NO:10)

Fig. 10

ATGAAAAAAA ACAAGCTAAA ATATTTAATT TTCTCAATTA TTGGAATTAG TACAATTATA AGTCTTGCTG TTACAATTCC TTATGCACTT
TCATCCCAAG CCGAAAAATA TAATCTAGAA CTAAATTCTT ATAACATTGA TCTTGGAAAA GCACAAAATT TGAACTCAAG AACTAATTTT
AATAGTGCTG AATTTGATAA ATTAGTTGCA AATTTAAAGG TAAAACCTAA ATTTGCCAAG CGACTAAACG CTTTTGATGC TCTAAATTTT
CACTTTGATA AATCTTATAG TTTCGATCTA GCTGATGCAG TTGATTTAAG TAGTCTAAGT CAAAAATATC CTGATCTAAG TTTTAAATTG
GTTATCCCTG ATAATAAATC CAGGTTTGAA ATCAAAGAAA ATAAGCTAAA AAATATCGGA CTTAATGTAA CTAACACTTC AAAAACCATA
AATTATACAG CAAAATTCGA CCTTGATTTC TCAGGTCAAG AAAAGTCTTT CCAATTTCTA CCCGAAAATT TCACTGGCCA AATTAGTCTT
AGAAATCTTG AATCACTTAA AGGAAAAACC GCAACTGAAA TAGCAATTTT ATTTTATAAT GCTTGACTAA AACGGTTTAA TAAACTTTCT
GATTCAAAAA TTGCCTTATA TGAAACTTTT GGCGAATTTG GTGGGGCTTC CTTTAGCCTA AATTCTGAAC CAATTTTTAT CCTTCCAGAA
AATTTTGAAA TCAAACCGGA TCTAAAAGAT AATAAACTAG TTTTTGCAAG TATAAATGAT GAAAAAAATG AGCTTGTTCT TAATATGGTT
TTATATGATA AAACAGCTAA AACTGAGAAA ATTTTTCCCC TTAGATTTGT TGATCTCCCA AAAACAAATC AGAAATATGG GGAAAAATTT
TTAGCAAGTT TTTTGAAAAA CTATGAATTT AATAGTGAAA TTTCAAAATA TCTAGCCAAA AATAACTTAG ATATTGCACA ATTATTTTCA
TTACCTTCTG ATCCAAAAAG TCTTGATTTA ACTAAATTTG AGTCCTGATT TATTCAAAAA TCAGTGCCAA ATACAACTTT TTTTGCTGAT
ATTAAAGGTT TAATTCCTAA TTTTGAGACC AAAAAAGCAG CTTTTTTAGT TAAAAAACCT GAAAAAGTTG GTCAGAATAA GAATTTATTA
ACTATTAATT TAAAATTAGA AGGAACTTTT TTAGTAAATG ATCAAGTTCC TGCAGGTCTA AATTTGACTC AGGATAAACA CTATACTTAT
AATTTCGACT TTGACTACGA TGCAACACAA GAAATTTATT CTGGATATTT TCGAAATGCG CTTGAATTAT TTGATGCTAG AACGGCAAAA
AATCTTGATA ATTTAAAACT TGAGGTCAAA AACGATCTTC CAGTAACGGT TTTCGCCTCA ACAATTAATA CAAAAATTGC CCATCTTTTA
AATAAACCCC TTGAACTTAA GGGAATTACT AAAAAAATGA GTCCTTTATT TGATTTTCTT AATTTTTCAA CAAGTAAAAA TGAAAAATTA
GAAACAAAAA TGGCTCCACC AAATGCTAAG ATGCAAAATG TTGGTGCAAT TTTATTTAAT GAAGAGGTAA AACAACAAGA AAGTCAGGTA
AAGGATCAGG CAAAACAAGA AAAATCAAGT AAAGATTCCC AAAGTAAACA AACTGATCAA AGTGAAAAAG AACCAAAAGT TGAAACTAAA
ACAATCCAGG CAGAAAATGG AGGAACTTAT TTATCTAAAC TTTTTGAAAA TTTAGAAAAA ACTAGTTTCC CAACAAACAC TCTATTATAT
TTATCAACTT TTTATCGGGA TAAATTTATT TTAAAATTAG AACTAAAAGC TGAAGGAATA ACAAAAGAAA CACTTGAGAT TAAAATTGAC
AAAGTTGCTC CTGATAATAA AGCTTATCAA GCATTAGTCC AAAGTACAAA TACGGATTTA TTCCTTGATT GACGATCAAA TATAACCACA
ACAACAGAAA AATACCAAAA TAAACCAGTA ATTGCATCGA TTAGCGCACT AAATAATCCG AATTTAAAAT TTAAGGTAAA TCCAGAACCT
TCAAATAAAT CGCAGCAAAA AGTACATCTA GATCAAGCCG GTATTTATTT AGCCGAAGGG GGAATAAGTC TTGAAAACTT AAGTCAAGAA
CAAGCAAAAA ATCTTAAACT TGATGAAGGC AAGACAATTT TTTATGCCTT TAAACCCACT AAATTATCAC GAAGATCACT TTTAAGATAT
TTTCTATTAA GCGCAAGTGA TAATTCTAGT TCAAAATTCA GTTTATTAAT CGAACCAGAA ATATTACTAA CCGGGTTTAA TAAAATTGGT
GCTGATTTTG AAAAGGTAGA GCAAAATAAT AAAAATCAAT TAAAATGGAC CGATGCCTCA GGTGGGCTGC AAAAAACTTT TAACGGGACT
TATCAAGATA TTTATTATTT CCTTTTACAA CTTCTCCAAC ATAATAAAGT TGCGCTTTAT CCTAAAAATC AATCAGATAA ATCACATGAT
TTCCTCAACG CTCCGGCTGC TACAATGGTT CTAGTGGCAA CAGTTGAAAG CGAAAATACA GAAAAATACC TTAAAATGAA GCTTTTTTCA
AGTGATTATC AAAATGGGAA AAAGGAAATT TTTACCTGAA AAACCAAAAT TGAGAGCCAA TTTCAAAATC TCGATCTAGC TAAAAATCTA
ACTTTAGGTA CAACAAAAAG CAATAATCAA GAAAATATTG ACAAAGAACA ACAAGATGAT AGTAGAAAAC CGACCGGAAT AACACTAAAA
GGTTTTGCCC TCTTTGATAA ACCAAAAGAT AATCAAAAAT ATAATAATAT CCTTGAAAAA TTCCTTAGCG AATATATGGA A
(SEQ ID NO:11)

Fig. 11

MKKNKLKYLI FSIIGISTII SLAVTIPYAL SSQAEKYNLE LNSYNIDLGK AQNLNSRTNF NSAEFDKLVA NLKVKPKFAK RLNAFDALNF
HFDKSYSFDL ADAVDLSSLS QKYPDLSFKL VIPDNKSRFE IKENKLKNIG LNVTNTSKTI NYTAKFDLDF SGQEKSFQFL PENFTGQISL
RNLESLKGKT ATEIAILFYN AWLKRFNKLS DSKIALYETF GEFGGASFSL NSEPIFILPE NFEIKPDLKD NKLVFASIND EKNELVLNMV
LYDKTAKTEK IFPLRFVDLP KTNQKYGEKF LASFLKNYEF NSEISKYLAK NNLDIAQLFS LPSDPKSLDL TKFESWFIQK SVPNTTFFAD
IKGLIPNFET KKAAFLVKKP EKVGQNKNLL TINLKLEGTF LVNDQVPAGL NLTQDKHYTY NFDFDYDATQ EIYSGYFRNA LELFDARTAK
NLDNLKLEVK NDLPVTVFAS TINTKIAHLL NKPLELKGIT KKMSPLFDFL NFSTSKNEKL ETKMAPPNAK MQNVGAILFN EEVKQQESQV
KDQAKQEKSS KDSQSKQTDQ SEKEPKVETK TIQAENGGTY LSKLFENLEK TSFPTNTLLY LSTFYRDKFI LKLELKAEGI TKETLEIKID
KVAPDNKAYQ ALVQSTNTDL FLDWRSNITT TTEKYQNKPV IASISALNNP NLKFKVNPEP SNKSQQKVHL DQAGIYLAEG GISLENLSQE
QAKNLKLDEG KTIFYAFKPT KLSRRSLLRY FLLSASDNSS SKFSLLIEPE ILLTGFNKIG ADFEKVEQNN KNQLKWTDAS GGLQKTFNGT
YQDIYYFLLQ LLQHNKVALY PKNQSDKSHD FLNAPAATMV LVATVESENT EKYLKMKLFS SDYQNGKKEI FTWKTKIESQ FQNLDLAKNL
TLGTTKSNNQ ENIDKEQQDD SRKPTGITLK GFALFDKPKD NQKYNNILEK FLSEYME (SEQ ID NO:12)

Fig. 12

ATGAAGTTAGCAAAATTACTTAAAAAACCTTTTTGATTAATAACAACAATTGCCGGAATTAGTCTTAGTTT
ATCAGCCGCTGTTGGTATAGTTGTCGGAATTAATTCTTATAATAAATCATATTATTCTTATCTAAATGAAA
ATCCAAGTCAGCTAAAAACTACTAAAACAACAAAAATATCCCAGCAAGATTTTGATAAAATAGTCTCAAAT
TTAAAAATTAGGGATAATTTTAAGAAAATATCAGCAAAAACAGCTTTATCAGCGGTAAAAAATGATTTATA
CCGGTATGACTTAGTTCGGGCTTTTGAATTTTCAAGTTTAGAAACTAACAACTATCAAATTAGTTTTGATT
TAGAAAATGCAGTAGTTGATCAAAATTCAATTAAAAATGTGCTAGTTTTTGCAAAATCTGAAAAAGATCAA
GTAACATATTCAAAACAAATTGAACTTAAAGGGTTTGCTCAAGATGATGAAGCTGCAGGCGATCTTGTTAA
ATTCCAAATTGATCAAAGAAAATCCTTTGTTAATCTTTATAAATTTGATTATTCTTTTTCTGAATTTCAAA
GAATTCTTAGCGAAAATTATCGACAAATTAGAAATACAAATTCTTTTACAAGGTTGGCAAATGCTTTGATT
TCCTCAAAAGCGAGTCTTTCACTTTATAATTCCTTAGGGCAACCAGTATTTTTAGATGAAAATTATCGCTT
AGAACCAGTTTTGAATTCAAAAAAAGAATTAAATTTACTAGAAAAAAATAAGAAATTGTATTTAGAACTTA
ATTTAGTTGAAAAAGAGAGCCAAAAGAAAATTAATTTAACACTAGAAATCCGTCCATTATTAACAAATCAA
GAATTTACTAGTGAGTTAAAAACTTTATTTGAATCAAATTTAGACCAAAATCTTAGCCTAAATCTTGAACT
AAAAAATGCTCTTTTCCATGATAGAACCAGTTTTTCTGAGTATTTATATGGAAGTCCACAGCAAAGAACTA
AAACTGATGAAGTAAAACAGAAAGCTAAGGAATTAAAGGATCTTTTTGGTTTTAGATCAGCAAAATTCTGA
CAGGATACAAAATTTGGAACTTTTTATGTAATAATTAAGCCCCAACTTTTAGATCCTGCAAAAATTAGTCA
AGAAGATAAGAAAAAACTTTTAGCTGATAAAAAAATCCGTTTTGAAGTTCTAACTACCTTAAAAAGAAAAG
CGCTTGATCAACAAGATGTTCTCACTGATCTTCCAGTTTTAGTCGATCTAAGCCTTGATTCTAATAAATAC
GAAACAGCCATAAGTCAAATTTTTAATTCAACAAAGACAACCAAAGAATTTAAAATGCAAGAATATGAAGA
TAGAGCGAAGTTATCAACCAAAGAAATCAAAGAAACAATTGATAAATTAGCAAATCTTGCCGCAAAAGTTA
GTAATTTATCCGAACCAAGTGATGAAGTTGTTCGTGCTGTCTATTTATTAAATACAGGGAAATATCTTTTT
GATGATGAGATCCAGCAAGAAAAAACTAATCTTAAAAAAATAATAGAACAAGCCCGAATGAAAGCTGACAC
CAAGAATTTGGCTCCAAAAGTACCTAGTCCTATTCAAAAACCAACTACATCTGCAACTTCTAGTGGAACTA
CTAAGACATCAACAGGGACAGAAAAAAAAGTTTCAGTAAGTGCTTTTTCTGATATAATTAGTATGAAAAAC
CAACCTGAACAAACAACTAAGAACGGTCAGGTCCAAGCTTCTTCTACAAGTCAGAGTCCAAAATCAAGTCT
TAGCCAAAACAGCGGACAAAATTCAATAACTTTAGAAGAAAAATTTGGACATACAATTTGAAAGTTACTAA
ATACATCACAAATTTATAATTTTGAAAACACCCAAGGGCAATATACAATCTCAATAGAGGATGATAAATTA
GTTTTTGACTTTAAGCTTGTATCAAAAGCAGATCGAGCAATTATTTATCAAGGATCTAAAATTAGTCTTGG
TGGTCTAATTAATTCTGATAAGTCTGCCTATGATGAGATTAAACAATTTAGCCCAGATCTTTTCCTTGATG
CAACAATAGGAGAACAATCTGATTATAAAAACAAGCAAAAAAAAGATTATACTTTAAAATCGTTAAGAGAT
TTAATGGGTAATGGCTTTGTTTATAAACCAGAAACTAAATCGAATCCACAAGAAAATGTACTAAAATTACA
AACAGGATCAGAGCAAAAAAAACCTCTACCAGGGCTTAGATCAGGATTAATTTATATTGCATTTACCGTTA
ATAATATCAATAAAAATGATTATAAACCTCATTATCTAATAAGAGATAAAAATGATAAAGGTGTCTTCATT
CAGAGATATCAAGATAAGGAAGAACCAAACGCTTTTGAGATTAGAATTGATTCATATGAGCCTGATGACTT
CAGGGATAAACAATTTCAGGCTGCTGATACGATATTAGATGCAAGTGGTTCAATTGATCCTCGATCAAAGA
AAAAAATTATTCTCCGTCAAAACGCTGATTATTTATTAGTAGTTTATAAGTCAAAAAAAGATATTGTAACA
GAGCTTTATTCACTACCTTCAGCACAAGATAATAACAAAGAAAAGATTGTTAAAATAAAAAATAGAAAATC
ATTTCCCTCTCAAGGTTATACAGTTCAAGGTTCATTATTATATTCTTTATTTAGTCCTAATAAAATTGGAG
ATAGTCAGAAGCCAGCCCAACAACCGCCAGCTGTAAGTATAAAAGCAATAGCATTATTTGATAAAAAATCA
TTTACAAACGATACAGAAAAAATGCGTTTAATAAATAATGCTTTTATTAGTAATTATATAAAACAA (SEQ
ID NO:13)

FIG. 13

MKLAKLLKKPFWLITTIAGISLSLSAAVGIVVGINSYNKSYYSYLNENPSQLKTTKTTKISQQDFDKIVSN
LKIRDNFKKISAKTALSAVKNDLYRYDLVRAFEFSSLETNNYQISFDLENAVVDQNSIKNVLVFAKSEKDQ
VTYSKQIELKGFAQDDEAAGDLVKFQIDQRKSFVNLYKFDYSFSEFQRILSENYRQIRNTNSFTRLANALI
SSKASLSLYNSLGQPVFLDENYRLEPVLNSKKELNLLEKNKKLYLELNLVEKESQKKINLTLEIRPLLTNQ
EFTSELKTLFESNLDQNLSLNLELKNALFHDRTSFSEYLYGSPQQRTKTDEVKQKAKELKDLFGFRSAKFW
QDTKFGTFYVIIKPQLLDPAKISQEDKKKLLADKKIRFEVLTTLKRKALDQQDVLTDLPVLVDLSLDSNKY
ETAISQIFNSTKTTKEFKMQEYEDRAKLSTKEIKETIDKLANLAAKVSNLSEPSDEVVRAVYLLNTGKYLF
DDEIQQEKTNLKKIIEQARMKADTKNLAPKVPSPIQKPTTSATSSGTTKTSTGTEKKVSVSAFSDIISMKN
QPEQTTKNGQVQASSTSQSPKSSLSQNSGQNSITLEEKFGHTIWKLLNTSQIYNFENTQGQYTISIEDDKL
VFDFKLVSKADRAIIYQGSKISLGGLINSDKSAYDEIKQFSPDLFLDATIGEQSDYKNKQKKDYTLKSLRD
LMGNGFVYKPETKSNPQENVLKLQTGSEQKKPLPGLRSGLIYIAFTVNNINKNDYKPHYLIRDKNDKGVFI
QRYQDKEEPNAFEIRIDSYEPDDFRDKQFQAADTILDASGSIDPRSKKKIILRQNADYLLVVYKSKKDIVT
ELYSLPSAQDNNKEKIVKIKNRKSFPSQGYTVQGSLLYSLFSPNKIGDSQKPAQQPPAVSIKAIALFDKKS
FTNDTEKMRLINNAFISNYIKQ (SEQ ID NO: 14)

FIG. 14

GTGATTGAGGGCTTAAAATCAAAGGCAAATACTCAAAAAACAGAAAAAAATAGCCCCACACAACCGAAAAA
ACCAGAGGTTTCACTAGCTAAAACAACAGAAAATTCAGCAAAAACAGTCAAGGTAAGCACTTTTGCAGAAG
AAGCTAAGGGTCAAAGTCAAAGTCAGCAAACACAACCAGTTTCCACTTCATCGCCTCAAACTAGTCAAAAT
TCAGTTTCTAATTCCACAAGCAGTACGAATTTAGCCTTAGAAAATGAAAAATTTGGGACAAGCATTTGAAC
AGCTTTTAATTTCGCTAATATTTATAATCTTGAAAATACAAAAAGCGAATATGAGATCTCAACTTTAGGAA
ATAAGCTATTTTTTGATTTTAAATTAGTTGATAAAACTAATCAAAATCTAATTTTGGCTCAGTCCAAAATT
AGTCTTAATAATATTATTAATTCTAATAAATCTGCCTATGATATAATTAAGAAATTCAATCCCGATGTATT
TCTAGATGGAACAATTAATTATCAAGATCAAGGAAAAGATAAAAAAGAATTTATCCTAAAAGATTTAAGTG
ATAATAAATTAATATTTAAATCAGAAGATGCAATTCAAACTGATCAAGGTTTAGAGCTAAAGAAACCTTTG
AAATTAAGCCCGACAACGAACTCTTCTTCTACTACTTCACAAAAGACTAATAAAAAGGATGATATTGGAGT
GTTTTGACTAGCGCTTCAAGTTAATAATATAACAGATTTCAAAAATCATCATCTAATATCCGATGGAAAAG
GAAATGGAATAATTCTTAACAAATACAAGGTCAAGGATGAAACTGGTTATCAATTAGGACTAGAATATCCT
GGAAGGAATGAAAATAATTTTATTACTGATATTGTTGATCTAGTCGACGGTTTTATCAAATTTATTTTTGG
ATGAAAACAAGACCAAAATAATAGTAGTTTTTTGGACACACCCTCACTTTTAATTGATTTTAACAAGTATA
AAAACAAAAAAAAATACTGAATTTATCAAGGCGAATACAAAAATTCTTTTAGAGGTTGTAGAAAACAATGAT
CGACTTTCTGTTTCAGTATTTTCTTCTCAAGCAGGAAAAAATCATAAACAAATTATAGAAAATAGAATGCA
TAGAAGTTTACATTATAAAAAAGCAGACAAAGCCAAAGAAGGTGTAAGCCCAATCCCAAGTTTTACTGATA
TTTTAAATGAATTACAAATTGGAGCTACTGATAGCGATCCAAAAACTCAAAAGGCACCAGTAACATTCAAA
GCGTTTATGATGTCAAATGATAAAAATCTAGTATTTGGATCAAACATTAATAATCAAGAAATTCGCCAAGC
GCTTATTGACGCTTATATAGTTGATAAGAAT (SEQ ID NO: 15)

FIG. 15

VIEGLKSKANTQKTEKNSPTQPKKPEVSLAKTTENSAKTVKVSTFAEEAKGQSQSQQTQPVSTSSPQTSQN
SVSNSTSSTNLALENEKFGTSIWTAFNFANIYNLENTKSEYEISTLGNKLFFDFKLVDKTNQNLILAQSKI
SLNNIINSNKSAYDIIKKFNPDVFLDGTINYQDQGKDKKEFILKDLSDNKLIFKSEDAIQTDQGLELKKPL
KLSPTTNSSSTTSQKTNKKDDIGVFWLALQVNNITDFKNHHLISDGKGNGIILNKYKVKDETGYQLGLEYP
GRNENNFITDIVDLVDGFIKFIFGWKQDQNNSSFLDTPSLLIDFNKYKNKKNTEFIKANTKILLEVVENND
RLSVSVFSSQAGKNHKQIIENRMHRSLHYKKADKAKEGVSPIPSFTDILNELQIGATDSDPKTQKAPVTFK
AFMMSNDKNLVFGSNINNQEIRQALIDAYIVDKN (SEQ ID NO: 16)

FIG. 16

ATGAAGTTAGCAAAATTACTTAAAAAACCTTTTTGATTAATAACAACAATTGCCGGAATTAGTCTTAGTTT
ATCAGCCGCTGTTGGTACAGTTGTCGGAATTAATTCTTATAATAAATCATATTATTCTTATCTAAATCAGA
TCCCGAGTCAGCTAAAAGTAGCAAAAAATGCTAAAATTAGTCAGGAAAAATTTGATTCAATTGTTTTAAAT
CTTAAAATTAAAGATAATTTTAAAAAATGATCGGCAAAAACAGTTTTAACTGCTGCCAAAAGTGATCTTTA
TCGTTATAATCTTGTTTCTGCTTTTGATTTAAGTGAACTAATAAACAATGATTATTTAGTAAGTTTTGATC
TTGAAAATGCAGTAGTTGATCAAAATTCAATTAAAAATGTTGTTATTTATGCAAAATCTGATAAGGATCAA
ATAACTTATTCAAAACAAATTGTACTTAAAGGCTTTGGAAATACAGAACAAGCGAGAACTAATTTTGATTT
TAGCCAAATTGATTCAAGCAAGTCTTTTGTTGATCTTTCAAGGGCAAATCTAACTTTGACGGAATTCCAAA
TTTTACTTGCCCAAAATTTTGAAAATGAAAGAGGAAGTAATTGATTTTCACGACTTGAAAGAGCTTTGGTT
GCATCAAAAGCGAGTCTTTCACTTTATAATTCCTTAGGAGAACCCGTATTTTTAGGCCCAGATTATCAATT
AGACCCAGTTTTGGACCGAAAAAAATTATTAACTTTGTTAAATAAAGATGGAAAATTAGTTCTTGGACTTA
ATTTAGTGCAAATTTCAACTAAAAAAACTATGAATTTAAATCTTGAAGTTCGCGGCGCGATTTCAAATCAG
GAAATTTCTAAAATTCTAAAATCCTGACTTGAAACAAATCTTCAAGGCAAATTAAAAACCAAAGATGATTT
GCAAATGGCACTAGTAAAAGATAAAATTAGCCTCTCTGATTATTGATATGGATCTCCGAATTCAAAAGTAA
ATACATCCCAAATTTTAACAAAAAGTAAAGAATTTAAAGATCTTTTTGATTTAAGTGAGACAAATTTTTTT
CTTAATACCAAAATCGGAACTGTCTATTTAAGTATTATTCCCAAACTTTTAGATCCAAGTCAGATTTCTGT
TGTTGATAAGAAAAAACTAGTTGAAAATCAAAAAATTCGCTTTGAAATTACTGCTTCTTTAAAACGAAAAG
CTATTGATAAAAAATTTATCATCCAGGATCTTCCAGTTTTTGTTGATCTAAAAGTTGATTTTAATAAATAC
CAAGCCGCTGTTGCCCAAATGTTTGGAACGATAAAAGCAGTTAAAGAATTTTCAATGCCTGAAGATCAAGA
TGCA (SEQ ID NO: 17)

FIG. 17

MKLAKLLKKPFWLITTIAGISLSLSAAVGTVVGINSYNKSYYSYLNQIPSQLKVAKNAKISQEKFDSIVLN
LKIKDNFKKWSAKTVLTAAKSDLYRYNLVSAFDLSELINNDYLVSFDLENAVVDQNSIKNVVIYAKSDKDQ
ITYSKQIVLKGFGNTEQARTNFDFSQIDSSKSFVDLSRANLTLTEFQILLAQNFENERGSNWFSRLERALV
ASKASLSLYNSLGEPVFLGPDYQLDPVLDRKKLLTLLNKDGKLVLGLNLVQISTKKTMNLNLEVRGAISNQ
EISKILKSWLETNLQGKLKTKDDLQMALVKDKISLSDYWYGSPNSKVNTSQILTKSKEFKDLFDLSETNFF
LNTKIGTVYLSIIPKLLDPSQISVVDKKKLVENQKIRFEITASLKRKAIDKKFIIQDLPVFVDLKVDFNKY
QAAVAQMFGTIKAVKEFSMPEDQDA (SEQ ID NO: 18)

FIG. 18

ATGAAAAACAAAAAATCAACATTACTATTAGCCACAGCGGCGGCAATTATTGGTTCAACTGTTTTTGGGAC
AGTTGTTGGCTTGGCTTCAAAAGTTAAATATCGGGGTGTAAATCCAACTCAAGGAGTAATATCTCAATTAG
GACTGATTGATTCTGTTGCATTTAAACCTTCGATTGCAAATTTTACAAGCGATTATCAAAGTGTTAAAAAA
GCACTTTTAAATGGGAAAACCTTTGATCCAAAAAGTTCAGAATTTACTGATTTTGTCTCAAAATTTGACTT
TTTGACTAATAATGGGAGAACCGTTTTGGAGATCCCGAAAAAATATCAGGTGGTTATCTCGGAATTTAGCC
CCGAGGATGATAAAGAACGTTTTCGTCTTGGATTTCATCTAAAAGAAAAACTTGAAGATGGAAATATAGCT
CAATCAGCAACTAAATTTATTTATCTTTTACCACTTGATATGCCCAAAGCGGCCCTGGGTCAATATTCTTA
TATCGTTGATAAAAATTTTAATAATTTAATTATCCATCCTTTATCTAATTTTTCTGCTCAATCAATAAAGC
CGCTTGCACTGACCCGTTCAAGTGATTTTATAGCAAAACTTAATCAGTTTAAAAATCAGGACGAACTTTGA
GTTTATCTTGAAAAATTCTTTGATCTTGAAGCTCTAAAAGCAAATATTCGTTTGCAGACAGCCGATTTTAG
TTTTGAAAAAGGCAATTTAGTTGATCCTTTTGTTTATTCTTTTATTAGAAATCCGCAAAATGGAAAAGAAT
GAGCTAGTGATCTTAATCAAGATCAAAAAACCGTCAGACTTTATCTTCGAACCGAATTTAGTCCTCAGGCT
AAAACCATTTTAAAAGACTATAAATACAAAGATGAGACTTTCTTAAGTAGTATCGATTTAAAAGCAAGTAA
TGGAACTAGTTTATTTGCTAATGAAAATGATCTAAAAGATCAATTAGATGTTGATCTTTTAGATGTCTCTG
ATTATTTTGGAGGCCAATCAGAGACAATTACTAGTAATTCCCAAGTTAAACCTGTCCCTGCTAGTGAGAGA
TCTTTAAAAGATCGGGTTAAATTTAAAAAAGATCAGCAAAAACCAAGAATTGAGAAATTTAGTTTATATGA
ATATGATGCTCTAAGTTTTTATTCCCAACTTCAGGAATTAGTTTCTAAACCTAATTCAATTAAAGATTTAG
TTAATGCAACTTTAGCTCGTAATCTTCGGTTTTCATTAGGAAAATATAATTTTCTTTTTGATGATTTAGCC
AGTCATCTTGATTATACTTTTTTAGTTTCAAAAGCAAAAATTAAACAAAGTTCAATTACAAAAAAAATTATT
CATTGAATTACCAATCAAAATTAGTCTTAAATCTTCAATTTTAGGTGATCAAGAACCTAATATTAAAACTT
TATTCGAAAAAGAAGTAACTTTTAAATTAGATAACTTCCGTGATGTTGAAATCGAAAAAGCTTTTGGACTT
TTATATCCAGGTGTTAATGAAGAACTTGAACAAGCCCGAAGAGAGCAAAGAGCAAGTTTGGAAAAAGAAAA
AGCGAAAAAGGGTCTTAAAGAATTTAGCCAGCAAAAAGATGAGAATTTAAAAGCAATAAATAATCAAGATG
GTCTTGAAGAAGATGATAATATTACTGAAAGACTTCCTGAGAATTCCCCGATTCAATATCAGCAAGAAAAG
GCCGGTTTAGGTTCAAGTCCGGATAAACCTTATATGATAAAGGATGTCCAAAATCAACGTTATTATCTAGC
AAAATCACAAATTCAAGAACTAATTAAGGCCAAAGATTATACCAAATTAGCCAAACTTTTATCCAATAGAC
ATACTTATAATATTTCTTTAAGATTAAAAGAACAACTTTTTGAAGTAAATCCAAGAATTCCAAGCTCTAGA
GATATAGAAAATGCAAAATTTGTTCTAGATAAAACCGAAAAAAATAAATACTGGCAGATTTATTCAAGTGC
TTCTCCTGCTTTCCAAAATAAATGATCACTTTTTGGATATTACCGTTATTTATTAGGTCTTGATCCAAAAC
AAACAATCCACGAATTAGTAAAATTAGGACAAAAAGCGGGTCTTCAATTTGAAGGATATGAAAATCTTCCT
TCTGATTTCAATCTTGAAGATCTTAAGAATATTAGGATTAAAACACCTTTATTTAGTCAAAAAGATAATTT
CAAATTATCTTTACTTGATTTTAATAATTATTATGATGGTGAAATTAAAGCCCCAGAATTTGGTCTTCCTT
TATTTTTACCAAAAGAATTAAGAAAAAATAGTTCAAATATTGGTAGTTCTCAAAACTCTAATAGCCCTTGA
GAACAAGAAATTATTAGCCAATTTAAAGATCAAAATCTATCTAATCAGGATCAGTTAGCCCAGTTTAGTAC
TAAAATCTGGGAAAAAATCATTGGTGATGAAAACGAATTTGATCAAAATAACAGGCTTCAGTATAAACTTT
TAAAAGATCTTCAAGAATCTTGAATTAACAAAACTCGCGATAATCTTTATTGGACTTATCTAGGTGATAAA
CTTAAAGTTAAACCAAAAAATAATTTAGATGCTAAATTTAGACAAATTTCCAATTTACAAGAGCTTTTAAC
TGCTTTTTATACCTCAGCTGCTCTTTCTAATAACTGAAATTATTATCAAGATTCAGGGGCAAAGTCAACTA
TTATTTTTGAAGAAATAGCTGAGCTAGATCCAAAAGTAAAAGAAAAAGTAGGAGCTGATGTTTATCAATTA
AAATTCCATTATGCAATCGGTTTTGATGATAATGCTGGCAAGTTTAATCAAGAAGTAATTCGTTCTTCAAG
TAGAACAATTTATCTTAAAACCTCAGGGAAATCCAAATTAGAAGCAGATACAATTGATCAACTTAATCAAG
CAGTTGAAAATGCACCTTTAGGTCTTCAAAGTTTTTATCTTGATACTGAAAGATTTGGGGTTTTCCAAAAA
TTAGCAACTTCCTTAGCAGTTCAACATAAACAAAAAGAAAAACCACTACCTAAAAAACTAAATAATGATGG
CTATACTTTAATTCATGATAAACTTAAAAAACCAGTAATTCCCCAAATTAGTTCAAGTCCCGAAAAAGATT
GATTTGAAGGTAAATTAAATCAAAACGGGCAAAGCCAAAATGTAAATGTCTCAACTTTTGGTTCAATAATC
GAGTCCCCTTATTTTAGTACTAATTTCCAAGAAGAAGCTGATTTAGACCAAGAAGGACAAGATGATTCAAA
ACAAGGAAATAAGAGCCTAGATAATCAAGAAGCAGGTCTTTTAAAACAAAAACTGGCAATTTTATTAGGGA
ATCAATTTATCCAATATTATCAACAAAATGATAAAGAAATTGAATTCGAGATTATCAATGTTGAGAAAGTT
TCAGAGCTTAGTTTCCGCGTTGAATTTAAATTAGCAAAAACTCTTGAAGACAACGGAAAAACTATTCGAGT
TTTATCAGATGAGACAATGTCATTAATTGTTAATACTACAATTGAAAAAGCACCAGAAATGAGTGCTGCTC
CCGAAGTATTCGATACTAAATGGGTTGAGCAATATGATCCAAGAACCCCGCTTGCGGCTAAGACAAAGTTT
GTCTTAAAATTCAAAGATCAAATACCAGTTGATGCCAGCGGAAATATTTCTGATAAATGACTAGCAAGTAT
TCCTTTGGTGATTCACCAGCAAATGTTGCGTCTTAGCCCGGTAGTTAAAACAATAAGAGAGCTTGGTCTAA
AAACTGAACAACAACAACAACAACAACAACAACAACAAAAGAAAGCTGTTAGAAAAGAAGAAGAACTGGAA

FIG. 19 (1 of 2)

ACCTATAATCCAAAAGACGAGTTTAATATTCTTAATCCTTTAACAAAAGCTCACCGTCTTACCTTATCAAA
TTTAGTAAATAATGATCCAAATTATAAAATTGAAGATTTAAAAGTAATCAAAAATGAAGCAGGTGATCATC
AATTAGAATTTTCTCTAAGAGCTAATAATATCAAAAGATTAATGAATACACCAATTACTTTTGCTGATTAT
AATCCCTTTTTCTATTTTAATGAGGACTGAAGAAATATAGATAAATATTTAAATAATAAAGGAAATGTGAG
TTCTCAACAACAACAACAACAACAACAACAACCAGGCGGGGGTAATCAAGGCTCGGGTCTAATCCAAAGAC
TTAATAAAAATATTAAGCCCGAAACTTTTACCCCCGCACTCATAGCTCTTAAACGAGATAATAATACTAAT
CTTTCTAACTATTCTGATAAAATAATAATGATCAAACCAAAATATTTGGTTGAACGATCAATTGGTGTTCC
CTGATCAACCGGCCTTGATGGTTATATTGGTTCAGAACAACTCAAGGGCGGAACTTCCTCAAACGGTCAAA
AGCGATTTAAGCAAGATTTTATTCAGGCTTTAGGTCTTAAAAACACTGAATATCATGGTAAACTAGGTCTT
TCAATTAGAATTTTTGATCCTGGAAATGAACTAGCAAAAATTAAGGATGCTTCAAATAAAAAAGGGGAAGA
AAAACTGTTAAAATCATATGATTTATTTAAAAACTATTTAAATGAATATGAGAAAAAATCCCCTAAAATTG
CTAAGGGATGAACAAATATTCATCCTGATCAAAAAGAATATCCAAATCCAAATCAAAAACTACCTGAAAAT
TATCTTAACCTAGTTTTAAATCAACCTTGAAAGGTTACTTTATATAATTCAAGTGATTTTATTACTAATTT
ATTTGTTGAACCTGAAGGCTCAGATCGGGGATCTGGAGCAAAATTAAAACAAGTAATCCAGAAGCAAGTTA
ATAATAACTATGCTGACTGGGGGTCTGCATATCTCACGTTCTGGTATGATAAAGATATCATTACCAATCAG
CCAAATGTTATAACTGCTAACATTGCTGATGTCTTTATTAAAGATGTAAAGGAACTTGAAGATAATACAAA
ACTAATTGCTCCAAATATTACTCAATGATGGCCAAATATTAGCGGCTCAAAGGAGAAATTTTATAAGCCAA
CAGTGTTTTTTGGTAATTGAGAAAATGAAAACAGCAATATGAATTCCCAGGGGCAGACCCCTACCTGGGAG
AAGATCAGAGAAGGATTTGCTCTCCAAGCGCTTAAATCCAGCTTTGATCAAAAAACAAGGACATTTGTCCT
TACAACAAATGCTCCTTTACCTTTATGAAAATACGGACCATTAGGTTTCCAAAATGGGCCGAATTTCAAAA
CACAAGATTGAAGGCTTGTTTTCCAAAATGATGATAACCAAATAGCCGCGCTAAGAGTCCAGGAGCAAGAT
CGCCCAGAAAAATCAAGCGAAGATAAAGACAAGCAAAAATGGATTAAATTTAAAGTTGTTATCCCTGAAGA
AATGTTTAATTCCGGTAATATACGTTTTGTTGGGGTAATGCAGATCCAAGGTCCTAATACTTTATGACTTC
CAGTGATTAATTCTTCGGTTATCTATGACTTCTATCGCGGAACAGGAGATTCTAACGATGTCGCCAATCTT
AATGTAGCTCCTTGACAGGTTAAAACAATCGCATTTACAAATAACGCCTTTAATAATGTTTTCAAAGAGTT
TAATATCTCTAAAAAAATAGTAGAATAA (SEQ ID NO:19)

FIG. 19 (2 of 2)

MKNKKSTLLLATAAAIIGSTVFGTVVGLASKVKYRGVNPTQGVISQLGLIDSVAFKPSIANFTSDYQSVKK
ALLNGKTFDPKSSEFTDFVSKFDFLTNNGRTVLEIPKKYQVVISEFSPEDDKERFRLGFHLKEKLEDGNIA
QSATKFIYLLPLDMPKAALGQYSYIVDKNFNNLIIHPLSNFSAQSIKPLALTRSSDFIAKLNQFKNQDELW
VYLEKFFDLEALKANIRLQTADFSFEKGNLVDPFVYSFIRNPQNGKEWASDLNQDQKTVRLYLRTEFSPQA
KTILKDYKYKDETFLSSIDLKASNGTSLFANENDLKDQLDVDLLDVSDYFGGQSETITSNSQVKPVPASER
SLKDRVKFKKDQQKPRIEKFSLYEYDALSFYSQLQELVSKPNSIKDLVNATLARNLRFSLGKYNFLFDDLA
SHLDYTFLVSKAKIKQSSITKKLFIELPIKISLKSSILGDQEPNIKTLFEKEVTFKLDNFRDVEIEKAFGL
LYPGVNEELEQARREQRASLEKEKAKKGLKEFSQQKDENLKAINNQDGLEEDDNITERLPENSPIQYQQEK
AGLGSSPDKPYMIKDVQNQRYYLAKSQIQELIKAKDYTKLAKLLSNRHTYNISLRLKEQLFEVNPRIPSSR
DIENAKFVLDKTEKNKYWQIYSSASPAFQNKWSLFGYYRYLLGLDPKQTIHELVKLGQKAGLQFEGYENLP
SDFNLEDLKNIRIKTPLFSQKDNFKLSLLDFNNYYDGEIKAPEFGLPLFLPKELRKNSSNIGSSQNSNSPW
EQEIISQFKDQNLSNQDQLAQFSTKIWEKIIGDENEFDQNNRLQYKLLKDLQESWINKTRDNLYWTYLGDK
LKVKPKNNLDAKFRQISNLQELLTAFYTSAALSNNWNYYQDSGAKSTIIFEEIAELDPKVKEKVGADVYQL
KFHYAIGFDDNAGKFNQEVIRSSSRTIYLKTSGKSKLEADTIDQLNQAVENAPLGLQSFYLDTERFGVFQK
LATSLAVQHKQKEKPLPKKLNNDGYTLIHDKLKKPVIPQISSSPEKDWFEGKLNQNGQSQNVNVSTFGSII
ESPYFSTNFQEEADLDQEGQDDSKQGNKSLDNQEAGLLKQKLAILLGNQFIQYYQQNDKEIEFEIINVEKV
SELSFRVEFKLAKTLEDNGKTIRVLSDETMSLIVNTTIEKAPEMSAAPEVFDTKWVEQYDPRTPLAAKTKF
VLKFKDQIPVDASGNISDKWLASIPLVIHQQMLRLSPVVKTIRELGLKTEQQQQQQQQQQKKAVRKEEELE
TYNPKDEFNILNPLTKAHRLTLSNLVNNDPNYKIEDLKVIKNEAGDHQLEFSLRANNIKRLMNTPITFADY
NPFFYFNEDWRNIDKYLNNKGNVSSQQQQQQQQQQPGGNQGSGLIQRLNKNIKPETFTPALIALKRDNNTN
LSNYSDKIIMIKPKYLVERSIGVPWSTGLDGYIGSEQLKGGTSSNGQKRFKQDFIQALGLKNTEYHGKLGL
SIRIFDPGNELAKIKDASNKKGEEKLLKSYDLFKNYLNEYEKKSPKIAKGWTNIHPDQKEYPNPNQKLPEN
YLNLVLNQPWKVTLYNSSDFITNLFVEPEGSDRGSGAKLKQVIQKQVNNNYADWGSAYLTFWYDKDIITNQ
PNVITANIADVFIKDVKELEDNTKLIAPNITQWWPNISGSKEKFYKPTVFFGNWENENSNMNSQGQTPTWE
KIREGFALQALKSSFDQKTRTFVLTTNAPLPLWKYGPLGFQNGPNFKTQDWRLVFQNDDNQIAALRVQEQD
RPEKSSEDKDKQKWIKFKVVIPEEMFNSGNIRFVGVMQIQGPNTLWLPVINSSVIYDFYRGTGDSNDVANL
NVAPWQVKTIAFTNNAFNNVFKEFNISKKIVE (SEQ ID NO: 20)

FIG. 20

IMMUNOGENIC *MYCOPLASMA HYOPNEUMONIAE* POLYPEPTIDES

CROSS REFERENCE TO RELATED APPLICATIONS

This application claims priority under 35 U.S.C. §119(e) of U.S. application No. 60/392,632, filed Jun. 28, 2002.

BACKGROUND

1. Technical Field

The invention relates to methods and materials involved in protecting an animal against enzootic pneumonia.

2. Background Information

Enzootic pneumonia in swine, also called mycoplasmal pneumonia, is caused by *Mycoplasma hyopneumoniae*. The disease is chronic and non-fatal, affecting pigs of all ages. Although infected pigs show only mild symptoms of coughs and fever, the disease has significant economic impact due to reduced feed efficiency and reduced weight gain. Enzootic pneumonia is transmitted by airborne organisms expelled from the lungs of infected pigs. The primary infection by *M. hyopneumoniae* may be followed by a secondary infection of other *Mycoplasma* species, e.g., *Mycoplasma hyorhinis* and *Mycoplasma flocculare*, as well as other bacterial pathogens.

*M. hyopneumoniae* infects the respiratory tracts of pigs, colonizing the tracheae, bronchi, and bronchioles. The pathogen produces a ciliostatic factor that causes the cilia lining the respiratory passages to stop beating. Eventually, the cilia degenerate, leaving pigs prone to infection by secondary pathogens. Characteristic lesions of purple to gray areas of consolidation are observed in infected pigs. Surveys of slaughtered pigs revealed lesions in 30% to 80%. Results from 37 herds in 13 states indicated that 99% of the herds had pigs with pneumonia lesions typical of enzootic pneumonia. Therefore, there is a need for effective preventative and treatment measures.

Mycoplasmas vary their surface structure by a complex series of genetic events to present a structural mosaic to the host immune system. Phase switching of surface molecules occurs through a variety of mechanisms such as changes in the number of repetitive units during DNA replication, genomic inversions, transposition events, and/or gene conversion. See, for example, Zhang and Wise, 1997, *Mol. Microbiol.,* 25:859-69; Theiss and Wise, 1997, *J. Bacteriol.,* 179:4013-22; Sachse et al., 2000, *Infect. Immun.,* 68:680-7; Dybvig and Uy, 1994, *Mol. Microbiol.,* 12:547-60; and Lysnyansky et al., 1996, *J. Bacteriol.,* 178:5395-5401. All of the identified phase variable and phase switching genes in mycoplasmas that code for surface proteins are lipoproteins.

SUMMARY

The invention provides materials and methods for protecting an animal from enzootic pneumonia. The invention is based on the discovery of *Mycoplasma hyopneumoniae* nucleic acids that encode cell surface polypeptides that can be used for inducing a protective immune response in an animal susceptible to pneumonia. More specifically, the invention provides purified immunogenic polypeptides of these polypeptides for used to as antigens for illiciting an immune response in an animal, e.g. a pig. In addition, the invention also provides isolated nucleic acids encoding these immunogenic polypeptides for use in generating an immune response in an animal. Purified polypeptides and isolated nucleic acids of the invention can be combined with pharmaceutically acceptable carriers for introducing into an animal. The invention also provides materials and methods for determining whether an animal has an antibody reactive to the polypeptides of the invention.

In one aspect, the invention provides a purified immunogenic polypeptide, the amino acid sequence of which comprises at least eight consecutive residues of a sequence selected from the group consisting of SEQ ID NOs:2, 4, 6, 8, 10, 12, 14, 16, 18, and 20. Specifically, the invention provides an immunogenic polypeptide of the invention, the amino acid sequence of which comprises at least eight consecutive residues of SEQ ID NO: 2; an immunogenic polypeptide of the invention, the amino acid sequence of which comprises at least eight consecutive residues of SEQ ID NO:4; an immunogenic polypeptide of the invention, the amino acid sequence of which comprises at least eight consecutive residues of SEQ ID NO:6; an immunogenic polypeptide of the invention, the amino acid sequence of which comprises at least eight consecutive residues of SEQ ID NO:8; an immunogenic polypeptide of the invention, the amino acid sequence of which comprises at least eight consecutive residues of SEQ ID NO:10; an immunogenic polypeptide of the invention, the amino acid sequence of which comprises at least eight consecutive residues of SEQ ID NO:12; an immunogenic polypeptide of the invention, the amino acid sequence of which comprises at least eight consecutive residues of SEQ ID NO:14; an immunogenic polypeptide of the invention, the amino acid sequence of which comprises at least eight consecutive residues of SEQ ID NO:16; an immunogenic polypeptide of the invention, the amino acid sequence of which comprises at least eight consecutive residues of SEQ ID NO:18; an immunogenic polypeptide of the invention, the amino acid sequence of which comprises at least eight consecutive residues of SEQ ID NO: 20.

In another aspect, the invention provides mutants of the above-described immunogenic polypeptides, wherein such mutant polypeptides retain immunogenicity.

Generally, immunogenic polypeptides and immunogenic mutant polypeptides of the invention include at least 8 consecutive residues (e.g., at least 10, 12, 15, 20, or 25) of SEQ ID NOs:2, 4, 6, 8, 10, 12, 14, 16, 18, or 20.

In another aspect, the invention provides a composition that includes one or more of the above-described immunogenic polypeptides or immunogenic mutant polypeptides.

In one aspect, the invention provides a method of eliciting an immune response in an animal. Such a method includes introducing a composition comprising the above-described immunogenic polypeptides or immunogenic mutant polypeptides into the animal. Such a composition can be administered orally, intranasally, intraperitoneally, intramuscularly, subcutaneously, or intravenously. A representative animal into which the compositions of the invention can be introduced is a swine.

In another aspect, the invention provides an isolated nucleic acid comprising a nucleotide sequence that encodes an immunogenic polypeptide, the amino acid sequence of which comprises at least eight consecutive residues of a sequence such as SEQ ID NOs: 2, 4, 6, 8, 10, 12, 14, 16, 18, or 20. The invention also features mutants of nucleic acids that encode an immunogenic polypeptide. Representative nucleic acids encoding such immunogenic polypeptides have a nucleotide sequence as shown in SEQ ID NOs: 1, 3, 5, 7, 9, 11, 13, 15, 17, and 19, respectively.

Specifically, the invention provides a nucleic acid having a nucleotide sequence encoding an immunogenic polypeptide, the amino acid sequence of which comprises at least eight consecutive residues of SEQ ID NO:2. A representative nucleic acid encoding such a polypeptide has the nucleotide sequence of SEQ ID NO:1.

Specifically, the invention provides a nucleic acid having a nucleotide sequence encoding an immunogenic polypeptide, the amino acid sequence of which comprises at least eight consecutive residues of SEQ ID NO:4. A representative nucleic acid encoding such a polypeptide has the nucleotide sequence of SEQ ID NO:3.

Specifically, the invention provides a nucleic acid having a nucleotide sequence encoding an immunogenic polypeptide, the amino acid sequence of which comprises at least eight consecutive residues of SEQ ID NO:6. A representative nucleic acid encoding such a polypeptide has the nucleotide sequence of SEQ ID NO:5.

Specifically, the invention provides a nucleic acid having a nucleotide sequence encoding an immunogenic polypeptide, the amino acid sequence of which comprises at least eight consecutive residues of SEQ ID NO:8. A representative nucleic acid encoding such a polypeptide has the nucleotide sequence of SEQ ID NO:7.

Specifically, the invention provides a nucleic acid having a nucleotide sequence encoding an immunogenic polypeptide, the amino acid sequence of which comprises at least eight consecutive residues of SEQ ID NO:10. A representative nucleic acid encoding such a polypeptide has the nucleotide sequence of SEQ ID NO:9.

Specifically, the invention provides a nucleic acid having a nucleotide sequence encoding an immunogenic polypeptide, the amino acid sequence of which comprises at least eight consecutive residues of SEQ ID NO:12. A representative nucleic acid encoding such a polypeptide has the nucleotide sequence of SEQ ID NO:11.

Specifically, the invention provides a nucleic acid having a nucleotide sequence encoding an immunogenic polypeptide, the amino acid sequence of which comprises at least eight consecutive residues of SEQ ID NO:14. A representative nucleic acid encoding such a polypeptide has the nucleotide sequence of SEQ ID NO:13.

Specifically, the invention provides a nucleic acid having a nucleotide sequence encoding an immunogenic polypeptide, the amino acid sequence of which comprises at least eight consecutive residues of SEQ ID NO:16. A representative nucleic acid encoding such a polypeptide has the nucleotide sequence of SEQ ID NO:15.

Specifically, the invention provides a nucleic acid having a nucleotide sequence encoding an immunogenic polypeptide, the amino acid sequence of which comprises at least eight consecutive residues of SEQ ID NO:18. A representative nucleic acid encoding such a polypeptide has the nucleotide sequence of SEQ ID NO:17.

Specifically, the invention provides a nucleic acid having a nucleotide sequence encoding an immunogenic polypeptide, the amino acid sequence of which comprises at least eight consecutive residues of SEQ ID NO:20. A representative nucleic acid encoding such a polypeptide has the nucleotide sequence of SEQ ID NO:19.

The invention also provides a vector containing a nucleic acid of the invention. A vector can further include an expression control sequence operably linked to the nucleic acid. The invention additionally provides host cells comprising such vectors. The invention further provides a composition that includes such vectors and a pharmaceutically acceptable carrier.

In yet another aspect, the invention provides a method of eliciting an immune response in an animal. Such a method includes introducing a composition of the invention into the animal. Such compositions can be administered orally, intranasally, intraperitoneally, intramuscularly, subcutaneously, or intravenously. Generally, the animal is a swine.

In still yet another aspect, the invention provides a method of determining whether or not an animal has an antibody reactive to an immunogenic polypeptide of the invention, the method comprising: providing a test sample from the animal; contacting the test sample with the immunogenic polypeptide under conditions permissible for specific binding of the immunogenic polypeptide with the antibody; and detecting the presence or absence of the specific binding. Typically, the presence of specific binding indicates that the animal has the antibody, and the absence of specific binding indicates that the animal does not have the antibody.

Generally, an appropriate test sample is a biological fluid such as blood, nasal fluid, throat fluid, or lung fluid. In some embodiments, the immunogenic polypeptide is attached to a solid support such as a microtiter plate, or polystyrene beads. In some embodiments, the immunogenic polypeptide is labeled. By way of example, the detecting step can be by radioimmunoassay (RIA), enzyme immunoassay (EIA), or enzyme-linked immunosorbent assay (ELISA).

In another aspect, the invention provides a diagnostic kit for detecting the presence of an antibody in a test sample, wherein such an antibody is reactive to an immunogenic polypeptide of the invention. Such a kit can include one or more of the immunogenic polypeptides of the invention.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 is the nucleic acid sequence encoding C2-mhp210 (SEQ ID NO:1), a P102 paralog from *M. hyopneumoniae* strain 232.

FIG. 2 is the polypeptide sequence of C2-MHP210 (SEQ ID NO:2) from *M. hyopneumoniae* strain 232.

FIG. 3 is the nucleic acid sequence encoding C2-mhp211 (SEQ ID NO:3) from *M. hyopneumoniae* strain 232.

FIG. 4 is the polypeptide sequence of C2-MHP211 (SEQ ID NO:4) from *M. hyopneumoniae* strain 232.

FIG. 5 is the nucleic acid sequence encoding C27-mhp348 (SEQ ID NO:5), a P102 paralog from *M. hyopneumoniae* strain 232.

FIG. 6 is the polypeptide sequence of C27-MHP348 (SEQ ID NO:6) from *M. hyopneumoniae* strain 232.

FIG. 7 is the nucleic acid sequence encoding C28-mhp545 (SEQ ID NO:7) from *M. hyopneumoniae* strain 232.

FIG. 8 is the polypeptide sequence of C28-MHP545 (SEQ ID NO:8) from *M. hyopneumoniae* strain 232.

FIG. 9 is the nucleic acid sequence encoding C28-mhp662 (SEQ ID NO:9) from *M. hyopneumoniae* strain 232.

FIG. 10 is the polypeptide sequence of C28-MHP662 (SEQ ID NO:10) from *M. hyopneumoniae* strain 232.

FIG. 11 is the nucleic acid sequence encoding C28-mhp663 (SEQ ID NO:11), a P102 paralog from *M. hyopneumoniae* strain 232.

FIG. 12 is the polypeptide sequence of C28-MHP663 (SEQ ID NO:12) from *M. hyopneumoniae* strain 232.

FIG. 13 is the nucleic acid sequence encoding C2-mhp036 (SEQ ID NO: 13), a P102 paralog from *M. hyopneumoniae* strain 232.

FIG. 14 is the polypeptide sequence of C2-MPH036 (SEQ ID NO:14) from *M. hyopneumoniae* strain 232.

FIG. 15 is the nucleic acid sequence encoding C2-mhp033 (SEQ ID NO: 15), a partial paralog of P102 from *M. hyopneumoniae* strain 232.

FIG. 16 is the polypeptide sequence of C2-MHP033 (SEQ ID NO:16) from *M. hyopneumoniae* strain 232.

FIG. 17 is the nucleic acid sequence encoding C2-mhp034 (SEQ ID NO: 17), a partial paralog of P102 from *M. hyopneumoniae* strain 232.

FIG. 18 is the polypeptide sequence of C2-MHP034 (SEQ ID NO:18) from *M. hyopneumoniae* strain 232.

FIG. 19 is the nucleic acid sequence encoding C28-mhp545 (SEQ ID NO:19) from *M. hyopneumoniae* strain J.

FIG. 20 is the polypeptide sequence of C28-MHP545 (SEQ ID NO:20) from *M. hyopneumoniae* strain J.

DETAILED DESCRIPTION

Figure 21:
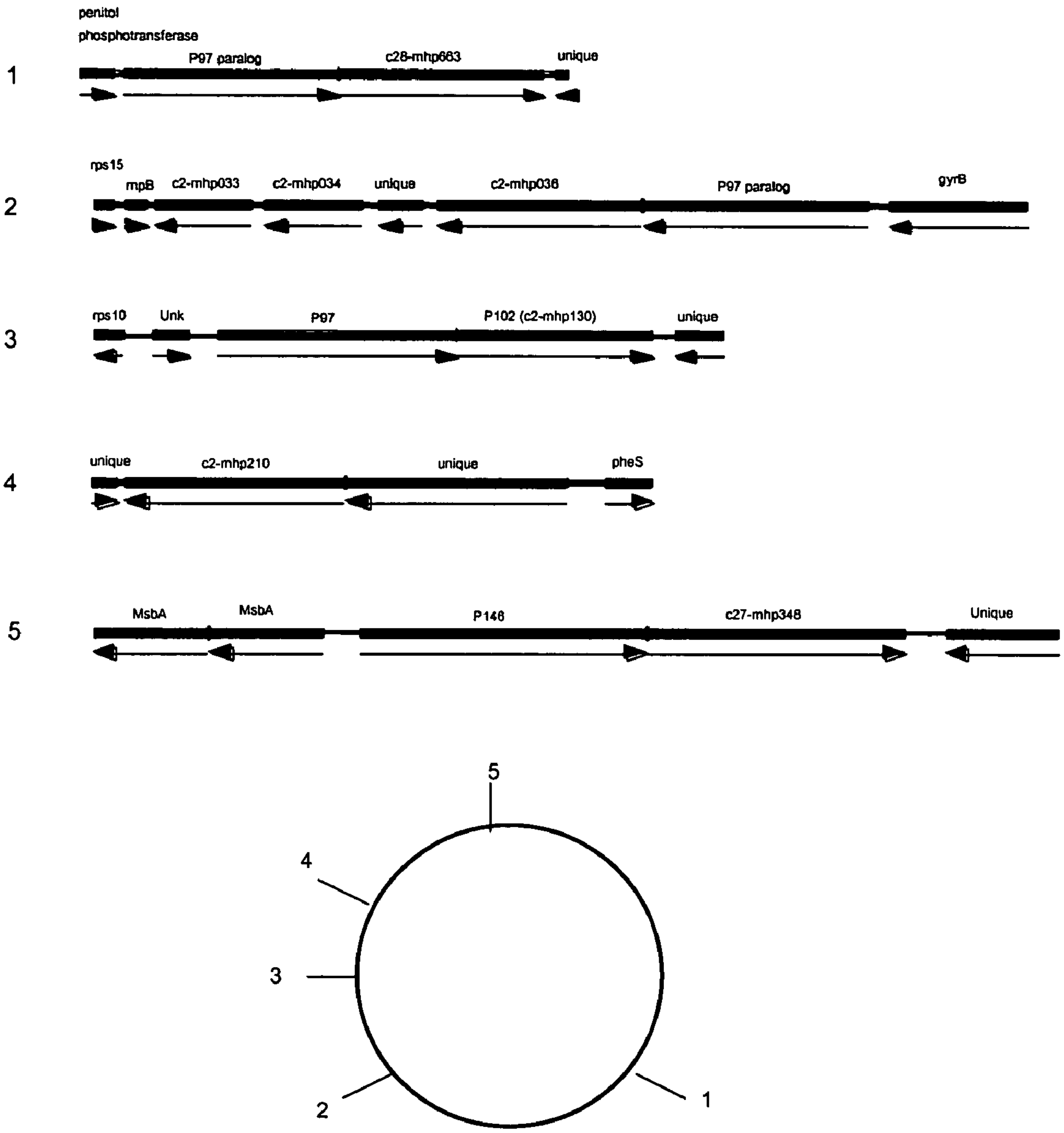
FIG. 21 is the structure of P102 paralogs and their organization in the chromosome.
Figure 22:
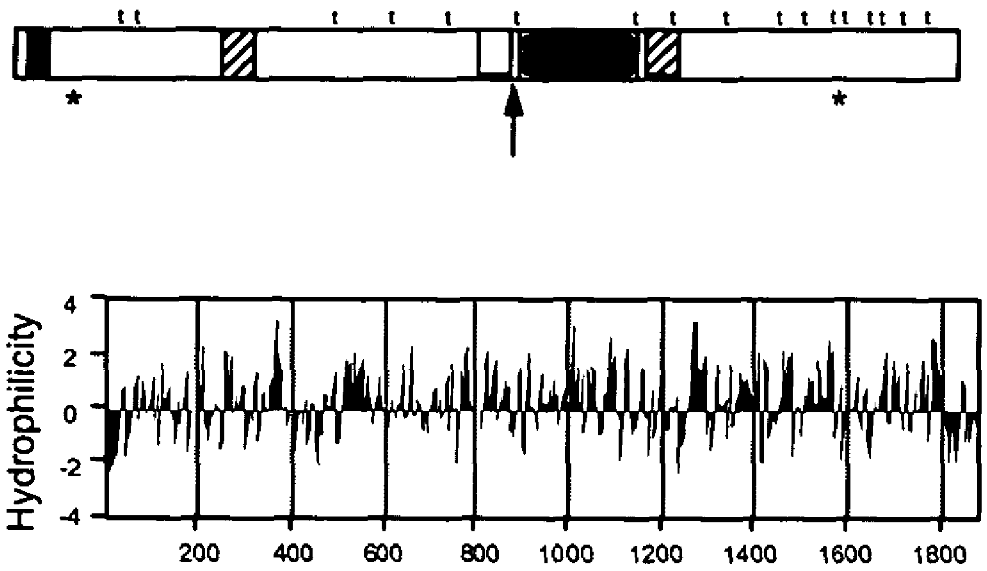
FIG. 22 shows a map and hydrophilicity plot of P216. The upper panel depicts a schematic diagram of the P216 protein sequence. Asterisks indicate locations of peptides used to clone the gene (left, amino acids 94-105) and used to make antisera specific for P130 (right, amino acids 1654-1668). The arrow indicates the position of the major cleavage event. The gray box indicates the position of the 30-kDa fragment cloned and expressed (amino acids 1043-1226). The inverted filled triangles are locations of tryptophan residues encoded by TGA codons. The hatched boxes are the location of the coiled coil domains. The white box indicates the location of the BNBD (amino acids 1012-1029). The black box represents the transmembrane domain (amino acids 7-30). The lower panel represents the hydrophilicity plot.

The following abbreviations are used in this application: aa, amino acid(s); Ab, antibody(ies); bp, base pair(s); CHEF, clamped homogenous electric field; H., *Haemophilus*; kb, kilobase(s) or 1000 bp; Kn, kanamycin; LB, Luria-Bertoni media; M., *Mycoplasma*; mAb, monoclonal Ab; ORF, open reading frame; PCR, polymerase chain reaction; $^R$, resistant/resistance; Tn, transposon(s); ::, novel junction (fusion or insertion). One letter and three letter code designations for amino acids are given in Table 1.

TABLE 1

Amino Acid Code Designations

| Amino Acid | Three letter code | One Letter code |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |

TABLE 1-continued

Amino Acid Code Designations

| Amino Acid | Three letter code | One Letter code |
|---|---|---|
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

*M. hyopneumoniae* Polypeptides and Nucleic Acids

As used herein, the term "polypeptide" refers to a polymer of three or more amino acids covalently linked by amide bonds. A polypeptide may or may not be post-translationally modified. As used herein, the term "purified polypeptide" refers to a polypeptide preparation that is substantially free of cellular material or other contaminating polypeptides from the cell or tissue source from which the polypeptide is derived, or substantially free of chemical precursors or other chemicals when chemically synthesized. For example, a polypeptide preparation is substantially free of cellular material when the polypeptide is separated from components of the cell from which the polypeptide is obtained or recombinantly produced. Thus, a polypeptide preparation that is substantially free of cellular material includes, for example, a preparation having less than about 30%, 20%, 10%, or 5% (dry weight) of heterologous polypeptides (also referred to herein as a "contaminating polypeptides"). When a polypeptide is recombinantly produced, the polypeptide is also preferably substantially free of culture medium, i.e., culture medium represents less than about 20%, 10%, 5% of the volume of the polypeptide preparation. When a polypeptide is produced by chemical synthesis, it is preferably substantially free of chemical precursors or other chemicals, i.e., it is separated from chemical precursors or other chemicals that are involved in the synthesis of the polypeptide. Accordingly, such polypeptide preparations have less than about 30%, 20%, 10%, 5% (by dry weight) of chemical precursors or compounds other than the polypeptide of interest.

As used herein, the term "mutant" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide is immunoreactive with the wild-type polypeptide.

The term "conservative variation" denotes the replacement of an amino acid residue by another biologically similar residue, or the replacement of a nucleotide in a nucleic acid sequence such that the encoded amino acid residue does not change or is another biologically similar residue. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Any *M. hyopneumoniae* strain may be used as a starting material to produce the polypeptides and nucleic acids of the present invention. Suitable strains of *M. hyopneumoniae* may be obtained from a variety of sources, including depositories such as the American Type Culture Collection (ATCC) (Manassas, Va.) and the NRRL Culture Collection (Agricultural Research Service, U.S. Department of Agriculture, Peoria, Ill.). *M. hyopneumoniae* strains may also be obtained from lung secretions or tissues from sick animals followed by inoculating suitable culture media.

An immunogenic polypeptide of the present invention can have an amino acid sequence shown in FIG. 2, 4, 6, 8, 10, 12, 14, 16, 18, or 20. Alternatively, an immunogenic polypeptide of the present invention can be a fragment of a polypeptide that has an amino acid sequence shown in FIG. 2, 4, 6, 8, 10, 12, 14, 16, 18, or 20. An immunogenic polypeptide of the invention can be six or more, or preferably eight or more, amino acids in length, but less than the full-length number of amino acids. For example, an immunogenic polypeptide can be 10, 12, 15, 20, 25, 30, or greater than 30 amino acids in length. A polypeptide of the present invention also can be a mutant of a polypeptide having an amino acid sequence shown in FIG. 2, 4, 6, 8, 10, 12, 14, 16, 18, or 20. Mutations at either the amino acid or nucleic acid level may be useful in improving the yield of the polypeptides, their immunogenicity or antigenicity, or their compatibility with various expression systems, adjuvants and modes of administration. Synthetic or recombinant fragments of wild type or mutated polypeptides are characterized by one or more of the antigenic sites of native *M. hyopneumoniae* polypeptides, the sequences of which are illustrated in FIGS. 2, 4, 6, 8, 10, 12, 14, 16, 18, and 20.

The polypeptides of the present invention may be obtained from *M. hyopneumoniae* cells or may be produced in host cells transformed by nucleic acids that encode these polypeptides. Recombinant polypeptides produced from transformed host cells may include residues that are not related to *M. hyopneumoniae*. For example, a recombinant polypeptide may be a fusion polypeptide containing an amino acid portion derived from an expression vector, or other source, in addition to the portion derived from *M. hyopneumoniae*. A recombinant polypeptide may also include a starting methionine. Recombinant polypeptides of the invention display the antigenicity of native *M. hyopneumoniae* polypeptides the sequences of which are illustrated in FIGS. 2, 4, 6, 8, 10, 12, 14, 16, 18, and 20.

Nucleic acid sequences encoding full-length polypeptides of the present invention are shown in FIGS. 1, 3, 5, 7, 9, 11, 13, 15, 17, and 19. The present invention encompasses nucleic acid sequences, as well as fragments or mutants of these, that encode immunogenic polypeptides, i.e., capable of eliciting antibodies or other immune responses (e.g., T-cell responses of the immune system) that recognize epitopes of the polypeptides having sequences illustrated in FIGS. 2, 4, 6, 8, 10, 12, 14, 16, 18, and 20. Hence, nucleic acid sequences of the present invention may encode polypeptides that are full-length polypeptides, polypeptide fragments, and mutant or fusion polypeptides.

The term "nucleic acid" as used herein encompasses RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

The term "exogenous" as used herein with reference to nucleic acid and a particular cell refers to any nucleic acid that does not originate from that particular cell as found in nature. Thus, non-naturally-occurring nucleic acid is considered to be exogenous to a cell once introduced into the cell. It is important to note that non-naturally-occurring nucleic acid can contain nucleic acid sequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a cell once introduced into the cell, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid.

Nucleic acid that is naturally occurring can be exogenous to a particular cell. For example, an entire chromosome isolated from a cell of person X is an exogenous nucleic acid with respect to a cell of person Y once that chromosome is introduced into Y's cell.

Recombinant nucleic acid molecules that are useful in preparing the aforementioned polypeptides are also provided. Preferred recombinant nucleic acid molecules include, without limitation, (1) those having nucleic acid sequences illustrated in FIGS. 1, 3, 5, 7, 9, 11, 13, 15, 17, and 19; (2) cloning or expression vectors containing sequences encoding recombinant polypeptides of the present invention; (3) nucleic acid sequences that hybridize to those sequences that encode *M. hyopneumoniae* polypeptides of the invention; (4) degenerate nucleic acid sequences that encode polypeptides of the invention.

Nucleic acids of the invention may be inserted into any of a wide variety of expression vectors by a variety of procedures, generally through use of an appropriate restriction endonuclease site. Suitable vectors include, for example, vectors consisting of segments of chromosomal, non-chromosomal and synthetic nucleic acid sequences, such as various known derivatives of SV40; known bacterial plasmids, e.g., plasmids from *E. coli* including col E1, pCR1, pBR322, pMB9 and their derivatives; wider host range plasmids, e.g., RP4; phage DNAs, e.g., the numerous derivatives of phage λ, e.g., NM 989, and other DNA phages such as M13 or filamentous single stranded DNA phages; yeast plasmids such as the 2μ plasmid or derivatives thereof; viral DNA such as baculovirus, vaccinia, adenovirus, fowl pox virus, or pseudorabies; and vectors derived from combinations of plasmids and phage DNAs, such as plasmids which have been modified to employ phage DNA or other expression control sequences.

Within each specific cloning or expression vector, various sites may be selected for insertion of the nucleic acids of this invention. These sites are usually designated by the restriction endonuclease that cuts them, and there are various known methods for inserting nucleic acids into these sites to form recombinant molecules. These methods include, for example, dG-dC or dA-dT tailing, direct ligation, synthetic linkers, exonuclease and polymerase-linked repair reactions followed by ligation, or extension of the nucleic acid strand with DNA polymerase and an appropriate single-stranded template followed by ligation. It is to be understood that a cloning or expression vector useful in this invention need not have a restriction endonuclease site for insertion of the chosen nucleic acid fragment, and that insertion may occur by alternative means.

For expression of the nucleic acids of this invention, these nucleic acid sequences are operatively linked to one or more expression control sequences in the expression vector. Such operative linking, which may be effected before or after the chosen nucleic acid is inserted into a cloning vehicle, enables the expression control sequences to control and promote the expression of the inserted nucleic acid.

Any of a wide variety of expression control sequences—sequences that control the expression of a nucleic acid when operatively linked to it—may be used in these vectors to express the nucleic acid sequences of this invention. Such useful expression control sequences include, for example, the early and late promoters of SV40, the lac or trp systems, the TAC or TRC system, the major operator and promoter regions of λ, the control regions of fd coat protein, the promoter for 3-phosphoglycerate kinase or other glycolytic enzymes, the promoters of acid phosphatase, e.g., Pho5, the promoters of the yeast α-mating factors, and other sequences known to control the expression of genes in prokaryotic or eukaryotic cells or their viruses, and various combinations thereof. The expression vector also includes a non-coding sequence for a ribosome-binding site for translation initiation and a transcription terminator. The vector may also include appropriate sequences for amplifying expression. In mammalian cells, it is additionally possible to amplify the expression units by linking the gene to that coding for dehydrofolate reductase and applying a selection to host Chinese hamster ovary cells.

The vector or expression vehicle, and in particular, the sites chosen therein for insertion of the selected nucleic acid fragment, and the expression control sequence employed in this invention are determined by a variety of factors, e.g., number of sites susceptible to a particular restriction enzyme, size of the polypeptide to be expressed, expression characteristics such as the location of start and stop codons relative to the vector sequences, and other factors recognized by those of skill in the art. The choice of a vector, expression control sequence, and/or insertion site are determined by a balance of these factors, as not all selections are equally effective for a given case.

The recombinant nucleic acid molecule containing the desired coding sequence operatively linked to an expression control sequence may then be employed to transform a wide variety of appropriate hosts so as to permit such hosts (transformants) to express the coding sequence, or fragment thereof, and to produce the polypeptide, or portion thereof, for which the hybrid nucleic acid encodes. The recombinant nucleic acid molecule may also be employed to transform a host so as to permit that host on replication to produced additional recombinant nucleic acid molecules as a source of *M. hyopneumoniae* coding sequences and fragments thereof.

A wide variety of hosts are also useful in producing polypeptides and nucleic acids of this invention. These hosts include, for example, bacteria such as *E. coli, Bacillus* and *Streptomyces,* fungi such as yeasts, and animal or plant cells in tissue culture. The selection of an appropriate host for these uses is controlled by a number of factors. These include, for example, compatibility with the chosen vector, toxicity of the co-products, ease of recovery of the desired polypeptide, expression characteristics, biosafety and costs. No absolute choice of host may be made for a particular recombinant nucleic acid molecule or polypeptide from any of these factors alone. Instead, a balance of these factors is applied with the realization that not all hosts may be equally effective for expression of a particular recombinant nucleic acid molecule.

It is also understood that the nucleic acid sequences that are inserted at the selected site of a cloning or expression vector may include nucleotides that are not part of the actual coding sequence for the desired polypeptide or may include only a fragment of the entire coding sequence for that polypeptide. It is only required that whatever DNA sequence is employed, the transformed host produces a polypeptide having the antigenicity of native *M. hyopneumoniae* polypeptides.

For example, in an expression vector of this invention, a nucleic acid of this invention may be fused in the same reading frame to a portion of a nucleic acid sequence coding for at least one eukaryotic or prokaryotic carrier polypeptide or a nucleic acid sequence coding for at least one eukaryotic or prokaryotic signal sequence, or combinations thereof. Such constructions may aid in expression of the desired nucleic acid sequence or improve purification, permit secretion, and preferably maturation of the desired polypeptide from the host cell. The nucleic acid sequence may alternatively include an ATG start codon, alone, or together with other codons, fused directly to the sequence encoding the first amino acid of a desired polypeptide. Such constructions enable the production of, for example, a methionyl or other peptidyl polypeptide that is part of this invention. This N-terminal methionine or peptide may then be cleaved intracellularly or extracellularly by a variety of known processes or the polypeptide used together with the methionine or other fusion attached to it in the compositions and methods of this invention.

The appropriate nucleic acid sequence present in the vector when introduced into a host may express part or only a portion of the polypeptide that is encoded, it being sufficient that the expressed polypeptide be capable of eliciting an antibody or other immune response that recognizes an epitope of the amino acid sequence depicted in FIG. 2, 4, 6, 8, 10, 12, 14, 16, 18, or 20. For example, in employing *E. coli* as a host organism, the UGA codon is a stop codon so that the expressed polypeptide may only be a fragment of the polypeptide encoded by the vector, and therefore, it is generally preferred that all of the UGA codons in the appropriate nucleic acid sequence be converted into non-stop codons. Alternatively, an additional nucleic acid sequence that encodes a t-RNA that translates the UGA codon into a tryptophan residue can be introduced into the host.

The polypeptide expressed by the host transformed by the vector may be harvested by methods known to those skilled in the art, and used for protection of a non-human animal such as swine, cattle, etc. against enzootic pneumonia caused by *M. hyopneumoniae*. The polypeptide is used in an amount effective to provide protection against enzootic pneumonia caused by *M. hyopneumoniae* and may be used in combination with a suitable physiologically acceptable carrier as described below.

Detecting *M. hyopneumoniae*

The polypeptides of the present invention may also be used as antigens for diagnostic purposes to determine whether a biological test sample contains *M. hyopneumoniae* antigens or antibodies to these antigens. Such assays for *M. hyopneumoniae* infection in an animal typically involve incubating an antibody-containing biological sample from an animal suspected of having such a condition in the presence of a detectably labeled polypeptide of the present invention, and detecting binding. The immunogenic polypeptide is generally present in an amount that is sufficient to produce a detectable level of binding with antibody present in the antibody-containing sample.

Thus, in this aspect of the invention, the polypeptide may be attached to a solid phase support, e.g., a microtiter plate, which is capable of immobilizing cells, cell particles or soluble polypeptides. The support may then be washed with suitable buffers followed by treatment with the sample from the animal. The solid phase support may then be washed with the buffer a second time to remove unbound antibody. Labeled polypeptide is added and the support is washed a third time to remove unbound labeled polypeptide. The amount of bound label on said solid support may then be detected by conventional means.

By "solid phase support" is intended any support capable of binding antigen or antibodies. Well-known supports, or carriers, include glass, polystyrene, polypropylene, polyethylene, dextran, nylon, amylases, natural and modified celluloses (especially nitrocellulose), polyacrylamides, agarose, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as for example, a sheet or test strip. Preferred supports include polystyrene beads.

*M. hyopneumoniae* specific antibody can be detectably labeled by linking the same to an enzyme and using it in an enzyme immunoassay (EIA), or enzyme-linked immunosorbent assay (ELISA). This enzyme, in turn, when later exposed to its substrate, will react with the substrate in such a manner as to produce a chemical moiety that can be detected, for example, by spectrophotometric, fluorometric or by visual means. Enzymes that can be used to detectably label the *M. hyopneumoniae* specific antibody include, but are not limited to, horseradish peroxidase, malate dehydrogenase, staphylococcal nuclease, delta-V-steroid isomerase, yeast alcohol dehydrogenase, alpha-glycerophosphate dehydrogenase, triose phosphate isomerase, alkaline phosphatase, asparaginase, glucose oxidase, beta-galactosidase, ribonuclease, urease, catalase, glucose-6-phosphate dehydrogenase, glucoa/nylase and acetylcholinesterase.

Detection may be accomplished using any of a variety of immunoassays. For example, by radioactively labeling the recombinant protein, it is possible to detect antibody binding through a radioimmunoassay (RIA). The radioactive isotope can be detected by such means as the use of a gamma counter or a scintillation counter or by autoradiography. Isotopes which are particularly useful for the purpose of the present invention include $^{3}H$, $^{125}I$, $^{131}I$, $^{35}S$, and $^{14}C$, preferably $^{125}I$.

It is also possible to label the recombinant polypeptide with a fluorescent compound. When the fluorescently labeled polypeptide is exposed to light of the proper wavelength, its presence can then be detected due to fluorescence. Among the most commonly used fluorescent labeling compounds are fluorescein isothiocyanate, rhodamine, phycoerytherin, phycocyanin, allophycocyanin, o-phthaldehyde and fluorescamine. The polypeptide can also be detectably labeled using fluorescence emitting metals such as $^{152}Eu$, or others of the lanthanide series. These metals can be attached to the protein using such metal chelating groups as diethylenetriaminepentaacetic acid (DTPA) or ethylenediamine-tetraacetic acid (EDTA).

The polypeptide also can be detectably labeled by coupling it to a chemiluminescent or bioluminescent compound. The presence of the chemiluminescent-tagged polypeptide is then determined by detecting the presence of luminescence that arises during the course of a chemical reaction. Bioluminescence is a type of chemiluminescence found in biological systems in which a catalytic protein increases the efficiency of the chemiluminescent reaction. Examples of particularly useful chemiluminescent labeling compounds are luminol, isoluminol, theromatic acridinium ester, imidazole, acridinium salt and oxalate ester. Important bioluminescent compounds for purposes of labeling are luciferin, luciferase and aequorin.

Detection of the label may be accomplished by a scintillation counter, for example, if the detectable label is a radioactive gamma emitter, or by a fluorometer, for example, if the label is a fluorescent material. In the case of an enzyme label, the detection can be accomplished by colorimetric methods that employ a substrate for the enzyme. Detection may also be accomplished by visual comparison of the extent of enzymatic reaction of a substrate in comparison with similarly prepared standards.

The detection of foci of detectably labeled antibodies is indicative of a disease or dysfunctional state and may be used to measure *M. hyopneumoniae* in a sample. The absence of such antibodies or other immune response indicates that the animal has been neither vaccinated nor infected. For the purposes of the present invention, the bacterium that is detected by this assay may be present in a biological sample. Any sample containing it can be used, however, one of the benefits of the present diagnostic invention is that invasive tissue removal may be avoided. Therefore, preferably, the sample is a biological fluid such as, for example, blood, or nasal, throat or lung fluid, but the invention is not limited to assays using these samples.

In situ detection may be accomplished by removing a histological specimen from an animal, and providing the combination of labeled antibodies of the present invention to such a specimen. The antibody (or fragment) is preferably provided by applying or by overlaying the labeled antibody (or fragment) to a biological sample. Through the use of such a procedure, it is possible to determine not only the presence of *M. hyopneumoniae* but also the distribution of it in the examined tissue. Using the present invention, those of ordinary skill will readily perceive that any of a wide variety of histological methods (such as staining procedures) can be modified in order to achieve such in situ detection.

Alternatively, a sample (e.g., a fluid or tissue sample) may be tested for the presence of a coding sequence for a *M. hyopneumoniae* polypeptide of the invention by reaction with a recombinant or synthetic nucleic acid sequence contained within the sequence shown in FIGS. 1, 3, 5, 7, 9, 11, 13, 15, 17, 19, or any RNA sequence equivalent to this nucleic acid sequence. The absence of the coding sequence indicates that the animal has been neither vaccinated nor infected. This test involves methods of synthesis, amplification, or hybridization of nucleic acid sequences that are known to those skilled in the art. See, for example, Sambrook et al. (1989) *Molecular Cloning: A Laboratory Manual*, $2^{nd}$ Ed, Cold Spring Harbor Laboratory, Cold Spring Harbor, N.Y.; PCR, A Practical Approach, Vols 1 & 2, McPherson et al. (eds.), Oxford University Press, 1992 and 1995; and PCR Strategies, Innis (ed.), Academic Press, 1995, herein incorporated by reference.

Compositions

The present invention also contemplates a composition (e.g., a vaccine) comprising the recombinant polypeptides of the present invention, or nucleic acid sequences encoding these polypeptides, for immunizing or protecting non-human animals, preferably swine, against *M. hyopneumoniae* infections, particularly enzootic pneumonia. The terms "protecting" or "protection" when used with respect to the composition for enzootic pneumonia described herein means that the composition prevents enzootic pneumonia caused by *M. hyopneumoniae* and/or reduces the severity of the disease. When a composition elicits an immunological response in an animal, the animal is considered seropositive, i.e., the animal produces a detectable amount of antibodies against a polypeptide of the invention. Methods for detecting an immunological response in an animal are well known.

Compositions generally include an immunologically effective dosage of a polypeptide of the invention. An "immunologically effective" dosage is an amount that, when administered to an animal, elicits an immunological response in the animal but does not cause the animal to develop severe clinical signs of an infection. An animal that has received an immunologically effective dosage is an inoculated animal or an animal containing an inoculant of an immunologically effective amount of a polypeptide of the invention. Immunologically effective dosages can be determined experimentally and may vary according to the type, size, age, and health of the animal vaccinated. The vaccination may include a single inoculation or multiple inoculations. Other dosage schedules and amounts, including vaccine booster dosages, may be useful.

The composition can be employed in conjunction with a carrier, which may be any of a wide variety of carriers. Representative carriers include sterile water, saline, buffered solutions, mineral oil, alum, and synthetic polymers. Additional agents to improve suspendability and dispersion in solution may also be used. The selection of a suitable carrier is dependent upon the manner in which the composition is to be administered. The composition is generally employed in non-human animals that are susceptible to enzootic pneumonia, in particular, swine.

The composition may be administered by any suitable method, such as intramuscular, subcutaneous, intraperitoneal or intravenous injection. Alternatively, the composition may be administered intranasally or orally, such as by mixing the active components with feed or water, or providing a tablet form. Methods such as particle bombardment, microinjection, electroporation, calcium phosphate transfection, liposomal transfection, and viral transfection are particularly suitable for administering a nucleic acid. Nucleic acid compositions and methods of their administration are known in the art, and are described in U.S. Pat. Nos. 5,836,905; 5,703,055; 5,589,466; and 5,580,859, which are herein incorporated by reference. Other means for administering the composition will be apparent to those skilled in the art from the teachings herein; accordingly, the scope of the invention is not limited to a particular delivery form.

The composition may also include active components or adjuvants (e.g., Freund's incomplete adjuvant) in addition to the antigen(s) or fragments hereinabove described. Adjuvants may be used to enhance the immunogenicity of an antigen. Among the adjuvants that may be used are oil and water emulsions, complete Freund's adjuvant, incomplete Freund's adjuvant, *Corynebacterium parvum, Hemophilus, Mycobacterium butyricum*, aluminum hydroxide, dextran sulfate, iron oxide, sodium alginate, Bacto-Adjuvant, certain synthetic polymers such as poly amino acids and co-polymers of amino acids, saponin, iota carrageenan, Regressin™, Avridine™, *Mannite monooleate*, paraffin oil, and muramyl dipeptide.

Nucleic acid or polypeptide compositions or vaccines as described herein can be combined with packaging materials including instructions for their use to be sold as articles of manufacture or kits. Components and methods for producing articles of manufactures are well known. The articles of manufacture may combine one or more vaccines (e.g., nucleic acid or polypeptide) as described herein. Instructions describing how a vaccine is effective for preventing the incidence of a *M. hyopneumoniae* infection, preventing the occurrence of the clinical signs of a *M. hyopneumoniae* infection, ameliorating the clinical signs of a *M. hyopneumoniae* infection, lowering the risk of the clinical signs of a *M. hyopneumoniae* infection, lowering the occurrence of the clinical signs of a *M. hyopneumoniae* infection and/or spread of *M. hyopneumoniae* infections in animals may be included in such kits.

Conveniently, vaccines of the invention may be provided in a pre-packaged form in quantities sufficient for a protective dose for a single animal or for a pre-specified number of animals in, for example, sealed ampoules, capsules or cartridges.

Application of the teachings of the present invention to a specific problem or environment is within the capabilities of one having ordinary skill in the art. Examples of the products and processes of the present invention appear in the following examples.

The invention will be further described in the following examples, which do not limit the scope of the invention described in the claims.

EXAMPLES

A. P102 and Paralogs Thereof

Example A.1

*Mycoplasma* Strains

*Mycoplasmas hyopneumoniae* strains used included the 232, J, and Beaufort. The source and culture conditions used to grow *M. hyopneumoniae* are as described in Scarman et al. (1997) *Microbiology* 143:663-673.

Example A.2

Cloning of the Gene Encoding P102

The gene encoding P102 was obtained by polymerase chain reaction (PCR) and cloned into pTrcHis (Invitrogen). The oligonucleotides TH130 and TH131 were used to amplify the region encoding amino acids 33 to 887 of P102 from pISM1217 as described in Hsu and Minion ((1998) *Infect. Immun.* 66:4762-4766). The PCR product having 5' BamHI and 3' PstI restriction enzyme sites was digested sequentially with BamHI and PstI, gel purified, and ligated into BamHI/PstI-digested pTrcHis plasmid DNA. The ligation mixture was transformed into CSH50 *Escherichia coli*, and transformants were selected for ampicillin resistance (100 μg per mL). The resulting plasmid was sequenced with primer SA1528 to confirm the insertion and orientation of the insert.

Site directed mutagenesis was performed on the insert sequence to remove TGA codons, which code for tryptophan in *Mycoplasmas*. Directed mutagenesis was performed using the Stratagene QuikChange Site-Directed Mutagenesis Kit (Stratagene, CA) according to the manufacturer's instructions. Five TGA codons in the cloned sequence were changed to TGG using the following primer pairs:

```
P102.2f: 5'-GAT AAT TTT AAA AAA TGG TCG GCA AAA ACA GTT TTA    (SEQ ID NO:21)
         ACT GCT GCC-3';

P102.2r: 5'-GGC AGC AGT TAA AAC TGT TTT TGC CGA CCA TTT TTT    (SEQ ID NO:22)
         AAA ATT ATC-3';

P102.3f: 5'-GAA AGA GGA AGT AAT TGG TTT TCA CGA CTT GAA AGA    (SEQ ID NO:23)
         GC-3';

P102.3r: 5'-GCT CTT TCA AGT CGT GAA AAC CAA TTA CTT CCT CTT    (SEQ ID NO:24)
         TC-3';

P102.4f: 5'-CTA AAA TTC TAA AAT CCT GGC TTG AAA CAA ATC TTC    (SEQ ID NO:25)
         AAG GC-3';

P102.4r: 5'-GCC TTG AAG ATT TGT TTC AAG CCA GGA TTT TAG AAT    (SEQ ID NO:26)
         TTT AG-3';

P102.5f: 5'-GCC TCT CTG ATT ATT GGT ATG GAT CTC CGA ATT C-3';  (SEQ ID NO:27)

P102.5r: 5'-GAA TTC GGA GAT CCA TAC CAA TAA TCA GAG AGG C-3';  (SEQ ID NO:28)

P102.6f: 5'-GGG ACA AGC ATT TGG ACA GCT TTT AAT TTC G-3';      (SEQ ID NO:29)

P102.6r: 5'-CGA AAT TAA AAG CTG TCC AAA TGC TTG TCC C-3'.      (SEQ ID NO:30)
```

*E. coli* XL1-Blue MRF' was the recipient for each mutagenesis step. To confirm the sequence and the single-base changes, and to determine whether errors were introduced during the cloning and mutagenesis steps, the final product was sequenced using the primers:

```
P102.2-SEQ:
5'-TCC GAC GAT GAC GAT AAG-3'; (SEQ ID NO:31)

P102.5-SEQ:
5'-TGG AAA ATT AGT TCT TGG-3'; (SEQ ID NO:32)

P102.6-SEQ:
5'-AGT TTC CAC TTC ATC GCC-3'. (SEQ ID NO:33)
```

The final construct was designated pISM1316.6.

Example A.3

Expression and Purification of P102

Plasmid pISM1316.6 was transformed into *E. coli* ER1458 (F-Δ(lac)U169 lon-100 hsdR araD139 rpsL(StrR) supF mcrA trp+zjj202::Tn10(TetR) hsdR2(rk-mk+) mcrB1), a Lon protease mutant, in preparation for protein expression. An overnight culture was diluted 1:10 into fresh superbroth medium (per liter; 32 g Bacto tryptone, 20 g yeast extract, 5 g sodium chloride, pH 7.3) containing 1 mM isopropyl thiogalactopyranoside (IPTG) and protease inhibitor cocktail (Sigma P8848) at a 1:200 dilution. The culture was incubated for 5 hours at 30° C. with shaking. The cells were collected by centrifugation and resuspended in TS buffer (10 mM Tris, 100 mM sodium chloride, pH 7.4) plus 8 M urea and 2 mg/mL of lysozyme. After incubating for 30 minutes on ice, the suspension was frozen in a dry ice ethanol bath and passed sequentially through three freeze-thaw cycles. The chromosomal DNA was sheared by passing the suspension through an 18-gauge needle, and insoluble cellular debris was removed by centrifugation. The final solution was passed through a Talon Metal Affinity Resin (Clontech Laboratories, Inc., CA) column. The column was washed with 10 column volumes of TS buffer containing 10 mM imidazole. The bound protein was eluted with TS buffer containing 500 mM imidazole, and the column eluent was dialyzed overnight against phosphate buffered saline (10 mM $Na_2HPO_4$, 100 mM NaCl, pH 7.4). Purity of the protein preparations was assessed by sodium dodecyl sulfate gel electrophoresis and by Western blotting using 6×His monoclonal antibody (Clontech).

Example A.4

Generation of P102 Antisera

Mice were immunized with 10 μg of purified P102 mixed with 200 μL of Freund's incomplete adjuvant, and on day 21, second dosages were given. Ascites were developed by the introduction of Sp2 myeloma cells using the method of Luo and Lin ((1997) *BioTechniques* 23:630-632), and ascites fluid was aliquoted and stored at −70° C. Antibody specificity was tested by immunoblot analysis using purified P102 protein and *M. hyopneumoniae* whole antigen.

Example A.5

Immunoelectron Microscopic Analysis of Immunogold-labeled Cell Sections

To determine if P102 is surface exposed or associated with the P97 cilium adhesin, monospecific polyclonal anti-P102 antiserum was used in the following immunoelectron microscopic studies to determine the location of P102 in the *Mycoplasma* cell.

*M. hyopneumoniae* strains 90-1 and 60-3 were grown in modified Friis media (Friis (1971) *Acta Vet. Scand.* 12:69-79) until mid log phase as described (Hsu et al. (1997) *J. Bacteriol.* 179:1317-1323). The cells were pelleted by centrifugation and washed once with phosphate buffered saline (PBS) by centrifugation. Cells were resuspended in PBS and then reacted with either anti-P102 ascite fluid diluted 1:50, or F1B6 cell culture supernatant (Zhang et al. (1995) *Infect. Immun.* 63:1013-1019) diluted 1:10, overnight at 4° C. The next day, cells were washed five times with PBS and then reacted for 30 minutes at room temperature with goat anti-mouse IgG+IgM labeled with 10 nm gold particles (EY Laboratories, Inc., San Mateo, Calif.) diluted 1:25. The cells were then washed five times with PBS and pelleted by centrifugation.

The final cell pellets were fixed with 3% glutaraldehyde in 0.1 M sodium cacodylate buffer (pH 7.2) at 4° C. overnight. The pellets were washed three times, 15 minutes each time, with 0.1 M sodium cacodylate buffer and post fixed with 1% osmium tetroxide in 0.1 M sodium cacodylate buffer for 2 hours at room temperature. The pellets were then washed with distilled water, passed through an acetone series and embedded in Embed 812 and Araldite (Electron Microscopy Sciences, Fort Washington, Pa.).

For tracheal sections, *Mycoplasma*-free pigs were inoculated intratracheally with *M. hyopneumoniae* strain 232 as described in Thacker et al. ((1997) Potentiation of PRRSV pneumonia by dual infection with *Mycoplasma hyopneumoniae*. In *Conference of Research Workers in Animal Diseases*. Ellis, R. P. (ed.) Chicago, Ill.: Iowa State University Press, pp. 190). At 10 and 21 days, pigs were sacrificed, and tracheas were removed. One cm blocks of tissue were fixed with 1% glutaraldehyde overnight, dehydrated in an acetone series and embedded as above. Thick (1-2 μm) sections were stained with methylene blue polychrome and examined by microscopy for regions containing ciliated epithelium. Thin sections (80-90 nm) were then prepared for labeling. For some studies, cells grown in vitro were embedded and sectioned prior to staining. The sections were pretreated with ammonium chloride (1%) for 1 hour, 0.05 M glycine in PBS for 15 minutes, and blocked for 30 minutes in 2% fish gelatin+2% bovine serum albumin in TS buffer (10 mM Tris, 100 mM NaCl, pH 7.5). Primary antibodies were diluted (1:50) in TS buffer and reacted with sections for 30 minutes at room temperature. The sections were washed six times with TS buffer, and then incubated with goat anti-mouse IgG+IgM labeled with 10 nm gold particles (diluted 1:2) for 15 minutes at room temperature. Both primary antibodies and the conjugate were diluted and centrifuged briefly (12,000×g for 5 minutes) to remove gold aggregates prior to use. The sections were then washed six times with TS buffer, dried, contrasted with osmium vapors for 2 minutes, and stained with uranyl acetate-lead citrate. The sections were examined on a Hitachi 500 electron microscope at 75 kV.

In in vitro grown cells, gold particles were found external to the cells and were primarily associated with the extracellular matrix. Similar results were observed for cells that were stained before or after fixation and sectioning. Occasionally, particles were seen associated with the cell surface, and in rare cases, particles were seen intracellularly. In cells associated with swine cilia, however, gold particles were seen at high concentration intracellularly. P102 was also found in association with swine cilia, often in aggregates or at high concentrations. The extracellular matrix that was so prominent in broth grown cells was not evident in sections of infected swine epithelia.

Example A.6

Two-dimensional Electrophoresis

Two-dimensional gel electrophoresis (2-DGE) was carried out essentially as described by Guerreiro et al. ((1997) *Mol. Plant Microbe Interact.,* 10:506-16). First dimension immobilized pH gradient (IPG) strips (180 mm, linear and non-linear pH 3-10 and linear pH 4-7 and 6-11; Amersham Pharmacia Biotech, Uppsala, Sweden) were prepared for focusing by submersion in hydration buffer (8 M urea, 0.5% wt/vol CHAPS, 0.2% wt/vol DTT, 0.52% wt/vol Bio-Lyte and a trace of bromophenol blue) overnight. *M. hyopneumoniae* whole cell protein (100 μg for analytical gels, 0.5-1.0 mg for preparative gels and immunoblots) was diluted with sample buffer (8 M urea, 4% w/v CHAPS, 1% w/v DTT, 0.8% w/v Bio-Lyte 3-10, 35 mM Tris, and 0.02% w/v bromophenol blue) to a volume of 50 to 100 μL for application to the anodic end of each IPG strip. Isoelectric focusing was performed with a Multiphor II electrophoresis unit (Pharmacia) for 200 kVh at 20° C. except for pH 6-11 strips, which were electrophoresed for 85 kVh. IEF strips were reduced and alkylated in Tris-HCl (0.5 M, pH 6.8) containing 6 M urea, 30% w/v glycerol, 2% w/v sodium dodecyl sulfate (SDS), 2% w/v DTT and 0.02% bromophenol blue. Equilibrated strips were placed onto Pharmacia ExcelGels (T=12 to 14% acrylamide) for SDS-PAGE using the Multiphor II. Electrophoretic conditions consisted of 200 Volts for 1.5 hours followed by 4 hours at 600 Volts at 5° C. Gels were stained in Coomassie Blue R-250 (Bio-Rad, Hercules, Calif.), and proteins were transferred to polyvinylidene difluoride (PVDF) membranes using a Hoefer TE70 Series SemiPhor Semi-Dry Transfer Unit (Amersham Pharmacia Biotech, Uppsala, Sweden). The transfer was carried out for 1.5 hours at maximum voltage and a current measured by multiplying the area of the gel ($cm^2$) by 0.8 mA.

Example A.7

Post-separation Analyses

Protein spots were excised from gels using a sterile scalpel and placed in a 96 well tray. Gel pieces were washed with 50 mM ammonium bicarbonate/100% acetonitrile (60:40 v/v) and then dried in a Speed Vac (Savant Instruments, Holbrook, N.Y.) for 25 minutes. Gel pieces were then hydrated in 12 μL of 12 ng $\mu L^{-1}$ sequencing grade modified trypsin (Promega, Madison, Wis.) for 1 hour at 4° C. Excess trypsin solution was removed and the gel pieces immersed in 50 mM ammonium bicarbonate and incubated overnight at 37° C. Eluted peptides were concentrated and desalted using $C_{18}$ Zip-Tips™ (Millipore Corp., Bedford, Mass.). The peptides were washed on column with 10 μL of 5% formic acid. The bound peptides were eluted from the Zip-Tip™ in matrix solution (10 mg $mL^{-1}$ α-cyano-4-hydroxycinnamic acid [Sigma] in 70% acetonitrile) directly onto the target plate. Matrix-assisted laser desorption/ionization time-of-flight mass spectrometry (MALDI-TOF MS) mass spectra were acquired using either a PerSeptive Biosytems Voyager DE-STR (Framingham, Mass.) or a Micromass TofSpec2E (Micromass, Manchester UK). Both instruments were equipped with 337 nm nitrogen lasers. All spectra were obtained in reflectron/delayed extraction mode, averaging 256 laser shots per sample. Two-point internal calibration of spectra was performed based upon internal porcine trypsin autolysis peptides (842.5 and 2211.10 $[M+H]^+$ ions). A list of monoisotopic peaks corresponding to the mass of generated tryptic peptides was used to search a modified translated version of the *M. hyopneumoniae* genome. Successful identifications were based on the number of matching peptide masses and the percentage sequence coverage afforded by those matches. N-terminal Edman sequencing was performed as previously described (Nouwens et al., 2000).

Example A.8

P102 is Surface Expressed

To generate a P102 specific antibody, recombinant P102 protein was expressed in in *E. coli* and then purified as follows. The coding sequence for P102 was obtained from plasmid pISM1217, which contained the entire sequence of P102 (Hsu and Minion (1998) *Infect. Immun.* 66:4762-4766). The region of the coding sequence encoding amino acids 33-887 was amplified by PCR using primers having BamHI and PstI restriction sites at the 5' termini to enable cloning into pTrcHis. The resulting construct was designated pISM1249. To allow for expression of the coding sequence in *E. coli*, the TGA codons in the pISM1249 sequence were altered by site-directed mutagenesis to TGG codons. The final construct pISM1316.6 was sequenced to confirm these changes and to check for errors introduced by PCR during the mutagenesis step.

Expression of the cloned sequence in pISM1316.6 resulted in a poly-histidine-tagged protein of about 100 kDa. Expression levels of P102 were low in *E. coli* despite the removal of the opal (TGA) stop codons. A Talon Metal Affinity Resin column was used to remove contaminating *E. coli* proteins during purification. Mouse hyperimmune antiserum raised against this recombinant protein was used in immunoblot analysis of *M. hyopneumoniae* whole cells. The anti-P102 antiserum showed three bands indicating either the presence of cross-reactive proteins or that P102 was being proteolytically processed. Trypsin treatment of whole cells followed by immunoblot and development with the anti-P102 antiserum showed that P102 was located on the membrane surface; all immunoreactive bands were sensitive to trypsin.

Example A.9

P102 Paralogs are Found Throughout the *M. hyopneumoniae* Genome

Hybridization studies indicated that P102 or P102-related sequences may exist in multiple copies in the genome of *M. hyopneumoniae* (Hsu et al. (1997) *J. Bacteriol.* 179:1317-1323). Genome sequencing studies have identified four distinct paralogs of P102 (C2-mhp210, C27-mhp348, C28-mhp663, and C2-mhp036) and two partial paralogs (C2-mhp033 and C2-mhp034) scattered throughout the chromosome (FIG. 21). Further analysis of the genome sequence of *M. hyopneumoniae* revealed additional open reading frames with varying homologies to P102. Each of these appeared to be a fusion with a second gene, while the original P102 sequence had undergone significant evolution. Also, each paralog was part of a two-gene genetic structure, possibly organized into operons. In every case, the P102 paralog was the second or downstream gene. DNA sequence analysis of each of the P102 paralogs showed that homology to P102 was low, but amino acid homology was much higher. The amino acid sequences of the P102 paralogs are shown in FIGS. 2, 6, 12, 14, 16,18, and 20.

Example A.10

Biotin Labeling of Surface Accessible Proteins Identified Molecules Belonging to a Multi-gene Family Studies were undertaken to identify all of the surface accessible proteins in *M. hyopneumoniae* recognized by convalescent and hyperimmune swine sera. By combining surface biotinylation, two-dimensional immunoblotting, genomic and proteomic analysis, a subset of these surface molecules was mapped to the genome sequence of *M. hyopneumoniae.*

Initially, two-dimensional gel electrophoresis of biotinylated proteins identified groups of proteins that were surface exposed, highly expressed, and appeared to resolve along the pI gradient as a series of spots. The molecular masses of many of these proteins ranged from 40 to 130 kDa. Many of these proteins were recognized by convalescent and hyperimmune swine sera. This suggests that these proteins were expressed during *M. hyopneumoniae* infection and evoked an accompanying immune response.

Tryptic fragments of individual protein spots were analyzed by peptide mass fingerprinting, and the spectra matched to theoretical trypsin cleavage products generated from the *M. hyopneumoniae* genome database. Some of the spots of different molecular masses mapped to the same single copy gene.

Example A.11

Peptide Mass Fingerprinting and Biotinylation Studies Show that P102 Paralogs are Expressed Many of the proteins identified by biotinylation and peptide mass fingerprinting were related to products from the cilium adhesion operon (Hsu and Minion (1998) *Infect. Immun.* 66:4762-4766). In addition to the cilium adhesin P97, gene products representing P102 and related proteins were identified.

A. 12

Results

Results indicated that there were a surprising number of P102 paralogs that were all expressed and located on the surface of the organism. Some of the P102 paralogs had a greater degree of sequence identity with P97, while other P102 paralogs did not. None of the sequences surrounding the P102 paralogs were similar, which suggests that the P102 genes duplicated and moved independently of surrounding sequences. Differential staining of in vitro-grown and in vivo-grown organisms was observed, further suggesting that P102 might be involved in the hyperimmune-like responses seen during infection.

B. P216 Studies

Example B.1

*Mycoplasma* Strains and Culture

The source and culture conditions used to grow *M. hyopneumoniae* strains J, Beaufort and 232 are as described in Scarman et al. ((1997) *Microbiology* 143:663-673). *Mycoplasmas* were harvested by centrifugation at 10,000×g, washed three times with TS buffer (10 mM Tris, 150 mM NaCl, pH 7.5), and the final cell pellets were frozen at −20° C. until use.

Example B.2

Preparative Electrophoresis

Preliminary vaccine trials in swine immunised with size-fractionated antigens of *M. hyopneumoniae* indicated that antigen pools residing in two fractions, fractions 2 (85-150 kDa) and 3 (70-85 kDa), provided limited protection against a virulent challenge (Djordjevic et. al (1997) *Aust Vet J* 75:504-511). To determine the amino acid sequences of proteins residing in these molecular mass fractions, whole cell lysates of *M. hyopneumoniae* J strain were separated using 5-7% polyacrylamide resolving columns each with a 4% stacking gel using a BioRad 491 Prep Cell as described in Scarman et al. ((1997) *Microbiology* 143:663-673). Proteins corresponding to those defined for fractions 2 and 3 were pooled, concentrated by filtration, and resuspended in PBS. Protein fractions were digested with trypsin, separated using electrophoresis on precast 8-15% gradient Tricine gels (Novex), and then blotted onto PVDF membrane (BioRad, California, USA) (Towbin et al. (1979) *Proc. Natl. Acad. Sci. USA*. 76:4350-4354). Protein fractions were analyzed by (1) reaction with porcine hyperimmune sera raised against the J strain of *M. hyopneumoniae* and (2) staining with amido black. Tryptic fragments stained with amido black that reacted with the hyperimmune sera were analysed by N-terminal amino acid sequencing.

Example B.3

Cloning of the Gene Encoding P216

To clone the genes encoding immunoreactive proteins, degenerate oligonucleotide probes were designed from the N-terminal peptide sequences determined above and used to probe EcoRI-digested chromosomal DNA by Southern analysis (Southern (1975) *J. Mol. Biol.* 98:503-517). EcoRI digested chromosomal DNA from the Beaufort strain was separated on a 1% agarose column prepared in 491 Prep Cell according to the BioRad Technical Note #2203. Samples from every fifth fraction were blotted to a nylon membrane and probed with degenerate oligonucleotide probes derived from the N-terminal sequences of tryptic fragments. DNA fragments from reactive fractions were incubated with the Klenow fragment and Pfu DNA polymerase to generate blunt ends. DNA fragments were ligated into pCR Script™ and transformed into XL10-Gold as outlined in the manufacturer's instructions (Stratagene).

In this way, N-terminal sequence analysis of an X kDa tryptic peptide fragment recognised by porcine hyperimmune generated the sequence ELEDNTKLIAPNIRQ (SEQ ID NO:34). Based on this amino acid sequence, a degenerate oligonucleotide having the sequence 5'-GAA (T/C)T(T/A) GAA GAT AAT AC(C/A/T) AAA TTA ATT GC(T/A) CCT AAT-3' (SEQ ID NO:35) was made and used as a probe to identify a hybridizing fragment of 4.5 kb. The clone containing this 4.5 kilobase fragment was designated p216.

Example B.4

DNA Sequence Analysis

For sequence analysis, purified plasmid DNA (Qiagen) or PCR product purified from agarose using the BRESA-CLEAN™ kit (Bresatec, Adelaide, Australia) was used. Oligonucleotide primers were obtained commercially (Sigma), and the BigDye™ Terminator Cycle Sequencing Kit (Applied Biosystems) was used for sequencing reactions. Results were analysed with an Applied Biosystems Model 377 automated sequencer.

Sequence analysis of the cloned fragment in p216 from the Beaufort strain revealed a large ORF that did not significantly match sequences deposited in GenBank. The fragment was the carboxy terminus of a larger ORF as the fragment had a stop codon but no ATG start codon. Additional upstream sequence was obtained by inverse PCR, and the final N-terminal sequence was obtained by PCR using primers designed from strain 232 genomic sequences. The complete ORF (C28-mph545; see, FIG. 7) was 5,637 base pairs in length and encoded a protein of 216 kDa designated P216 (C28-MPH545; see, FIG. 8). The ORF contained 17 TGA codons, 12 of which appeared in the carboxy terminal 85 kDa.

Blastp analysis of the complete gene sequence revealed near identity with the partial gene sequence YX2 (GenBank Accession No. AF279292) from *M. hyopneumoniae* strain 232 and limited sequence homology with the P97 cilium adhesin (GenBank Accession No. U50901) with 21% identities, 38% positives and 19% gaps (Expect=4e-18). Comparisons of the nucleotide and derived protein sequences with the database were performed using the package from the University of Wisconsin Genetics Group (GCG) Version 7, accessed via the Australian National Genomic Information Service (ANGIS, University of Sydney) and MacVector (Scientific Imaging Systems, Eastman Kodak Co., New Haven, Conn.).

DNA sequence encoding the P216 homologue from the 232 strain of *M. hyopneumoniae* was obtained as part of a genome-sequencing project. Southern blotting analysis using an oligonucleotide probe from the carboxy terminus showed that the *M. hyopneumoniae* genome contained a single copy of the gene encoding the 216-kDa protein. Blastn analysis with p216 and the *M. hyopneumoniae* genome database also identified a single copy. The protein has 1,879 amino acids, a pI of 8.51, and is highly hydrophilic. A protein motif search using the algorithm Prosite on the ISREC Profilescan server (www.isrec.isb-sib.ch/software/PFSCAN_form.html) identified a bipartite nuclear binding domain (BNBD) between amino acids 1012-1029.

The nucleotide sequence of the *M. hyopneumoniae* p216 gene from strain 232 and the J strain are shown in FIGS. 7 and 19, respectively.

Example B.5

Generation of Antisera Against *M. hyopneumoniae* Strain 232

Preparation of porcine hyperimmune serum against *M. hyopneumoniae* is as described in Scarman et al. (1997) *Microbiology* 143:663-673. In brief, *M. hyopneumoniae*-free swines were challenged with a preparation of *M. hyopneumoniae* strain 232 emulsified in Freund's complete adjuvant, and these swines were subjected to a second exposure one month later with the same preparation in Freund's incomplete adjuvant. Serum responses were monitored until an anti-*M. hyopneumoniae* response was confirmed by an enzyme-linked immunosorbent assay (ELISA).

Example B.6

Generation of P216 Polyclonal Antisera

To generate monospecific polyclonal antisera to P216, the DNA sequence encoding P216 from strain 232 was examined for the presence of TGA codons, since TGA codons encode tryptophans in *Mycoplasmas*. A region containing no TGA codons and encoding a 30 kDa protein (amino acids 1043-1226) was identified. PCR primers were designed to amplify and clone this region into pCR Script™ forming plasmid p216.1. The cloned fragment was then directionally cloned into pQE9 (Qiagen) by ligation of BamHI- and HindIII-digested p216.1 DNA to form p216.2. The ligation mixture was transformed into *Escherichia coli* M15[pREP4] according to the manufacturer's instructions (Qiagen). Colony hybridization using the DIG system (Roche) was used to identify transformants containing the proper fragment.

Cultures of the transformants containing p216.2 were grown in LB medium (Sambrook et al. (1989) *Molecular Cloning: A Laboratory Manual,* $2^{nd}$ Ed, Cold Spring Harbor Laboratory, Cold Spring Harbor, N.Y.) containing ampicillin (100 μg/mL) and kanamycin (25 μg/mL) at 37° C. with shaking. For expression from p216.2, cultures were treated with 1 mM isopropyl-β-D-thiogalactopyranoside (IPTG) after reaching an $OD_{600}$ of 0.6. After induction for 4 hours, the cells were harvested by centrifugation at 4,000×g for 20 minutes. Purification of the recombinant His-tagged protein was achieved using Ni-NTA resin under denaturing conditions as outlined in the manufacturer's instructions (Qiagen).

Purified recombinant protein was dialysed against PBS containing 5% glycerol and concentrated using polyvinylpyrrolidone (Sigma). Approximately 5 mg of purified protein in a volume of 250 μL were emulsified with an equal volume of Freund's incomplete adjuvant (Sigma). The preparation was given subcutaneously to rabbits at two sites and a booster immunization, similarly prepared, was given three weeks later. Serum response against the immunizing antigen was confirmed by immunoblot analysis.

Similarly, rabbit antisera directed against the N-terminal sequence of P216 were generated by immunization with the peptide DFLTNNGRTVLE (SEQ ID NO:36) (amino acids 94-105 of P216) conjugated to keyhole limpet hemocyanin. Rabbit immunizations were performed as described in (Scarman et al. (1997) *Microbiology* 143:663-673).

Example B.7

Electrophoretic and Immunoblot Analyses

Sodium dodecyl sulphate polyacrylamide gel electrophoresis (SDS-PAGE) and immunoblot analysis were performed as described by Laemmli (1970) *Nature* 227:680-685 and Towbin et al. (1979) *Proc. Natl. Acad. Sci. USA,* 76:4350-4354, respectively. Analytical electrophoretic gels containing *M. hyopneumoniae* strain 232 proteins were stained with silver (Rabilloud et al. (1992) *Electrophoresis* 13:264-266). Preparative gels were stained with colloidal Coomassie Brilliant Blue G-250 (0.1% Coomassie Brilliant Blue G-250 w/v, 17% w/v ammonium sulfate, 34% methanol v/v, 3% v/v ortho-phosphoric acid). Gels were destained in 1% v/v acetic acid for 1 hour.

Immunoblot analysis was used to determine if P216 is recognised by antibodies elicited during natural infection using swine field sera shown to contain antibodies against *M. hyopneumoniae* (Djordjevic et al. (1994) *Vet. Microbiol.* 39:261-273). The 30 kDa recombinant protein representing amino acids 1043-1226 of P216 was used as antigen in these experiments. Other immunoblot analyses included one- and two-dimensional blots of *M. hyopneumoniae* whole cells using swine convalescent sera pools (2D blots) and individual swine sera (1D blots). Swine hyperimmune sera were also used to screen for immunoreactive proteins in one- and two-dimensional immunoblot analyses. Rabbit antisera generated against the 30 kDa recombinant protein and the peptide DFLTNNGRTVLE (SEQ ID NO:36) specific for P130 were used to investigate processing of P216 in one-dimensional immunoblotting experiments as well.

Example B.8

Two-dimensional Gel Electrophoresis

Two-dimensional gel electrophoresis was carried out essentially as described by Guerreiro et al. ((1997) *Mol Plant Microbe Interact* 10:506-516). First dimension immobilized pH gradient (IPG) strips (180 mm, linear and non-linear pH 3-10 and linear pH 4-7; Pharmacia-Biotechnology, Uppsala, Sweden) were prepared for focusing by submersion in rehydration buffer (8 M urea, 0.5% w/v CHAPS, 0.2% w/v DTT, 0.52% w/v Bio-Lyte and a trace of bromophenol) overnight. *M. hyopneumoniae* 232 whole cell proteins (100 μg for analytical gels, 0.5-1.0 mg for preparative gels and immunoblots) were diluted with sample buffer (8 M urea, 4% w/v CHAPS, 1% w/v DTT, 0.8% w/v Bio-Lyte 3-10, 35 mM Tris, and 0.02% w/v bromophenol blue) to a volume of 50 to 100 μl for application to the anodic end of each IPG strip. Isoelectric focusing was run with the Immobiline DryStrip kit in a Multiphor II electrophoresis unit (Pharmacia-Biotechnology) for 200 kVh at 20° C. IEF strips were subsequently prepared for second dimension SDS-polyacrylamide gel electrophoresis (SDS-PAGE) by equilibration in Tris-HCl (0.5 M, pH 6.8) containing 6 M urea, 30% w/v glycerol, 2% w/v sodium dodecyl sulfate (SDS), 2% w/v DTT, and 0.02% bromophenol blue. Equilibrated strips were placed onto Pharmacia ExcelGel gels (T=12 to 14% acrylamide) for molecular mass separation of *M. hyopneumoniae* proteins on a Multiphor II unit. Electrophoretic conditions consisted of 200 Volts for 1.5 hour followed by 4 hours at 600 Volts. Gels were maintained at 5° C. throughout.

Example B.9

Peptide Mass Fingerprinting-mass Spectrometry

Proteins spots were manually excised and placed in a 96-well microtiter plate. Conditions used for trypsin digestion and for the generation of peptide mass fingerprints are described in Nouwens et al. (2000) *Electrophoresis* 21:3797-3809. A purification step was performed on the tryptic peptides for proteins with poor peptide mass fingerprints as described in Gobom et al. (1999) *J. Mass Spectrom.* 34:105-116. Protein identifications were assigned by comparing the peak lists generated from peptide mass fingerprinting data to a database containing theoretical tryptic digests of *M. hyopneumoniae* strain 232. The Protein-Lynx package (Micromass, Manchester, UK) was used to search databases.

Example B.10

Image Processing

Gels and immunoblots were digitized at 600 dpi with a UMAX PS-2400X lamp scanner using Photoshop 3.0 (Adobe, Mountain View, Calif.). Spot detection and gel-to-gel protein spot matching were performed with MELANIE II software (BioRad, Hercules, Calif.) run under OpenWindows 3.0. Apparent molecular masses were determined by co-electrophoresis with protein standards (Pharmacia-Biotechnology).

Example B.11

Results of Two-dimensional Electrophoresis and Peptide Mass Fingerprinting Analysis Analyses of two-dimensional electropherograms identified two clusters of spots that tracked along the pI gradient in an unusual fashion. Peptide mass fingerprinting analysis of spots within each of the clusters showed that the spots had identical mass fingerprints and were thus derived from the same molecule. Cluster 1 with an approximate mass of 130 kDa was mapped to the N-terminal region of P216 from the genome sequence of *M. hyopneumoniae* strain 232. Cluster 2 of approximately 85 kDa mapped to the carboxy terminus of the same ORF. The proteins were designated P130 and P85, respectively. The pI of cluster 1 ranged from 9.5 to 8.0, while the p1 of cluster 2 ranged from 9.0 to 6.5. Mass spectrometric analysis indicated that P216 was cleaved between amino acids 1004 and 1090 generating the two fragments of 130 and 85 kDa.

Example B.12

Results of Immunoblot Analysis

Two-dimensional immunoblots reacted with porcine hyperimmune sera revealed a complex pattern of spots two of which corresponded to P130 and P85. P85 was also strongly recognized by a pool of convalescent sera showing that it was an important antigen during disease. To investigate this further, a 30-kDa region spanning amino acids 1042-1226 in P85 was expressed, purified by nickel-affinity chromatography, and blotted onto PVDF membrane. Individual convalescent sera from swines known to be positive in a *M. hyopneumoniae*-specific ELISA reacted with the 30-kDa protein confirming that P216 is an important molecule recognized by the host immune response during the normal course of infection. Antibodies raised to a 30-kDa peptide spanning amino acids 1042-1226 reacted solely with the 85 kDa cleavage product suggesting that cleavage occurred between amino acids 1004 and 1042. Sera raised to the N-terminal peptide of P216 recognized only P130

Example B.13

Posttranslational Processing of P216 Among Different Strains of *M. hyopneumoniae*

To investigate fragment patterns of P216 in different *M. hyopneumoniae* strains, immunoblot analysis was performed with the anti-P130 N-terminal peptide and anti-P30 antisera. Antibodies raised against the N-terminal peptide recognized P130 and several lower molecular mass peptides in one-dimensional immunoblots of whole cell lysates of J and 232 strains. The pattern of proteins recognised by this antisera was different between the two strains. Antisera raised against the 30-kDa peptide strongly recognised an 85-kDa antigen in both J and 232 strains, but also reacted with a number of weakly reactive proteins. Similarly, the pattern recognised with the anti-30-kDa sera was different between J and 232.

To determine if different post-translational cleavage events were occurring among other strains of *M. hyopneumoniae*, a collection of strains from different geographic origins were examined by immunoblot. Anti-30 kDa sera reacted strongly to an 85-kDa antigen and other proteins of lower molecular mass in immunoblots of whole cell lysates from different strains of *M. hyopneumoniae*. These strains represented isolates recovered from different geographic locations within Australia and from different countries including the USA, Great Britain and France. The anti-P30 sera, however, did not react against antigens in immunoblots of whole cell lysates of related porcine *Mycoplasmas,* e.g. *Mycoplasma hyorhinis* and *Mycoplasma flocculare*, suggesting that P216 is a *M. hyopneumoniae*-specific antigen. Convalescent sera from different swines also recognized purified recombinant P30 indicating that P216 is expressed in vivo.

Example B.14

Surface Localization Studies

Several approaches were taken to determine if P216 and its cleavage products were associated with the outer membrane surface. These included trypsin digestion and cell surface biotinylation.

For trypsin digestion studies, all solutions and *M. hyopneumoniae* cell stocks were pre-equilibrated at 37° C. *M. hyopneumoniae* cells (200 mg/mL in PBS) were aliquoted (300 μL) into sterile eppendorf tubes at 37° C. and trypsin was added to a final concentration ranging from 0.1-1000 μg/mL. The suspensions were inverted gently and incubated at 37° C. for 20 minutes. Immediately after incubation, the cells were lysed in Laemmli buffer, heated at 95° C. for 10 minutes and analysed by SDS PAGE and immunoblotting. Trypsin digested both P85 and P130 in a concentration dependent manner, but did not digest the intracellular enzyme lactate dehydrogenase, a control for spontaneous lysis of cells (Strasser et al. (1991) *Infect. Immun.* 59:1217-22). This suggests that both portions of P216 are surface accessible and sensitive to trypsin digestion.

To further clarify this, surface biotinylation of *M. hyopneumoniae* was performed. The method described by Meier et al. ((1992) *Anal. Biochem.* 204:220-226) was used with the following modifications. All solutions were pre-chilled at 4° C.

and all manipulations were performed on ice. *M. hyopneumoniae* pellets (200 mg wet weight) were resuspended in 4 mL of BOS buffer (10 mM sodium tetraborate in 0.15 M NaCl, pH 8.8). Immediately after the addition of 5 μL of NHS-biotin (10 mg/mL in dimethylsulfoxide), the reaction was allowed to proceed for 1 to 8 minutes with swirling. To determine the most suitable reaction time, aliquots were removed at 1-minute intervals for 15 minutes. A reaction time of 5 minute was chosen for all subsequent studies except where noted. Biotinylation was stopped with the addition of 2 mL of 0.1 M $NH_4Cl$ that served to saturate unbound NHS-biotin. Cells were harvested by centrifugation (8,500×g, 10 minutes) and washed twice in TKMS buffer (25 mM Tris-HCl, pH 7.4, 25 mM KCl, 5 mM $MgCl_2$ and 0.15 M NaCl in PBS). The products were resolved by two-dimensional electrophoresis.

Both P130 and P85 were readily biotinylated, confirming that all parts of P216 were surface accessible.

Example B.15

Triton X-100 and X-114 Extractions

Integral membrane proteins from 200 mg wet weight of whole cells were extracted with TX-114 essentially as described by Bordier ((1981) *J. Biol. Chem.* 182:1356-1363). The resultant aqueous and detergent phases were collected and analysed by SDS-PAGE and immunoblotting. The phase partitioning activity of Triton X-114 causes separation of hydrophobic molecules into the detergent phase. When treated with Triton X-114, P85 remained in the insoluble pellet consisting of complex high molecular weight structures that (1) were membrane associated and (2) lacked the solubility of normal cytosolic proteins.

For Triton X-100 extraction, pelleted *M. hyopneumoniae* (strains J and Beaufort) cells (200 mg wet weight) were resuspended in 10 mL of TS buffer containing 1 mM phenylmethylsulfonyl fluoride. Proteins were extracted by the addition of 2% Triton X-100 (Amersham Pharmacia Biotechnology) and incubated at 37° C. for 30 minutes as described in Stevens and Krause ((1991) *J. Bacteriol* 173:1041-1050). Briefly, *M. hyopneumoniae* cell suspensions were centrifuged (14,000×g, 30 min) at 4° C. The aqueous phase was removed and the pellet was re-extracted as described above. The insoluble pellet and both aqueous phases were analysed by SDS-PAGE and immunoblotting using anti-30 kDa and sera raised against the peptide DFLTNNGRTVLE (SEQ ID NO:36).

With Triton X-100 fractionation, high molecular weight cytoskeletal-like proteins remain insoluble, but phase partitioning does not occur. When treated with Triton X-100, P85 partitioned primarily to the aqueous detergent-containing phase, but about 30% remained in the pellet. These data indicate that P216 may form extracellular oligomeric structures. The presence of coiled coil domains in both fragments of P216 also supports this hypothesis.

C. P97 Studies

Example C.1

Bacterial Strains and Plasmids

*M. hyopneumoniae* strains 232 (virulent parental strain), 232_91.3 (high adherent clone), 232_60.3 (low adherent clone), and J type strain (NCTC 10110) were grown in modified Friis broth and harvested as described by Zhang et al. ((1995) *Infect Immun* 63:1013-1019) and Djordjevic et al. ((1994) *Vet Microbiol* 39:261-273), respectively. All broth media were filter sterilized through 0.22 μm filters, which removed the majority of particulate matter. Mycoplasmas were harvested by centrifugation and extensively washed to remove remaining medium contaminants. *Escherichia coli* TOP10 containing pISM405 was grown on Luria Bertani (LB) agar or in LB broth (Sambrook et al., 1989) containing 100 μg $ml^{-1}$ ampicillin. Isopropyl-β-D-thiogalactopyranoside (IPTG) induction was carried out by the addition of IPTG to a final concentration of 1 mM. Bacterial cultures were routinely grown at 37° C. and liquid cultures were aerated by shaking at 200 rpm.

Example C.2

Construction and Expression of Adhesin Fusion Protein

Hexa-histidyl P97 fusion proteins were constructed using the pTrcHis (Invitrogen, Carlsbad, Calif.) cloning vector. Primers FMhp3 (5'-GAA CAA TTT GAT CAC AAG ATC CTG AAT ATA CC-3' (SEQ ID NO:37)) and RMhp4 (5'-AAT TCC TCT GAT CAT TAT TTA GAT TTT AAT TCC TG-3' (SEQ ID NO:38)) were used to amplify a 3013 bp fragment representing base pairs 315-3321 of the gene sequence containing amino acids 105-1107. The fragment was digested with BclI (underlined sequence) and inserted into the BamHI site of vector pTrcHisA. A construct with the proper fragment orientation was identified by restriction digests. The resulting 116-kDa recombinant P97-polyhistidine fusion protein contained the R1 and R2 repeat regions as well as the major cleavage site at amino acid 195 in the P97 sequence.

Example C.3

Antisera

The Mab F1B6 has been described (Zhang et al. (1995) *Infect. Immun.* 63:1013-1019). Mab F1B6 binds to the R1 region of the cilium adhesin that has at least 3 repeat sequences (Minion et al. (2000) *Infect. Immun.* 68:3056-3060). Peptides with sequences TSSQKDPST (ΔNP97) (SEQ ID NO:39) and VNQNFKVKFQAL (NP97) (SEQ ID NO:40) were used to raise antibodies against P97/P66 and P22, respectively. The peptides were bound to keyhole limpet hemocyanin with the Pierce Imjet Maleimide Activated Immunogen Conjugation Kit (Pierce Chemical Co., Rockford, Ill.). These conjugates were then used to generate mouse hyperimmune antisera by the method of Luo and Lin ((1997) *BioTechniques* 23:630-632). The resulting antisera were tested by enzyme linked immunosorbent assay (ELISA) using ovalbumin-peptide conjugate and purified recombinant P97 antigens, and by immunoblot with the recombinant P97 antigen. Antiserum raised against the C-terminal 28 kDa (R2 serum) of the cilium adhesin of strain J has been described (Wilton et al. (1998) *Microbiology* 144:1931-1943). Mouse Mab 2B6-D4 raised against human fibronectin was purchased commercially (BD Biosciences, Pharmingen) as was alkaline phosphatase conjugated goat anti-mouse Ig(H+L) antibodies (Southern Biotechnology Associates, Inc., Birmingham, Ala.). Goat anti-mouse IgG+IgM labeled with 10 nm colloidal gold particles (EY Laboratories, Inc., San Mateo, Calif.) was used in immunogold electron microscopy studies.

Example C.4

Immunoblot Analysis

Sodium dodecyl sulfate polyacrylamide gel electrophoresis (SDS-PAGE) and immunoblot analysis was performed as described by Laemmli ((1970) *Nature* 227:680-685) and Towbin et al. ((1979) *Proc. Natl. Acad. Sci. USA.* 76:4350-4354), respectively. Proteins were transferred to PVDF membranes (Micron Separations, Inc.). For the media control experiments, purified recombinant P97 was incubated with fresh and spent Friis media. Spent media was prepared from an early log phase culture that had been centrifuged and filtered through a 0.1 μm filter. Purified recombinant P97 (2.5 μg) in 20 μl phosphate buffered saline was diluted 1:1 in fresh or spent media and incubated overnight at 37° C. Ten μl of the mixture were the loaded onto SDS-PAGE gels, blotted to nitrocellulose and developed with F1B6 Mab. For ligand blotting, PVDF blots were transferred, blocked and washed as described previously (Wilton et al. (1998) *Microbiology* 144:1931-1943). Blots were exposed to human fibronectin (5 μg $ml^{-1}$) dissolved in TS buffer (TS buffer: 10 mM Tris-HCl, pH 7.4; 150 mM NaCl) for 1.5 h, washed, and exposed to 0.4 μg $ml^{-1}$ anti-human fibronectin Mabs for 1 h at room temperature. Blots were washed and developed as described above.

Example C.5

Trypsin Treatment of *M. hyopneumoniae*

*M. hyopneumoniae* cells (0.5 g) were treated with trypsin essentially as described previously (Wilton et al. (1998) *Microbiology* 144:1931-1943). Briefly, trypsin was added to cell suspensions of *M. hyopneumoniae* at 0, 0.3, 0.5, 1.0, 3.0, 10, 50, 300, and 500 μg $ml^{-1}$ at 37° C. for 15 min. Immediately after incubation, cell suspensions were lysed in Laemmli buffer and heated to 95° C. for 10 min. Lysates were analysed by SDS-PAGE and immunoblotting using F1B6 Mab.

Example C.6

Two-dimensional Gel Electrophoresis

Two-dimensional gel electrophoresis (2-DGE) was carried out essentially as described by Cordwell et al. ((1997) *Electrophoresis* 18:1393-1398). First dimension immobilized pH gradient (IPG) strips (180 mm, linear pH6-11; Amersham Phamracia Biotech, Uppsala, Sweden) were prepared for focusing by submersion in 2-DGE compatible sample buffer (5 M urea, 2 M thiourea, 0.1% carrier ampholytes 3-10, 2% w/v CHAPS, 2% w/v sulfobetaine 3-10, 2 mM tributyl phosphine (TBP; Bio-Rad, Hercules USA)) overnight. *M. hyopneumoniae* whole cell protein (250 μg)) was diluted with sample buffer to a volume of 100 μl for application to the anodic end of each IPG strip via an applicator cup. Isoelectric focusing was performed with a Multiphor II electrophoresis unit (Amersham Pharmacia Biotech) for 85 kVh at 20° C. IPG strips were detergent exchanged, reduced and alkylated in buffer containing 6 M urea, 2% SDS, 20% glycerol, 5 mM TBP, 2.5% v/v acrylamide monomer, trace amount of bromophenol blue dye and 375 mM Tris-HCl (pH 8.8) for 20 minutes prior to loading the IPG strip onto the top of an 8-18% T, 2.5% C (piperazine diacrylamide) 20 cm×20 cm polyacrylamide gel. Second-dimension electrophoresis was carried out at 4° C. using 3 mA/gel for 2 hours, followed by 20 mA/gel until the bromophenol blue dye had run off the end of the gel. Gels were fixed in 40% methanol, 10% acetic acid for 1 hour and then stained overnight in Sypro Ruby (Molecular Probes, Eugene, Oreg.). Images were acquired using a Molecular Imager Fx (Bio-Rad). Gels were then double-stained in Coomassie Blue G-250.

Example C.7

Post-separation Analyses

Protein spots were excised from gels using a sterile scalpel and placed in a 96 well tray (Gobom et al. (1999) *J. Mass. Spectrom.* 34:105-116). Gel pieces were washed with 50 mM ammonium bicarbonate/100% acetonitrile (60:40 v/v) and then dried in a Speed Vac (Savant Instruments, Holbrook, N.Y.) for 25 min. Gel pieces were then hydrated in 12 μl of 12 ng $\mu l^{-1}$ sequencing grade modified trypsin (Promega, Madison, Wis.) for 1 h at 4° C. Excess trypsin solution was removed and the gel pieces immersed in 50 mM ammonium bicarbonate and incubated overnight at 37° C. Eluted peptides were concentrated and desalted using $C_{18}$ Zip-Tips™ (Millipore Corp., Bedford, Mass.). The peptides were washed on a column with 10 μl 5% formic acid. The bound peptides were eluted from the Zip-Tip™ in matrix solution (10 mg $ml^{-1}$ α-cyano-4-hydroxycinnamic acid [Sigma] in 70% acetonitrile) directly onto the target plate. Matrix-assisted laser desorption/ionization time-of-flight mass spectrometry (MALDI-TOF MS) mass spectra were acquired using either a PerSeptive Biosytems Voyager DE-STR (Framingham, Mass.) or a Micromass TofSpec2E (Micromass, Manchester UK). Both instruments were equipped with 337 nm nitrogen lasers. All spectra were obtained in reflectron/delayed extraction mode, averaging 256 laser shots per sample. Two-point internal calibration of spectra was performed based upon internal porcine trypsin autolysis peptides (842.5 and 2211.10 $[M+H]^+$ ions). A list of monoisotopic peaks corresponding to the mass of generated tryptic peptides was used to search a modified translated version of the *M. hyopneumoniae* genome. Successful identifications were based on the number of matching peptide masses and the percentage sequence coverage afforded by those matches. N-terminal Edman sequencing was performed as previously described (Nouwens et al. (2000) *Electrophoresis* 21:3797-3809).

Example C.8

Immunoelectron Microscopy

*M. hyopneumoniae* strain 232 cells were grown to mid log phase, pelleted by centrifugation and washed with phosphate buffered saline (PBS). The final cell pellets were fixed with 3% glutaraldehyde in 0.1 M sodium cacodylate buffer (pH 7.2) at 4° C. overnight. The pellets were washed three times with 0.1 M sodium cacodylate buffer, 15 min between changes and post fixed with 1% osmium tetroxide in 0.1 M sodium cacodylate buffer for 2 h at room temperature. The pellets were then washed with distilled water, passed through an acetone series and embedded in Embed 812 and Araldite (Electron Microscopy Sciences, Fort Washington, Pa.). Thin sections (80-90 nm) were then washed six times with TS buffer, and reacted with F1B6 ascites fluid (diluted 1:50), anti-ΔNP97 ascites fluid (diluted 1:10), anti-NP97 ascites fluid (diluted 1:10), or mouse anti-human fibronectin (diluted 1:25) overnight at 4° C. The grids were washed five times with TS buffer and then reacted with goat anti-mouse IgG+IgM labeled with 10 nm colloidal gold particles (EY Laboratories, Inc.) diluted 1:25 for 30 min at room temperature. The cells were then washed 5 times with TS buffer, dried, contrasted with osmium vapors for 2 min, and stained with uranyl acetate-lead citrate. The sections were examined on a Hitachi 500 at 75 kV.

For tracheal sections, mycoplasma-free pigs were inoculated intratracheally with *M. hyopneumoniae* strain 232. At 10 and 21 days, pigs were sacrificed, tracheas were removed and 1 cm blocks of tissue fixed with 1% glutaraldehyde overnight, dehydrated in an acetone series, and embedded as above. Thick (1-2 μm) sections were stained with methylene blue polychrome and examined by microscopy for regions containing ciliated epithelium. Thin sections (80-90 nm) were then prepared for labeling. The sections were pretreated with ammonium chloride (1%) for 1 h, 0.05 M glycine in PBS for 15 min, blocked for 30 min in 2% fish gelatin+2% bovine serum albumin in TS buffer (10 mM Tris, 100 mM NaCl, pH 7.5). Primary antibodies were diluted in TS buffer and reacted with sections for 30 min at room temperature. The sections were washed six times with TS buffer, and then incubated with goat anti-mouse IgG+IgM labeled with 10 nm gold particles (diluted 1:2) for 15 min at room temperature. Both primary antibodies and the conjugate were diluted and centrifuged briefly (12,000×g for 5 min) prior to use. The sections were then washed six times with TS buffer, dried, contrasted with osmium vapors for 2 min, and stained with uranyl acetate-lead citrate. The sections were examined on a Hitachi 500 at 75 kV.

Example C.9

Fibronectin Binding Assay

Immunlon 2 (Dynatech Laboratories, Inc.) 96 well plates were coated with 100 μl of human fibronectin (Sigma, F 0895) at a concentration of 5 μg $ml^{-1}$ in 0.1 M sodium carbonate. Plates were incubated at 4° C. overnight, washed three times with PBS, and blocked with 1% bovine serum albumin in PBS for 2 hr. The plates were then incubated with purified recombinant P97 with or without inhibitor at a concentration of 10 μg $ml^{-1}$. Inhibitors tested were intact human fibronectin, 45-kDa proteolytic fragment of fibronectin (Sigma, F 0162), 30-kDa proteolytic fragment of fibronectin (Sigma, F 9911) and engineered RGD polymer (Sigma, 5022). They were added to Eppendorf tubes with purified recombinant P97 (10 μg $ml^{-1}$) at concentrations of 37.5 μg $ml^{-1}$, 7.5 μg $ml^{-1}$, and 1.5 μg $ml^{-1}$ and incubated at 37° C. for 1 hr. The recombinant P97 plus inhibitor was then transferred to a fibronectin coated plate, which was then incubated at 37° C. for 2 hr. Binding of P97 to fibronectin was assessed by ELISA with Mab F1B6. Optical density at 405 nm was indicative of P97 binding to fibronectin-coated wells. Three replicates per treatment were assayed from three different experiments. Statistical differences were determined by the General Linear Model with a linear contrast based on pooled variances.

Example C.10

Results of Two-dimensional Gel Electrophoresis and Mass Spectrometry

Previous studies have demonstrated that the gene product for the cilium adhesin of strain 232 (126-kDa preprotein, 1036 amino acids) undergoes a cleavage event at amino acid 195 to yield what was once thought to be the "mature" molecule (Hsu et al. (1997) *J. Bacteriol.* 179:1317-1323). During peptide mass mapping studies of J strain proteins, four spots of 22, 28, 66 and 94 kDa (subsequently referred to as P22, P28, P66 and P94, respectively) were identified that represented different fragments of the adhesin. The N-terminal sequences for these proteins allowed unequivocal alignment with the cilium adhesin preprotein. P94 of strain J, the homologue of P97 in strain 232, mapped to a region that begins immediately downstream of amino acid 195 until the end of the ORF. Two closely spaced proteins at 66 kDa had identical mass maps and corresponded to a region beginning immediately downstream of amino acid 195 of the adhesin and ending near the R1 repeat. N-terminal sequence analysis of P66 showed a sequence of ADEKTSS (SEQ ID NO:41) that is identical to that of P94. Immunoblotting results using Mab F1B6 confirmed that P66 contains R1. Thus, the cleavage event must occur immediately downstream of the R1 repeat region. These data suggest that a fragment approximately 28 kDa in size had been removed from the C-terminus in some, but not all of the P94 molecules. This observation was confirmed when a 28-kDa fragment was identified that mapped to the C-terminus of P94. Also, one and two-dimensional immunoblots of J strain proteins probed with antisera raised against a recombinant 28-kDa protein containing R2 but not R1 (Wilton et al. (1998) *Microbiology* 144:1931-1943) recognised both P28 and P94 proteins. Previously, it was shown that antisera raised against a 28-kDa C-terminal recombinant peptide of the adhesin recognised the mature form of this antigen (93-97 kDa) in different strains of *M. hyopneumoniae* and a 28-kDa fragment only in strain J (Wilton et al. (1998) *Microbiology* 144:1931-1943). Tryptic peptide mass mapping showed that peptides from P22 mapped to the first 190 amino acids of the 123-kDa adhesin preprotein. The N-terminal sequence of P22 (SKKSKTF (SEQ ID NO:42)) aligned to amino acids 2-8 in the N-terminus of the 123 kDa preprotein suggesting that cleavage of the hydrophobic leader peptide (amino acids 8-22) is not necessary for translocation of the cilium adhesin across the membrane.

Comparative peptide mass mapping studies of strain 232 identified two spots of 70 and 97 kDa, subsequently identified as P70 and P97, respectively. Mass maps representative of P97 corresponded to a region beginning immediately downstream of amino acid 195 until the end of the ORF and corresponded to the most abundant product of the 232 strain adhesin gene (Zhang et al. (1995) *Infect. Immun.* 63:1013-1019). Interestingly, mass maps representative of P70 corresponded to a region beginning immediately downstream of amino acid 195 and ending near the R1 repeat, a map that was virtually identical to P66 in strain J. The presence of six extra copies of the R1 repeat is the most likely explanation for the difference in masses between P66 and P70 in strains J and 232, respectively. Consistent with these data, immunoblots probed with antisera raised against a recombinant 28-kDa protein containing R2 but not R1 (Wilton et al. (1998) *Microbiology* 144:1931-1943) recognized P97 but not P70 or P28. Furthermore, P28 or P22 could not be identified on 2D gels of 232 proteins resolved by 2D gel electrophoresis in regions where they were identified in strain J. This variation was not due to differences in sequence since P22 sequences were identical in the two strains. This was not true for the P28 sequences, however. The predicted mass and pI for P28 from strain 232 was 24.6 kDa and 5.88, respectively, and for P28 from strain J, it was 26.0 kDa and 8.39. It was possible that P28 was not found in strain 232 because of the change in pI causing a shift in the gel location of the protein. It was also possible that additional cleavage of P22 occurred in strain 232 that did not in strain J.

To rule out the possibility that cleavage resulted from a proteolytic activity in the media used for culturing *M. hyopneumoniae*, purified recombinant P97 was incubated with fresh and spent medium and then examined for proteolytic cleavage by immunoblot. Because the medium contained 20% swine serum, large quantities of swine immunoglobulins were present in the protein samples causing some background staining with the anti-mouse conjugate. It was still clear, however, that neither fresh nor spent medium contained proteolytic activity capable of cleaving recombinant P97 after 12 hours of incubation at 37° C. Thus, cleavage of the cilium adhesin was mediated by mycoplasma-encoded activities and was not due to porcine serum or other medium components.

Example C.11

Trypsin Sensitivity of R1-containing Cleavage Products

Immunoblot analyses of strain J and 232 cells digested with different concentrations of trypsin was used to investigate the cellular location of R1-containing cleavage fragments. The F1B6 Mab typically recognised proteins with masses of 35, 66, 88, 94, and 123 kDa in strain J and a similar pattern was observed for strain 232. Exposure of intact *M. hyopneumoniae* to concentrations of trypsin ranging from 0.1-10 μg $ml^{-1}$ showed a gradual loss of the higher mass proteins. Concentrations between 10 and 50 μg $ml^{-1}$ resulted in the loss of all the immunoreactive proteins (except one of 35 kDa) indicating that R1-containing adhesin fragments are surface accessible. The pattern of digestion of R1-containing adhesin fragments was consistent in repeat experiments except that the 35 kDa fragment was not reliably resistant to trypsin at concentrations above 10 μg $ml^{-1}$. Identical blots reacted with antisera raised to recombinant *M. hyopneumoniae* lactate dehydrogenase (previously shown to reside cytosolically) (Strasser et al. (1991) *Infect. Immun.* 59:1217-1222) and to antisera raised to recombinant fragments of pyruvate dehydrogenase subunits A and D showed that these proteins remained detectable with trypsin concentrations up to 500 μg $ml^{-1}$. In control experiments where lysed cells were exposed to trypsin, lactate dehydrogenase and pyruvate dehydrogenase subunit D were rapidly degraded.

Example C.12

Results of Immunogold Electron Microscopy

Transmission electron microscopy studies have shown that high and low adherent strains of *M. hyopneumoniae* differ in their outer membrane structure. High adherent clones possessed fibrils on the outer surface that appeared to interconnect to adjacent cells; these fibrils were rarely observed in low adherence clones (Young et al. (1994) Isolation and characterization of high and low adherent clones of *Mycoplasma hyopneumoniae*. In *IOM Letters. 10th International Congress of the International Organization for Mycoplasmology*. Vol. 3 Bordeaux, France, pp. 684-685). Antisera generated against specific regions of the adhesin enabled analysis of cleavage in vivo using immunogold electron microscopy. Virulent strain 232 was used in these studies because these results would have the most impact on understanding pathogenic mechanisms. R1-specific Mab F1B6 and antisera raised to peptides TSSQKDPST (ΔNP97 antiserum) (SEQ ID NO:39) and VNQNFKVKFQAL (NP97 antiserum) (SEQ ID NO:40) were used in these studies. The Mab F1B6 remained associated with the mycoplasma membrane, but not intimately associated with the cell confirming a previous report (Zhang et al. (1995) *Infect. Immun.* 63:1013-1019) and the trypsin studies above. ΔNP97 antiserum showed that this portion of the molecule is located distal to the membrane in association with extracellular material of unknown composition. In some instances, the antibodies seemed to define fibrial-like structures still attached to the mycoplasma cell membrane. NP97 antibodies clustered in aggregates to cytosolic locations, intimately to the membrane surface, and were also observed at sites distant from the extracellular surface of the cell membrane.

Example C.13

Fibronectin Binding Results

Since cleavage of the cilium adhesin occurs at amino acid position 195 (Hsu et al. (1997) *J. Bacteriol.* 179:1317-1323), it was not readily apparent how the remaining adhesin could remain associated with the cell and direct binding to porcine cilia. Immunogold studies showed that all cilium binding R1 epitopes remained cell associated in the absence of the hydrophobic N-terminus sequence, but apparently are not inserted directly into the membrane. This is not surprising since no other region of the protein has sufficient hydrophobicity to direct membrane insertion (Hsu et al. (1997) *J. Bacteriol.* 179:1317-1323). The possibility that other proteins may play a role in bridging R1-containing protein fragments of the cilium adhesin to the membrane through protein-protein interactions was examined. Analysis of the predicted protein sequence of the 123 kDa adhesin preprotein with the computer program COILS (http://www.ch.embnet.org) revealed that the protein contained three coiled coil domains. One of these resided between amino acids 180-195 in P22 (14-, 21- and 28-amino acid window settings) and two were located in P97 between amino acids 367-387 (window setting 14) and 780-805 (window setting 14 and 21). These domains are known to mediate protein-protein interactions. In addition, it was thought that the R1 and R2 domains might also play a role in interactions with other proteins. One obvious protein to test was fibronectin, a protein found in abundance throughout the host and shown to participate in other bacterial-host interactions (Probert et al. (2001) *Infect. Immun.* 69:4129-4133; Talay et al. (2000) *Cell Microbiol.* 2:521-535; Rocha and Fischetti (1999) *Infect. Immun.* 67:2720-2728; and Schorey et al. (1996) *Mol. Microbiol.* 21:321-329).

Ligand blotting studies confirmed that recombinant P97 bound porcine fibronectin. Other fibronectin binding proteins were also identified in lysates of *M. hyopneumoniae* low (lane 1) and high (lane 2) adherent variants of strain 232 and in strain J (lane 3). The low and high adherent strains of 232 differed by the absence of a fibronectin-binding band at approximately 50 kDa, which was also present in strain J.

Fibronectin binding assays with human fibronectin and purified recombinant cilium adhesin were also performed. Maximum inhibition occurred with the engineered RGD domain at all three concentrations tested ($p<0.001$). Inhibition also occurred with intact fibronectin ($p<0.001$) as expected. Interestingly, the 45-kDa purified fragment of fibronectin enhanced binding at the highest concentration tested.

To investigate the role(s) fibronectin might play in the binding of *M. hyopneumoniae* to porcine respiratory epithelial cells, anti-fibronectin antibodies were applied to lung sections showing *M. hyopneumoniae* strain 232 in close association with respiratory epithelial cilia. Gold particles were localised in regions where *M. hyopneumoniae* cells were intimately associated with cilia, on the surface of cilia and on the surface of *M. hyopneumoniae* cells.

D. Detection of Infection and Immunogenic Compositions

Example D.1

Detection of *M. hyopneumoniae* Infection in Swine

The polypeptides displaying *M. hyopneumoniae* antigenicity of this invention may be used in methods and kits designed to detect the presence of *M. hyopneumoniae* infection in swine herds and therefore to recognize swine in a herd which have been infected by this bacteria. For example, the antigens produced by hosts transformed by recombinant nucleic acid molecules of this invention, or antibodies raised against them, can be used in RIA or ELISA for these purposes. In one type of radioimmunoassay, antibody against one or more of the antigens of this invention, raised in a laboratory animal (e.g., rabbits), is attached to a solid phase, for example, the inside of a test tube. Antigen is then added to the tube to bind with the antibody.

A sample of swine serum, taken from 1 of each 10 to 20 swine per herd, together with a known amount of antigen antibody labeled with a radioactive isotope, such as radioactive iodine, is then added to the tube coated with the antigen-antibody complex. Any antigen (a marker for *M. hyopneumoniae* infection) antibody in the swine serum will compete with the labeled antibody for the free binding sites on antigen-antibody complex. Once the serum has been allowed to interact, the excess liquid is removed, the test tube washed, and the amount of radioactivity measured. A positive result, i.e., that the tested swine's serum contains *M. hyopneumoniae* antibody, is indicated by a low radioactive count.

In one type of ELISA test, a microtiter plate is coated with one or more antigens of this invention and to this is added a sample of swine serum, again, from 1 in every 10 or 20 swine in a herd. After a period of incubation permitting interaction of any antibody present in the serum with the antigen, the plate is washed and a preparation of antigen antibodies, raised in a laboratory animal and linked to an enzyme label, is added, incubated to allow reaction to take place, and the plate is then rewashed. Thereafter, enzyme substrate is added to the microtiter plate and incubated for a period of time to allow the enzyme to work on the substrate, and adsorbance of the final preparation is measured. A large change in adsorbance indicates a positive result, i.e., the tested swine serum had antibodies to *M. hyopneumoniae* and was infected with that bacteria.

Example D.2

Immunogenic Compositions

Standard methods known to those skilled in the art may be used in preparing immunogenic compositions of polypeptides and nucleic acids of the present invention for administration to swine. For example, the polypeptide of choice may be dissolved in sterile saline solution. For long-term storage, the polypeptide may be lyophilized and then reconstituted with sterile saline solution shortly before administration. Prior to lyophilization, preservatives and other standard additives such as those to provide bulk, e.g., glycine or sodium chloride, may be added. A compatible adjuvant may also be administered with the composition.

In addition, compositions can be prepared using antibodies raised against the polypeptides of this invention in laboratory animals, such as rabbits. This "passive" vaccine can then be administered to swine to protect them from *M. hyopneumoniae* infection. Direct incorporation of nucleic acid sequences into host cells may also be used to introduce the sequences into animal cells for expression of antigen in vivo.

The above description, drawings and examples are only illustrative of preferred embodiments that achieve the objects, features and advantages of the present invention. It is not intended that the present invention be limited to the illustrated embodiments. Any modification of the present invention that comes within the spirit and scope of the following claims should be considered part of the present invention.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A purified immunogenic polypeptide, the amino acid sequence of which comprises SEQ ID NO: 8.

2. A composition comprising the immunogenic polypeptide of claim 1.

3. A diagnostic kit for detecting the presence of an antibody in a test sample, wherein said antibody is reactive to the immunogenic polypeptide of claim 1, said kit comprising the immunogenic polypeptide of claim 1.

4. A method of eliciting an immune response in an animal, said method comprising introducing the composition of claim 2 into said animal.

5. The method of claim 4, wherein said composition is administered orally, intranasally, intraperitoneally, intramuscularly, subcutaneously, or intravenously.

6. The method of claim 4, wherein said animal is a swine.

7. A method of determining whether or not an animal has an antibody reactive to the immunogenic polypeptide of claim 1, said method comprising:

providing a test sample from said animal;

contacting said test sample with said immunogenic polypeptide under conditions permissible for specific binding of said immunogenic polypeptide with said antibody; and detecting the presence or absence of said specific binding, wherein said presence of specific binding indicates that said animal has said antibody, and wherein said absence of specific binding indicates that said animal does not have said antibody.

8. The method of claim 7, wherein said test sample is a biological fluid.

9. The method of claim 8, wherein said biological fluid is selected from the group consisting of blood, nasal fluid, throat fluid, and lung fluid.

10. The method of claim 7, wherein said immunogenic polypeptide is attached to a solid support.

11. The method of claim 10, wherein said solid support is a microtiter plate, or polystyrene beads.

12. The method of claim 7, wherein said immunogenic polypeptide is labeled.

13. The method of claim 7, wherein said detecting is by radioimmunoassay (RIA), enzyme immunoassay (EIA), or enzyme-linked immunosorbent assay (ELISA).

* * * * *

UNITED STATES PATENT AND TRADEMARK OFFICE

CERTIFICATE OF CORRECTION

PATENT NO. : 7,419,806 B2
APPLICATION NO. : 10/607631
DATED : September 2, 2008
INVENTOR(S) : F. Chris Minion It is certified that error appears in the above-identified patent and that said Letters Patent is hereby corrected as shown below:

Title Page, Item [74] Attorney, Agent, or Firm, please delete “Ricahrdson” and insert --Richardson-- therefor.

Signed and Sealed this

Seventh Day of July, 2009

JOHN DOLL
*Acting Director of the United States Patent and Trademark Office*

SEQUENCE LISTING

```
<160> NUMBER OF SEQ ID NOS: 42

<210> SEQ ID NO 1
<211> LENGTH: 3029
<212> TYPE: DNA
<213> ORGANISM: Mycoplasma hyopneumoniae

<400> SEQUENCE: 1

atgaaaaaaa tacctaattt taaaggattt tttaataaac cagcaaaaat tgtaactagc     60

attttgcttc taagtggtat tataactatt tcaactgcaa ttcctttagg tatttggtca    120

tataatcgcg cttattatca aaaattaaat gaaaaatcac aaaatttaag tattagtcaa    180

actgaaaatc cctttgaaaa taatcttgga aaattctttg ataatttatt cattagtaat    240

caattcaaag aattatcagc tagtacagca tttgaattag caaaaagcaa gatttataat    300
```

-continued

```
cttgaccttt taacgttaat taatcttgat aaactatacc aaaaaaatta ccaaattagt    360
tatgatctaa gtaatgcaac agcaagtgga actgcaatta aaaatattgt attttttata    420
agaactagcg atcaacggca aatttttca aaagcagttg aaattaaagg tttttctgat    480
aaaaatattg aaaaaaatct tgctaaattt gaaattgaag aaaaaaaatc atcaatttca    540
attaaaccgc aaaatttttt aagttttgct gagtttagca aggaattaca aaatcaattt    600
attaaaacta gcaaaaccca aaaacaaaca tttattgctt ttgaagaggc gcttattcaa    660
cttggaggtt cgtataattt agttaacagt ctcggcttac caacttttat tcataaaggg    720
caaattttag aaccaaaaat ttttgataat aatcttaatt ttacaaacca agggaataaa    780
aattacctta attttatctt cacaaatgaa ggaaaaaaaa cagaaattcc cttagaaatt    840
aacggaataa cccctgattt agagattaaa aatgaaataa ttaagtgaat aaaagcggaa    900
ctagaagaaa aaatcaagct caaggaaagt attcaagctg aattaattag ggaaaattta    960
tcacttgcaa aatcatttta tgttgataaa aataataatc ctttgatatc aacaacaaaa   1020
aattttgaaa acttatttga ttatgtacaa agcgagcatc taattaatac taataaaata   1080
aaaaattata tcacaaacat aaattttaaa atcaaaaaaa atagtgaaat acctgcttta   1140
gaacttaata atttgctaaa agatgataaa attcggcttg aataaatgtt gatatctcaa   1200
agtgagtcca acaaaaacta attaaaattt taaattttaa gtttgattgg gacctaaaac   1260
cagacctgaa tcagtatgcc aggatttttg cacaaaatct acccgagcca aaatctgagg   1320
tattcttact aaaaaaagat gaaaattcag cagcgtgaac tagtaaaaaa ctagtaaata   1380
taataaataa aattaaggaa tttaacaatg aattagaccc agaaaatcct gatataaagc   1440
tagttagcca actttattta cttgattttg gcaaaattgg tgatgaaatt gctatagaaa   1500
attataaaag agaattaata ataactgcta aaatccttaa aaatcaacta gttaaagtcc   1560
aagaatttag tgatgatcag gttaataaag cacaaaacaa tgaaaaaagt ttaggaaaag   1620
caatttgtaa agtgcttaat attcagcgta atttaataaa tgatgatata agctctgatt   1680
ttatccttga taataaggaa ggtgatttta ctatcgaatt tagtctaatt tcaaataaaa   1740
ataagcaaaa attagccaca agaaagatta aaatttcaaa tattgtcagt tctgaaatga   1800
gcgcttttga tgatgcagct aaattttatc caactttttt tcttgatggc aagtcatctt   1860
tttcaaaatc agacaataaa aaaggctatg aaattataga tttatctgat aataatattc   1920
attttgagga tgatttagat agtaaaaatc aactaactca agaaggtttt aaactaacaa   1980
atccgattaa atttcagcaa aaccaatcaa aaacaaaaga aaatattgcc agaacagtca   2040
atataagtag cccaagtttc aaatcagcac cattttcacg gcttgattca gggctaattt   2100
atttagcatt taaaccaaaa aatatcaatg actataaaaa acattaccta cttgcagact   2160
cagatggaaa cggtcttttt attcaaaaga ttaaaaattt taaatttata aataaaaata   2220
ccacaatcca agggattgca ggactaaaaa ctgaaaaaac tacgcaaaat tcggatatta   2280
cctttatcaa acccgaaaat ttagaccaaa aaaaaaaaga tgaaaaaaaa caaaaacaag   2340
ttgatggtta ttttatcgga cttgacttta aacagataaa aaattttaaa tcatttcagt   2400
catatttgta ccagaacaaa aaaagctatt attccttagc taatttattc ccacctgaat   2460
taattgataa gcaagcagta attcttgggc ctaattcctg aaagccaata aaatatttta   2520
gcgctgaaat aaatcaaaat ttagacaatc tagccatagt tgaacttgca aatcgaattg   2580
gcgaaaatcg tttttatcgc caggaactaa gaaattctag tccttttca cttgaaaaaa   2640
gtaaagaaat aatcgaagaa gaccaagata ttgtccttga aattatcaaa actccgtgat   2700
```

-continued

```
cagttgaaat tagtgctttt tcatcatcaa attatcaact aaattcaaaa acatcactta   2760

atttaaatgg aaaaactatc tataatatta accctgtaag tcaaaaatgg tcaccatttc   2820

cgaattatct aaatcttgac tgggcccaaa ttgggccaaa tccaaaaaaa acaacggata   2880

aaaatggttc taacaacgaa aaaattaaca aaaatagcag cataaattta aaaggaatag   2940

cagtttataa cgatccagaa ttaacaacaa agacaagaaa ttttgcccgc gatcaaataa   3000

gaaacgcctt tattaaagca tatataaaa                                     3029


<210> SEQ ID NO 2
<211> LENGTH: 1009
<212> TYPE: PRT
<213> ORGANISM: Mycoplasma hyopneumoniae

<400> SEQUENCE: 2

Met Lys Lys Ile Pro Asn Phe Lys Gly Phe Phe Asn Lys Pro Ala Lys
 1               5                  10                  15

Ile Val Thr Ser Ile Leu Leu Leu Ser Gly Ile Ile Thr Ile Ser Thr
            20                  25                  30

Ala Ile Pro Leu Gly Ile Trp Ser Tyr Asn Arg Ala Tyr Tyr Gln Lys
        35                  40                  45

Leu Asn Glu Lys Ser Gln Asn Leu Ser Ile Ser Gln Thr Glu Asn Pro
    50                  55                  60

Phe Glu Asn Asn Leu Gly Lys Phe Phe Asp Asn Leu Phe Ile Ser Asn
65                  70                  75                  80

Gln Phe Lys Glu Leu Ser Ala Ser Thr Ala Phe Glu Leu Ala Lys Ser
                85                  90                  95

Lys Ile Tyr Asn Leu Asp Leu Leu Thr Leu Ile Asn Leu Asp Lys Leu
            100                 105                 110

Tyr Gln Lys Asn Tyr Gln Ile Ser Tyr Asp Leu Ser Asn Ala Thr Ala
        115                 120                 125

Ser Gly Thr Ala Ile Lys Asn Ile Val Phe Phe Ile Arg Thr Ser Asp
    130                 135                 140

Gln Arg Gln Ile Phe Ser Lys Ala Val Glu Ile Lys Gly Phe Ser Asp
145                 150                 155                 160

Lys Asn Ile Glu Lys Asn Leu Ala Lys Phe Glu Ile Asp Glu Lys Lys
                165                 170                 175

Ser Ser Ile Ser Ile Lys Pro Gln Asn Phe Leu Ser Phe Ala Glu Phe
            180                 185                 190

Ser Lys Glu Leu Gln Asn Gln Phe Ile Lys Thr Ser Lys Thr Gln Lys
        195                 200                 205

Gln Thr Phe Ile Ala Phe Glu Glu Ala Leu Ile Gln Leu Gly Gly Ser
    210                 215                 220

Tyr Asn Leu Val Asn Ser Leu Gly Leu Pro Thr Phe Ile His Lys Gly
225                 230                 235                 240

Gln Ile Leu Glu Pro Lys Ile Phe Asp Asn Asn Leu Asn Phe Thr Asn
                245                 250                 255

Gln Gly Asn Lys Asn Tyr Leu Asn Phe Ile Phe Thr Asn Glu Gly Lys
            260                 265                 270

Lys Thr Glu Ile Pro Leu Glu Ile Asn Gly Ile Thr Pro Asp Leu Glu
        275                 280                 285

Ile Lys Asn Glu Ile Ile Lys Trp Ile Lys Ala Glu Leu Glu Glu Lys
    290                 295                 300

Ile Lys Leu Lys Glu Ser Ile Gln Ala Glu Leu Ile Arg Glu Asn Leu
```

-continued

```
305                 310                 315                 320

Ser Leu Ala Lys Ser Phe Tyr Val Asp Lys Asn Asn Asn Pro Leu Ile
                325                 330                 335

Ser Thr Thr Lys Asn Phe Glu Asn Leu Phe Asp Tyr Val Gln Ser Glu
            340                 345                 350

His Leu Ile Asn Thr Asn Lys Ile Lys Asn Tyr Ile Thr Asn Ile Asn
        355                 360                 365

Phe Lys Ile Lys Lys Asn Ser Glu Ile Pro Ala Leu Glu Leu Asn Asn
    370                 375                 380

Leu Leu Lys Asp Asp Lys Ile Arg Leu Glu Ile Asn Val Asp Ile Ser
385                 390                 395                 400

Lys Trp Val Gln Gln Lys Leu Ile Lys Ile Leu Asn Phe Lys Phe Asp
                405                 410                 415

Trp Asp Leu Lys Pro Asp Leu Asn Gln Tyr Ala Arg Ile Phe Ala Gln
            420                 425                 430

Asn Leu Pro Glu Pro Lys Ser Glu Val Phe Leu Leu Lys Lys Asp Glu
        435                 440                 445

Asn Ser Ala Ala Trp Thr Ser Lys Lys Leu Val Asn Ile Ile Asn Lys
    450                 455                 460

Ile Lys Glu Phe Asn Asn Glu Leu Asp Pro Glu Asn Pro Asp Ile Lys
465                 470                 475                 480

Leu Val Ser Gln Leu Tyr Leu Leu Asp Phe Gly Lys Ile Gly Asp Glu
                485                 490                 495

Ile Ala Ile Glu Asn Tyr Lys Arg Glu Leu Ile Ile Thr Ala Lys Ile
            500                 505                 510

Leu Lys Asn Gln Leu Val Lys Val Gln Glu Phe Ser Asp Asp Gln Val
        515                 520                 525

Asn Lys Ala Gln Asn Asn Glu Lys Ser Leu Gly Lys Ala Ile Trp Lys
    530                 535                 540

Val Leu Asn Ile Gln Arg Asn Leu Ile Asn Asp Asp Ile Ser Ser Asp
545                 550                 555                 560

Phe Ile Leu Asp Asn Lys Glu Gly Asp Phe Thr Ile Glu Phe Ser Leu
                565                 570                 575

Ile Ser Asn Lys Asn Lys Gln Lys Leu Ala Thr Arg Lys Ile Lys Ile
            580                 585                 590

Ser Asn Ile Val Ser Ser Glu Met Ser Ala Phe Asp Asp Ala Ala Lys
        595                 600                 605

Phe Tyr Pro Thr Phe Phe Leu Asp Gly Lys Ser Ser Phe Ser Lys Ser
    610                 615                 620

Asp Asn Lys Lys Gly Tyr Glu Ile Ile Asp Leu Ser Asp Asn Asn Ile
625                 630                 635                 640

His Phe Glu Asp Asp Leu Asp Ser Lys Asn Gln Leu Thr Gln Glu Gly
                645                 650                 655

Phe Lys Leu Thr Asn Pro Ile Lys Phe Gln Gln Asn Gln Ser Lys Thr
            660                 665                 670

Lys Glu Asn Ile Ala Arg Thr Val Asn Ile Ser Ser Pro Ser Phe Lys
        675                 680                 685

Ser Ala Pro Phe Ser Arg Leu Asp Ser Gly Leu Ile Tyr Leu Ala Phe
    690                 695                 700

Lys Pro Lys Asn Ile Asn Asp Tyr Lys Lys His Tyr Leu Leu Ala Asp
705                 710                 715                 720

Ser Asp Gly Asn Gly Leu Phe Ile Gln Lys Ile Lys Asn Phe Lys Phe
                725                 730                 735
```

-continued

Ile Asn Lys Asn Thr Thr Ile Gln Gly Ile Ala Gly Leu Lys Thr Glu
740 745 750

Lys Thr Thr Gln Asn Ser Asp Ile Thr Phe Ile Lys Pro Glu Asn Leu
755 760 765

Asp Gln Lys Asn Lys Asp Glu Thr Gln Gln Lys Gln Val Asp Gly Tyr
770 775 780

Phe Ile Gly Leu Asp Phe Lys Gln Ile Lys Asn Phe Lys Ser Phe Gln
785 790 795 800

Ser Tyr Leu Tyr Gln Asn Lys Lys Ser Leu Tyr Ser Leu Ala Asn Leu
805 810 815

Phe Pro Pro Glu Leu Ile Asp Lys Gln Ala Val Ile Leu Gly Pro Asn
820 825 830

Ser Trp Lys Pro Ile Lys Asn Phe Ser Ala Glu Ile Asn Gln Asn Leu
835 840 845

Asp Asn Leu Ala Ile Val Glu Leu Ala Asn Arg Ile Gly Glu Asn Arg
850 855 860

Phe Tyr Arg Gln Glu Leu Arg Asn Ser Ser Pro Phe Ser Leu Glu Lys
865 870 875 880

Ser Lys Glu Ile Ile Glu Glu Asp Gln Asp Ile Val Leu Glu Ile Ile
885 890 895

Lys Thr Pro Trp Ser Val Glu Ile Ser Ala Phe Ser Ser Ser Asn Tyr
900 905 910

Gln Leu Asn Ser Lys Thr Ser Leu Asn Leu Asn Gly Lys Thr Ile Tyr
915 920 925

Asn Ile Asn Pro Val Ser Gln Lys Trp Ser Pro Phe Pro Asn Tyr Leu
930 935 940

Asn Leu Asp Trp Ala Gln Ile Gly Pro Asn Pro Lys Lys Thr Thr Asp
945 950 955 960

Lys Asn Gly Ser Asn Asn Glu Lys Ile Asn Lys Asn Ser Ser Ile Ile
965 970 975

Leu Lys Gly Ile Ala Val Tyr Asn Asp Pro Glu Leu Thr Thr Lys Thr
980 985 990

Arg Asn Phe Ala Arg Asp Gln Ile Arg Asn Ala Phe Ile Lys Ala Tyr
995 1000 1005

Ile

<210> SEQ ID NO 3
<211> LENGTH: 3096
<212> TYPE: DNA
<213> ORGANISM: Mycoplasma hyopneumoniae

<400> SEQUENCE: 3
atgcaggcta atttgattgg cagatttatc aaaaataaaa aagcaatttt ggtactagct 60
tcaacttttg ctgggttaat tttatttact acttctgtcg gaattagttt aacaattaaa 120
tataatggtt ctcacccgcg ggcaaaagtt aatgaatttg cacaaaaaat tagttttgtt 180
agttttaaac ctgagcaaat tagtaaaaat agtaatttct gaaaaataaa agaaaaattg 240
ttttccggtg atcagcttaa aaaagaaata aatcttgaag agtatctcca attttatatt 300
tttgataaaa attctaatga tttggttaaa ttctcaaaag attcaaatcc tttttctatt 360
gaatttgaat ttagtgattt aaaatttgat gatttaaacc aaaattttaa tcttaaattt 420
cgtgttaggc aaaaacaaaa aaataatcaa tatgcatatt cggatttttt cagccaacca 480
attacatttt atgaatcaaa taaattttta aaagcagatt ttaactttgt tcttcaaaaa 540

-continued

```
atgtttcgcc aaattaatga aaatatttta aatataggta attttaccac aaatttttct    600
gatcaaacta gtaaaaaaaa attaaaaaag ttatacagag caattgattt tgcgcaagaa    660
gttaataaaa ttgaaaatcc aaacgaggtt gaggtcaaaa taaatgaaat tttccctgaa    720
ttatctaact tgattttaca agcacgcgaa tcgaaagata ataaaattgg aaaaacagaa    780
aatccgattt ttagtcttaa atttataaaa aataaaacta ataatcaatt tgtaaatcta    840
caagataata tcccaactat gtatcttgag gcaaaattaa ctgatcaagc cgcaaaaatg    900
ttaggtgata ttggtcaaaa ctttagcgaa aaaatctttg aaattagatt tgaaactaat    960
gataaaaaat cattattttt caatgttgag aatttttttc aaaatattaa actaaaacca   1020
ctaaaattta acactgaaga aaaagacgga aaattaataa taactaaact gaatcctttt   1080
gacatatttt caaaaattaa atccggaatt ttatctgcca atactaacca aaattacata   1140
aaaggggtta ttaattcttt attagaagag gatttagctc tagattttgg gccgacttca   1200
aaactaattc cacaaaatca aaacggaatt agttttgaaa ttatccaaca aaatgctaaa   1260
ttaaaaaatg aaaatgataa ttatataatt gaaattccct ataaaatttt ccttagagaa   1320
tccttattta aacctggttc acaaaaaatt atctatgaaa aagagttgtt tttaagtatt   1380
ggcggctttg gtatatcaaa taaaaatggt caaaatctaa taattccagg aagccagaaa   1440
gctttaattt atcggagaaa ttcacttttt aatgatgagg aaagtcctga aaataaattt   1500
atttcaactt ttggtcaacc ggtcatttcg aataatccct taaaaaaaga agaaattgat   1560
aatttattat tgcaacaaga ttataaaggt ttagaaagac agctaaattc attatcacgg   1620
tataatttta attttgataa ttttgaggcc aaagttcggg cttgatctgg taagacatac   1680
ttacctagtt taacagaaat tgcaaatttt cgattaaatc aacaaaaaat tgatataaat   1740
tcacaaaatc aagagcaaaa aattgaacta aaaacactac attcacaaag tttttttata   1800
aatccttcgg atgtaacagc ttttttgct gatttaattc agaaaaaacc aagccaaata    1860
gcaaatagtt ttttcttaat tgcaaaggct tttggacttt taaatcaaaa tcggactgct   1920
tcgcaaattt ttaataacct ggctggagaa aatatctttg aagctagttc aaaaattgat   1980
tttgataata aaactacaaa tattttaagt tttaataatc atttcgctga tttttataat   2040
caagggtttt tttcatccct ttttcttcca aaatcaataa aagataaatt caataatcta   2100
aaaagcaagt caatttctga tgtaattagt attttagaag accaagaact ttttaaagaa   2160
acagctagaa aatttacaag acaacaaatt gaggaaaacc taaaatcaag tgttaaattc   2220
acaacattgg ccgaccttct tttagctttt tattataagg ctagtcaact tgataatttt   2280
ttagggtgaa caaaattaga taccaattta gattatcaaa ttgtgtttca aaaagaaaat   2340
gaaatttcaa aagctcgtta tgattctgaa attcagaagc taaaaaaacc cgaattaaat   2400
tctttagaaa aacaggaaaa cttaaataaa aattctgaaa ttcaaccaga atctaaaaat   2460
ttagactctg ataataacat aaaaaaatca ataaatggaa atttagaaaa agataatact   2520
tataatgcca atgttgataa tgaatatcta acattaaatt tttactatat tattggtgat   2580
tctagtcaga aaaaattttt ctttcaaagc ccaattcaaa aaattttaat aaatttctca   2640
actcaaaaaa ttgatgaaaa ttctaaaata caagaaaaat tcgataaggt agttgaaagt   2700
gttccggctg atttgttaaa ttatagtgtc agtgaagaaa attttaaaaa aattaaggaa   2760
aaattaacaa ataagcattc acctgaacca aaaaataatg acaataataa cgatttagat   2820
ttatatttta aagaaacttc cataaatatt gataaaatta gttcttattt taaagaacaa   2880
```

-continued

```
tttcccaaag aggagacaaa atttttactt gaaccaagtt ttgaaaactc actaaatacg   2940

gataaactaa cctttttaat aagtttttat cttaataaga aggataaaaa tcccaaagat   3000

ttaaaagctg ataataaaaa tgatgaaaat agcccgataa atccaattat tgcaaggcag   3060

aaattaaaaa ttataataac aaaaaattct aaaaat                             3096


<210> SEQ ID NO 4
<211> LENGTH: 1032
<212> TYPE: PRT
<213> ORGANISM: Mycoplasma hyopneumoniae

<400> SEQUENCE: 4

Met Gln Ala Asn Leu Ile Gly Arg Phe Ile Lys Asn Lys Lys Ala Ile
 1               5                  10                  15

Leu Val Leu Ala Ser Thr Phe Ala Gly Leu Ile Leu Phe Thr Thr Ser
            20                  25                  30

Val Gly Ile Ser Leu Thr Ile Lys Tyr Asn Gly Ser His Pro Arg Ala
        35                  40                  45

Lys Val Asn Glu Phe Ala Gln Lys Ile Ser Phe Val Ser Phe Lys Pro
    50                  55                  60

Glu Gln Ile Ser Lys Asn Ser Asn Phe Trp Lys Ile Lys Glu Lys Leu
65                  70                  75                  80

Phe Ser Gly Asp Gln Leu Lys Lys Glu Ile Asn Leu Glu Glu Tyr Leu
                85                  90                  95

Gln Phe Tyr Ile Phe Asp Lys Asn Ser Asn Asp Leu Val Lys Phe Ser
            100                 105                 110

Lys Asp Ser Asn Pro Phe Ser Ile Glu Phe Glu Phe Ser Asp Leu Lys
        115                 120                 125

Phe Asp Asp Leu Asn Gln Asn Phe Asn Leu Lys Phe Arg Val Arg Gln
    130                 135                 140

Lys Gln Lys Asn Asn Gln Tyr Ala Tyr Ser Asp Phe Phe Ser Gln Pro
145                 150                 155                 160

Ile Thr Phe Tyr Glu Ser Asn Lys Phe Leu Lys Ala Asp Phe Asn Phe
                165                 170                 175

Val Leu Gln Lys Met Phe Arg Gln Ile Asn Glu Asn Ile Leu Asn Ile
            180                 185                 190

Gly Asn Phe Thr Thr Asn Phe Ser Asp Gln Thr Ser Lys Lys Lys Leu
        195                 200                 205

Lys Lys Leu Tyr Arg Ala Ile Asp Phe Ala Gln Glu Val Asn Lys Ile
    210                 215                 220

Glu Asn Pro Asn Glu Val Glu Val Lys Ile Asn Glu Ile Phe Pro Glu
225                 230                 235                 240

Leu Ser Asn Leu Ile Leu Gln Ala Arg Glu Ser Lys Asp Asn Lys Ile
                245                 250                 255

Gly Lys Thr Glu Asn Pro Ile Phe Ser Leu Lys Phe Ile Lys Asn Lys
            260                 265                 270

Thr Asn Asn Gln Phe Val Asn Leu Gln Asp Asn Ile Pro Thr Met Tyr
        275                 280                 285

Leu Glu Ala Lys Leu Thr Asp Gln Ala Ala Lys Met Leu Gly Asp Ile
    290                 295                 300

Gly Gln Asn Phe Ser Glu Lys Ile Phe Glu Ile Arg Phe Glu Thr Asn
305                 310                 315                 320

Asp Lys Lys Ser Leu Phe Phe Asn Val Glu Asn Phe Phe Gln Asn Ile
                325                 330                 335
```

-continued

```
Lys Leu Lys Pro Leu Lys Phe Asn Thr Glu Glu Lys Asp Gly Lys Leu
        340                 345                 350

Ile Ile Thr Lys Leu Asn Pro Phe Asp Ile Phe Ser Lys Ile Lys Ser
            355                 360                 365

Gly Ile Leu Ser Ala Asn Thr Asn Gln Asn Tyr Ile Lys Gly Val Ile
    370                 375                 380

Asn Ser Leu Leu Glu Glu Asp Leu Ala Leu Asp Phe Gly Pro Thr Ser
385                 390                 395                 400

Lys Leu Ile Pro Gln Asn Gln Asn Gly Ile Ser Phe Glu Ile Ile Gln
                405                 410                 415

Gln Asn Ala Lys Leu Lys Asn Glu Asn Asp Asn Tyr Ile Ile Glu Ile
            420                 425                 430

Pro Tyr Lys Ile Phe Leu Arg Glu Ser Leu Phe Lys Pro Gly Ser Gln
        435                 440                 445

Lys Ile Ile Tyr Glu Lys Glu Leu Phe Leu Ser Ile Gly Gly Phe Gly
    450                 455                 460

Ile Ser Asn Lys Asn Gly Gln Asn Leu Ile Ile Pro Gly Ser Gln Lys
465                 470                 475                 480

Ala Leu Ile Tyr Arg Arg Asn Ser Leu Phe Asn Asp Glu Glu Ser Pro
                485                 490                 495

Glu Asn Lys Phe Ile Ser Thr Phe Gly Gln Pro Val Ile Ser Asn Asn
            500                 505                 510

Pro Leu Lys Lys Glu Glu Ile Asp Asn Leu Leu Leu Gln Gln Asp Tyr
        515                 520                 525

Lys Gly Leu Glu Arg Gln Leu Asn Ser Leu Ser Arg Tyr Asn Phe Asn
    530                 535                 540

Phe Asp Asn Phe Glu Ala Lys Val Arg Ala Trp Ser Gly Lys Thr Tyr
545                 550                 555                 560

Leu Pro Ser Leu Thr Glu Ile Ala Asn Phe Arg Leu Asn Gln Gln Lys
                565                 570                 575

Ile Asp Ile Asn Ser Gln Asn Gln Glu Gln Lys Ile Glu Leu Lys Thr
            580                 585                 590

Leu His Ser Gln Ser Phe Phe Ile Asn Pro Ser Asp Val Thr Ala Phe
        595                 600                 605

Phe Ala Asp Leu Ile Gln Lys Lys Pro Ser Gln Ile Ala Asn Ser Phe
    610                 615                 620

Phe Leu Ile Ala Lys Ala Phe Gly Leu Leu Asn Gln Asn Arg Thr Ala
625                 630                 635                 640

Ser Gln Ile Phe Asn Asn Leu Ala Gly Glu Asn Ile Phe Glu Ala Ser
                645                 650                 655

Ser Lys Ile Asp Phe Asp Asn Lys Thr Thr Asn Ile Leu Ser Phe Asn
            660                 665                 670

Asn His Phe Ala Asp Phe Tyr Asn Gln Gly Phe Phe Ser Ser Leu Phe
        675                 680                 685

Leu Pro Lys Ser Ile Lys Asp Lys Phe Asn Asn Leu Lys Ser Lys Ser
    690                 695                 700

Ile Ser Asp Val Ile Ser Ile Leu Glu Asp Gln Glu Leu Phe Lys Glu
705                 710                 715                 720

Thr Ala Arg Lys Phe Thr Arg Gln Gln Ile Glu Glu Asn Leu Lys Ser
                725                 730                 735

Ser Val Lys Phe Thr Thr Leu Ala Asp Leu Leu Leu Ala Phe Tyr Tyr
            740                 745                 750

Lys Ala Ser Gln Leu Asp Asn Phe Leu Gly Trp Thr Lys Leu Asp Thr
```

-continued

```
        755                 760                 765

Asn Leu Asp Tyr Gln Ile Val Phe Gln Lys Glu Asn Glu Ile Ser Lys
    770                 775                 780

Ala Arg Tyr Asp Ser Glu Ile Gln Lys Leu Lys Lys Pro Glu Leu Asn
785                 790                 795                 800

Ser Leu Glu Lys Gln Glu Asn Leu Asn Lys Asn Ser Glu Ile Gln Pro
                805                 810                 815

Glu Ser Lys Asn Leu Asp Ser Asp Asn Asn Ile Lys Lys Ser Ile Asn
            820                 825                 830

Gly Asn Leu Glu Lys Asp Asn Thr Tyr Asn Ala Asn Val Asp Asn Glu
        835                 840                 845

Tyr Leu Thr Leu Asn Phe Tyr Tyr Ile Ile Gly Asp Ser Ser Gln Lys
    850                 855                 860

Lys Phe Phe Phe Gln Ser Pro Ile Gln Lys Ile Leu Ile Asn Phe Ser
865                 870                 875                 880

Thr Gln Lys Ile Asp Glu Asn Ser Lys Ile Gln Glu Lys Phe Asp Lys
                885                 890                 895

Val Val Glu Ser Val Pro Ala Asp Leu Leu Asn Tyr Ser Val Ser Glu
            900                 905                 910

Glu Asn Phe Lys Lys Ile Lys Glu Lys Leu Thr Asn Lys His Ser Pro
        915                 920                 925

Glu Pro Lys Asn Asn Asp Asn Asn Asn Asp Leu Asp Leu Tyr Phe Lys
    930                 935                 940

Glu Thr Ser Ile Asn Ile Asp Lys Ile Ser Ser Tyr Phe Lys Glu Gln
945                 950                 955                 960

Phe Pro Lys Glu Glu Thr Lys Phe Leu Leu Glu Pro Ser Phe Glu Asn
                965                 970                 975

Ser Leu Asn Thr Asp Lys Leu Thr Phe Leu Ile Ser Phe Tyr Leu Asn
            980                 985                 990

Lys Lys Asp Lys Asn Pro Lys Asp Leu Lys Ala Asp Asn Lys Asn Asp
        995                 1000                1005

Glu Asn Ser Pro Ile Asn Pro Ile Ile Ala Arg Gln Lys Leu Lys Ile
    1010                1015                1020

Ile Ile Thr Lys Asn Ser Lys Asn
1025                1030


<210> SEQ ID NO 5
<211> LENGTH: 3582
<212> TYPE: DNA
<213> ORGANISM: Mycoplasma hyopneumoniae

<400> SEQUENCE: 5

atgaaccaat ttgacgaaaa agagaaacaa cataataaag caaaagcaat tctttcaacc      60

ggattttcgg ttacatcaat tgcaactaca gttgtagcag tcccaattgg actaacaatt     120

tttgagaaat catttagttc ccaagtttca ggaggagtcg ataagaacaa agttgtggat     180

ttaaaatcag attcagatca aatcttctca gaagaagatt ttataagagc agttgagaat     240

cttaaacttt ttgataaata tagacatcta acagcaagaa tggcattagg tcttgccagg     300

gaagcagcta atgcctttaa ctttttagat acttacgact acaccccaat tacaaagcat     360

tcatttaaga tttctttgga tatttccgat gcctttgcgg ctaataaaga agtaaaagcg     420

gtagtagtta gtgcatattc ccaaaaatat caagttacct attcaagact aacttctcta     480

aaaggttgaa aagaagaaga tgattttggc gatgatatta tagattatca aattaatcaa     540
```

-continued

```
gagctttcag gtctatcact ttcttcccta gcccctgaaa gcgcgcatct tttagcctca    600
gaaatggctt ttcggcttga taatgacttt caagttgcat ataaaaaaac aggatcaaga    660
gccgaggctt ttcgccaggc cttgataaaa aattatcttg gttataactt agttaaccgc    720
caaggtttgc ccactatgct ccaaaagggt tatgtgctag cccccaaaac aattgaaaat    780
aaaaatgcaa gcgaagaaaa attagtaaat ataaatgaaa atgaccgtgc aagggttaat    840
aaactacaaa aagtagaaaa tctagccttt aaaaacttaa gcgatccaaa tggaacgctt    900
tctattactt ttgaactctg agatccaaat ggtaaattag tatccgaata cgattttaaa    960
attaagggaa tcaaaaaact tgattttgat cttaaaaaac aagaggaaaa agtacttcaa   1020
aaggtaactg aatttgttga gattaaacct tatgttcaat taggtttaat ccgtgataat   1080
ttatcattgt ctgaaattat ctataaaagt gataataatc cggagtatct taggaaaata   1140
ttagctaaac taaaagaaca caataacaac aaaagggtgg ataataatac atccactact   1200
aaatttcaag aagaggatct taaaaacgaa ccaaattcta atggatcaga acaagattct   1260
ttcgagaaag caaaggaaaa tttccttagt ttttttgatc taagatcgag actaattcca   1320
attcccgatc ttcctttata ttatcttaaa gttaattcaa ttaattttga tagaaatatt   1380
gaagaaaatg aaaaagaaaa attattaaaa aatgaacaag tagtactcaa agtagatttt   1440
agtcttaaaa aagttgttag cgatattaga gccccttatt tagtttctag tcaggttaga   1500
tcaaattatc ccccggtttt gaaagcttcg ctagcaaaaa taggtaaggg gtcaaattca   1560
aaagttgtcc ttttagatct tggaaattta tcttcaagat ttaaagttca acttgattat   1620
agtgcaaaac aaagagaaat aattaatact ttattaaagg aaaatccaga aagagaaaaa   1680
gaattacaag ctaaaattga aagtaagacg tttagtccaa tagatcttaa caatgatgat   1740
ctattagcaa tcgaatttca atatgaggat aaccctgaag gagattgaat aactttaggg   1800
agaatggaaa agttagtcaa agaggttatc caatataaaa aggaaggtaa aaccttccta   1860
gatgatgaag tcgctaaaac actttattat ttagatttcc atcatctacc tcaaagtaaa   1920
aaagacctcg aagaatataa agaaaaacac aaaaacaagt ttattaacga aataaaacct   1980
gctacaccag caagtcaagc aaaaccagat caagcaaaaa atgaaaaaga agtaaaacct   2040
gaatcagccc aagcagaatc ttcatcttca aattctaatg attctaatag taaaaccact   2100
tcttcttcaa gtatgatggc gggtacaacc caaacaaata attcctctac agaaacaaca   2160
aattcaaatt cagcaacaac aacttcaaca acaacacaag cagcagcaac ttcagcctct   2220
tcggctaaag taaaaacaac taaattccaa gaacaagtaa aagaacaaga acaaaaacaa   2280
gaaaaagcaa aagaaactaa ccaattatta gatactaaaa gaaataaaga agactcaggg   2340
cttggattaa ttctttggga tttcctagta aattcaaaat ataaaactct accaggaact   2400
acctgagatt tccatgttga accagataat ttcaatgatc gtctaaaaat aacagcgatt   2460
ctaaaagaaa atacatccca ggcaaagtca aatccagata gtaaaaacct aacttcccta   2520
tcgcgaaacc ttataataaa aggggttatg gctaataaat acattgacta cttagtccaa   2580
gaagatccag tacttcttgt agattataca agaagaaacc agattaaaac cgaaagagaa   2640
ggacaactaa tttgaaatca gttagcttcc cctcaaatgg catctcctga aactagtccc   2700
gaaaaggcta agctcgagat caccgaggaa ggactccgtg ttaaaaaagg tggcactaag   2760
ataaaagaga caagaaaaag cacaaccagc aatgctaaaa gcaatactaa ctccaaacca   2820
aataaaaagt tagtcctact aaaagggtct ataaaaaacc cgggaacaaa aaaggaatga   2880
attcttgtag gatctgggaa taacgccacc aaaaacggaa gctccagcaa caactccaat   2940
```

-continued

```
acccaaatat gaataaccag actaggaaca tctgttggtt cattaaaaac cgaaggtgag   3000

acagtccttg gaatttcaaa taataattcc caaggtgaag ttctctgaac tactattaaa   3060

tccaaactcg aaaacgaaaa tcaatcagat aacaatcaaa tccaatactc cccaagtacg   3120

catagtttaa caaccaattc tcgatcaaat acccaacaat cagggcgaaa tcaaattaaa   3180

attacaaaca ctcaaagaaa aacaactact tcgccggccc aaagcccaat acaaaatcct   3240

gatccgaacc aaattgatgt aagacttggt ctactagtac aagacaaaaa acttcatctt   3300

tggtggattg ctaatgatag ctctgatgag cctgagcata taacaattga tttcgctgaa   3360

gggacaaaat ttaattatga tgatttaaat tatgtcggag ggcttttaaa aaatactaca   3420

aataatacca atacccaagc ccaagacgat gaaggtgatg gatatctggc cctaaaagga   3480

ttagggatct atgaatttcc tgatgatgaa agtattgatc aagccgctac tgttgaaaaa   3540

gcagagagat tatataaaca ctttatgggg ctatttaggg aa                      3582


<210> SEQ ID NO 6
<211> LENGTH: 1194
<212> TYPE: PRT
<213> ORGANISM: Mycoplasma hyopneumoniae

<400> SEQUENCE: 6

Met Asn Gln Phe Asp Glu Lys Glu Lys Gln His Asn Lys Ala Lys Ala
 1               5                  10                  15

Ile Leu Ser Thr Gly Phe Ser Val Thr Ser Ile Ala Thr Thr Val Val
            20                  25                  30

Ala Val Pro Ile Gly Leu Thr Ile Phe Glu Lys Ser Phe Ser Ser Gln
        35                  40                  45

Val Ser Gly Gly Val Asp Lys Asn Lys Val Val Asp Leu Lys Ser Asp
    50                  55                  60

Ser Asp Gln Ile Phe Ser Glu Glu Asp Phe Ile Arg Ala Val Glu Asn
65                  70                  75                  80

Leu Lys Leu Phe Asp Lys Tyr Arg His Leu Thr Ala Arg Met Ala Leu
                85                  90                  95

Gly Leu Ala Arg Glu Ala Ala Asn Ala Phe Asn Phe Leu Asp Thr Tyr
            100                 105                 110

Asp Tyr Thr Pro Ile Thr Lys His Ser Phe Lys Ile Ser Leu Asp Ile
        115                 120                 125

Ser Asp Ala Phe Ala Ala Asn Lys Glu Val Lys Ala Val Val Val Ser
    130                 135                 140

Ala Tyr Ser Gln Lys Tyr Gln Val Thr Tyr Ser Arg Leu Thr Ser Leu
145                 150                 155                 160

Lys Gly Trp Lys Glu Glu Asp Asp Phe Gly Asp Asp Ile Ile Asp Tyr
                165                 170                 175

Gln Ile Asn Gln Glu Leu Ser Gly Leu Ser Leu Ser Ser Leu Ala Pro
            180                 185                 190

Glu Ser Ala His Leu Leu Ala Ser Glu Met Ala Phe Arg Leu Asp Asn
        195                 200                 205

Asp Phe Gln Val Ala Tyr Lys Lys Thr Gly Ser Arg Ala Glu Ala Phe
    210                 215                 220

Arg Gln Ala Leu Ile Lys Asn Tyr Leu Gly Tyr Asn Leu Val Asn Arg
225                 230                 235                 240

Gln Gly Leu Pro Thr Met Leu Gln Lys Gly Tyr Val Leu Ala Pro Lys
                245                 250                 255
```

-continued

```
Thr Ile Glu Asn Lys Asn Ala Ser Glu Glu Lys Leu Val Asn Ile Asn
            260                 265                 270

Glu Asn Asp Arg Ala Arg Val Asn Lys Leu Gln Lys Val Glu Asn Leu
        275                 280                 285

Ala Phe Lys Asn Leu Ser Asp Pro Asn Gly Thr Leu Ser Ile Thr Phe
    290                 295                 300

Glu Leu Trp Asp Pro Asn Gly Lys Leu Val Ser Glu Tyr Asp Phe Lys
305                 310                 315                 320

Ile Lys Gly Ile Lys Lys Leu Asp Phe Asp Leu Lys Lys Gln Glu Glu
                325                 330                 335

Lys Val Leu Gln Lys Val Thr Glu Phe Val Glu Ile Lys Pro Tyr Val
            340                 345                 350

Gln Leu Gly Leu Ile Arg Asp Asn Leu Ser Leu Ser Glu Ile Ile Tyr
        355                 360                 365

Lys Ser Asp Asn Asn Pro Glu Tyr Leu Arg Lys Ile Leu Ala Lys Leu
    370                 375                 380

Lys Glu His Asn Asn Asn Lys Arg Val Asp Asn Asn Thr Ser Thr Thr
385                 390                 395                 400

Lys Phe Gln Glu Glu Asp Leu Lys Asn Glu Pro Asn Ser Asn Gly Ser
                405                 410                 415

Glu Gln Asp Ser Phe Glu Lys Ala Lys Glu Asn Phe Leu Ser Phe Phe
            420                 425                 430

Asp Leu Arg Ser Arg Leu Ile Pro Ile Pro Asp Leu Pro Leu Tyr Tyr
        435                 440                 445

Leu Lys Val Asn Ser Ile Asn Phe Asp Arg Asn Ile Glu Glu Asn Glu
    450                 455                 460

Lys Glu Lys Leu Leu Lys Asn Glu Gln Val Val Leu Lys Val Asp Phe
465                 470                 475                 480

Ser Leu Lys Lys Val Val Ser Asp Ile Arg Ala Pro Tyr Leu Val Ser
                485                 490                 495

Ser Gln Val Arg Ser Asn Tyr Pro Pro Val Leu Lys Ala Ser Leu Ala
            500                 505                 510

Lys Ile Gly Lys Gly Ser Asn Ser Lys Val Val Leu Leu Asp Leu Gly
        515                 520                 525

Asn Leu Ser Ser Arg Phe Lys Val Gln Leu Asp Tyr Ser Ala Lys Gln
    530                 535                 540

Arg Glu Ile Ile Asn Thr Leu Leu Lys Glu Asn Pro Glu Arg Glu Lys
545                 550                 555                 560

Glu Leu Gln Ala Lys Ile Glu Ser Lys Thr Phe Ser Pro Ile Asp Leu
                565                 570                 575

Asn Asn Asp Asp Leu Leu Ala Ile Glu Phe Gln Tyr Glu Asp Asn Pro
            580                 585                 590

Glu Gly Asp Trp Ile Thr Leu Gly Arg Met Glu Lys Leu Val Lys Glu
        595                 600                 605

Val Ile Gln Tyr Lys Lys Glu Gly Lys Thr Phe Leu Asp Asp Glu Val
    610                 615                 620

Ala Lys Thr Leu Tyr Tyr Leu Asp Phe His His Leu Pro Gln Ser Lys
625                 630                 635                 640

Lys Asp Leu Glu Glu Tyr Lys Glu Lys His Lys Asn Lys Phe Ile Asn
                645                 650                 655

Glu Ile Lys Pro Ala Thr Pro Ala Ser Gln Ala Lys Pro Asp Gln Ala
            660                 665                 670

Lys Asn Glu Lys Glu Val Lys Pro Glu Ser Ala Gln Ala Glu Ser Ser
```

-continued 675 680 685

Ser Ser Asn Ser Asn Asp Ser Asn Ser Lys Thr Thr Ser Ser Ser Ser
690 695 700

Met Met Ala Gly Thr Thr Gln Thr Asn Asn Ser Ser Thr Glu Thr Thr
705 710 715 720

Asn Ser Asn Ser Ala Thr Thr Thr Ser Thr Thr Thr Gln Ala Ala Ala
725 730 735

Thr Ser Ala Ser Ser Ala Lys Val Lys Thr Thr Lys Phe Gln Glu Gln
740 745 750

Val Lys Glu Gln Glu Gln Lys Gln Glu Lys Ala Lys Glu Thr Asn Gln
755 760 765

Leu Leu Asp Thr Lys Arg Asn Lys Glu Asp Ser Gly Leu Gly Leu Ile
770 775 780

Leu Trp Asp Phe Leu Val Asn Ser Lys Tyr Lys Thr Leu Pro Gly Thr
785 790 795 800

Thr Trp Asp Phe His Val Glu Pro Asp Asn Phe Asn Asp Arg Leu Lys
805 810 815

Ile Thr Ala Ile Leu Lys Glu Asn Thr Ser Gln Ala Lys Ser Asn Pro
820 825 830

Asp Ser Lys Asn Leu Thr Ser Leu Ser Arg Asn Leu Ile Ile Lys Gly
835 840 845

Val Met Ala Asn Lys Tyr Ile Asp Tyr Leu Val Gln Glu Asp Pro Val
850 855 860

Leu Leu Val Asp Tyr Thr Arg Arg Asn Gln Ile Lys Thr Glu Arg Glu
865 870 875 880

Gly Gln Leu Ile Trp Asn Gln Leu Ala Ser Pro Gln Met Ala Ser Pro
885 890 895

Glu Thr Ser Pro Glu Lys Ala Lys Leu Glu Ile Thr Glu Glu Gly Leu
900 905 910

Arg Val Lys Lys Gly Gly Thr Lys Ile Lys Glu Thr Arg Lys Ser Thr
915 920 925

Thr Ser Asn Ala Lys Ser Asn Thr Asn Ser Lys Pro Asn Lys Lys Leu
930 935 940

Val Leu Leu Lys Gly Ser Ile Lys Asn Pro Gly Thr Lys Lys Glu Trp
945 950 955 960

Ile Leu Val Gly Ser Gly Asn Asn Ala Thr Lys Asn Gly Ser Ser Ser
965 970 975

Asn Asn Ser Asn Thr Gln Ile Trp Ile Thr Arg Leu Gly Thr Ser Val
980 985 990

Gly Ser Leu Lys Thr Glu Gly Glu Thr Val Leu Gly Ile Ser Asn Asn
995 1000 1005

Asn Ser Gln Gly Glu Val Leu Trp Thr Thr Ile Lys Ser Lys Leu Glu
1010 1015 1020

Asn Glu Asn Gln Ser Asp Asn Asn Gln Ile Gln Tyr Ser Pro Ser Thr
1025 1030 1035 1040

His Ser Leu Thr Thr Asn Ser Arg Ser Asn Thr Gln Gln Ser Gly Arg
1045 1050 1055

Asn Gln Ile Lys Ile Thr Asn Thr Gln Arg Lys Thr Thr Thr Ser Pro
1060 1065 1070

Ala Gln Ser Pro Ile Gln Asn Pro Asp Pro Asn Gln Ile Asp Val Arg
1075 1080 1085

Leu Gly Leu Leu Val Gln Asp Lys Lys Leu His Leu Trp Trp Ile Ala
1090 1095 1100

-continued

Asn Asp Ser Ser Asp Glu Pro Glu His Ile Thr Ile Asp Phe Ala Glu
1105 1110 1115 1120

Gly Thr Lys Phe Asn Tyr Asp Asp Leu Asn Tyr Val Gly Gly Leu Leu
1125 1130 1135

Lys Asn Thr Thr Asn Asn Thr Asn Thr Gln Ala Gln Asp Asp Glu Gly
1140 1145 1150

Asp Gly Tyr Leu Ala Leu Lys Gly Leu Gly Ile Tyr Glu Phe Pro Asp
1155 1160 1165

Asp Glu Ser Ile Asp Gln Ala Ala Thr Val Glu Lys Ala Glu Arg Leu
1170 1175 1180

Tyr Lys His Phe Met Gly Leu Phe Arg Glu
1185 1190

<210> SEQ ID NO 7
<211> LENGTH: 5636
<212> TYPE: DNA
<213> ORGANISM: Mycoplasma hyopneumoniae

<400> SEQUENCE: 7
atgaaaaaca aaaaatcaac attactatta gccacagcgg cagcaattat tggttcaact 60
gtttttggaa cagttgttgg tttggcttca aaagttaaat atcggggtgt aaatccaact 120
caaggagtaa tatctcaatt aggactgatt gattctgttg catttaaacc ttcgattgca 180
aattttacaa gcgattatca aagtgttaaa aaagcacttt taaatgggaa aacctttgat 240
ccaaaaagtt cagaatttac tgattttgtc tcaaaatttg actttttgac taataatggg 300
agaaccgttt tggagatccc gaaaaaatat caggtggtta tctcggaatt tagccccgag 360
gatgataaag aacgttttcg tcttggattt catctaaaag aaaaacttga agatggaaat 420
atagctcaat cagcaactaa atttatttat cttttaccac ttgatatgcc caaagcggcc 480
ctgggtcaat attcttatat cgttgataaa aattttaata atttaattat ccatccttta 540
tctaattttt ctgctcaatc aataaagccg cttgcactga cccgttcaag tgattttata 600
gcaaaactta atcagtttaa caatcaggac gagctttgag tttatctgga aaaattcttt 660
gatcttgaag ctctaaaagc aaatattcgc ttacagacag ccgattttag ttttgaaaaa 720
ggcaatttag ttgatccttt tgtttattct tttattagaa atccgcaaaa tcaaaaagaa 780
tgagctagtg atcttaatca agatcaaaaa actgtcagac tttatcttcg aaccgaattt 840
agtcctcagg ctaaaaccat tttaaaagac tataaataca aagatgagac tttcttaagt 900
agtatcgatt taaaagcaag taatggaact agtttatttg ctaatgaaaa tgatctaaaa 960
gatcaattag atgttgatct tttagatgtc tctgattatt ttggaggcca atcagagaca 1020
attactagta attcccaagt taaacctgtc cctgctagtg agagatcttt aaaagaccgg 1080
gttaaattta aaaaagatca gcaaaaacca agaattgaga aatttagttt atatgaatat 1140
gatgctctaa gtttttattc ccaacttcaa gaattagttt ctaaacctaa ttcaattaaa 1200
gatttagtta atgcaacttt agctcgtaat cttcggtttt cattaggaaa atataatttt 1260
ctttttgatg atttagccag tcatcttgat tatacttttt tagtttcaaa agcaaaaatt 1320
aaacaaagtt caattacaaa aaaattattc attgaattac caatcaaaat tagtcttaaa 1380
tcttcaattt taggtgatca agaacctaat attaaaactt tattcgaaaa agaagtgact 1440
tttaaattag ataacttccg tgatgttgaa atcgaaaaag cttttggact tttatatcca 1500
ggtgttaatg aagaacttga acaagcccga aaagctcaaa gagcaagctt tgaaaaagaa 1560

-continued

```
aaatcgaaaa aaggtcttaa agaatttagt caacaaaaag aagaaaattc aaagcgataa   1620
acaatcaaga gggtcttgaa gaagatgata atattactga aagacttcct gagaattccc   1680
cgattcaata tcagcaagaa aatgccggtt taggtgcaag tccggataaa ccttatatga   1740
taaaggatgt ccaaaatcaa cgttattatc tagcaaaatc acaaattcaa gaactaatta   1800
aggccaaaga ttataccaaa ttagccaaac ttttatccaa tagacatact tataatattt   1860
ctttaagatt aaaagaacaa ctttttgatg taaatccaag aattccgagc tctagagata   1920
tagaaaaggc aaaatttgtt cttgataaaa ccgaaaagaa taaatactgg cagatttatt   1980
caagtgcttc tcctgttttc caaaataaat gatcactttt tggatattac cgttatttat   2040
taggtcttga tccaaaacaa acaatccacg aattagtaaa attaggacaa aaagcgggtc   2100
ttcaatttga aggatatgaa aatcttcctt ctgatttcaa tcttgaggat cttaagaata   2160
ttaggattaa aacaccttta tttagtcaaa aagataattt caaattatct ttacttgatt   2220
ttaataatta ttatgacggt gaaattaaag ccccagaatt tggtcttcct ttatttttgc   2280
caaaagaatt aagaagaaat agttcaaatt ctggtggttc tcaaaactct aatagccctt   2340
gagaacaaga aattattagc caatttaaag atcaaaatct atctaatcag gatcagttag   2400
cccagtttag tactaaaatc tgggaaaaaa tcattggtga tgaaaacgaa tttgatcaaa   2460
ataacagact tcagtataaa cttttaaaag atcttcaaga atcttggatt aataaaaccc   2520
gcgataatct ttattggact tatctaggtg ataaacttaa agttaaacca aaaaataatt   2580
tagaggctaa atttagacaa atttccaatt tacaagagct tttaactgct ttttatactt   2640
cagctgctct ttctaataac tgaaattatt atcaagattc aggagcaaag tcaactatta   2700
tttttgaaga aatagctgag ctagatccaa aagtaaaaga aaaagttgga gctgatgttt   2760
atcaattaaa attccattat gcaatcggtt ttgatgataa tgctggtaag tttaatcaag   2820
aagtaattcg ttcttcaagt agaacaattt atcttaaaac ctcagggaaa tccaaattag   2880
aagcagatac aattgatcaa cttaatcaag cagttaaaaa tgcaccttta ggtcttcaaa   2940
gtttttatct tgatactgaa agatttgggg ttttccaaaa attagccact tccttagcag   3000
ttcaacataa acaaaaagaa aaaacactac ctaaaaaact aaataatgat ggctatactt   3060
taattcatga taaacttaaa aaaccagtaa ttccccaaat tagttcaagt ccagaaaaag   3120
actgatttga aggtaaatta aaccaaaacg ggcaaagcca aaatgtaaat gtctcaactt   3180
ttggctcaat aatcgagtcc ccttatttta gtactaattt ccaagaagat gctgacttag   3240
accaggatgg acaagatgat tcaagacaag gaaataatag tctagataat caagaagcag   3300
gtcttttaaa acaaaaactg gcaattttat taggtaatca atttatccaa tattatcaac   3360
aaaatgataa agaaattgaa ttcgagatta tcaatgttga gaaagtttca gagcttagtt   3420
tccgcgttga atttaaatta gcaaaaactc ttgaagacaa cggaaaaact attcgagttt   3480
tatcagatga gacaatgtca ttaattgtta atactacaat tgaaaaaaca ccagaaatga   3540
gtgcggttcc cgaagtattt gatactaaat gggttgagca atatgatcca agaaccccgc   3600
ttgcggcaaa gacaaagttt gtcttaaaat tcaaagatca aataccagtg gatggcagtg   3660
gaaatatttc tgataaatga ctagcaagta ttcctttggt gattcaccaa caaatgttgc   3720
gtcttagtcc tgtggttaaa acgataagag agctcggtct aaagaccgaa caacaacaac   3780
aacaacaaca acaacaacaa caacaacaac cccaaaagaa agctgttaga aaagaggaag   3840
aactagaaac ctataatcca aaagacgagt ttaatattct taatcctttg acaaaagctc   3900
accgccttac cttatcaaat ttggtaaata atgatccaaa ttataaaatt gaagatttaa   3960
```

-continued

```
aagtaatcaa aaatgaagct ggtgaccatc aattagcatt ttctctaaga gctaataata   4020

tcaaaagatt aatgaataca ccaattactt ttgctgatta taatcccttt ttctattata   4080

atgaagactg aagaagtata gataaatatt taaataataa aggaaatgtg agttctcacc   4140

aacaacaagc agccgggggt aatcaaggct cgggtctaat ccaaagactt aataaaaata   4200

ttaagcccga aacttttacc cccgcactca tagctcttaa acgagataat aatactaatc   4260

tttctaacta ttctgataaa ataataatga tcaaaccaaa atatttggtt gaacgatcaa   4320

ttggtgttcc ctgatcaacc ggccttgatg gttatattgg ttcagaacaa accaaggacg   4380

gaacttcctc aagcagtcaa caaaagggat ttaagcaaga ttttattcag gctttaggtc   4440

ttaaaaacac tgaatatcat ggtaaactag gtctttcaat tagaattttt gatcctggaa   4500

atgaactagc aaaaattaag gatgcttcaa ataaaaaagg ggaagaaaag ctgttaaaat   4560

catatgattt atttaaaaac tatttaaatg aatatgagaa aaaatcccct aaaattgcta   4620

agggatgaac aaatattcat cctgatcaaa aagaatatcc aaatccaaat caaaaactac   4680

ctgaaaatta tcttaaccta gttttaaatc aaccttgaaa ggttacttta tataattcaa   4740

gtgattttat tactaattta tttgttgaac ctgaaggctc agatcgtgga tcaggaacaa   4800

aattaaaaca agtaatccag aagcaagtta ataataacta tgctgactgg gggtctgcat   4860

atctcacgtt ctggtatgat aaaaatatca ttaccaatca gccaaatgtt ataactgcaa   4920

acattgctga tgtctttatt aaagatgtaa aagaacttga agataataca aaactaattg   4980

ctccaaatat tactcaatga tggccaaata ttagcggctc aaaagagaaa ttttataagc   5040

caacagtgtt ttttggtaat tgagaaaatg aaaacagcag tatgaattcc caggcgcaga   5100

cccctacctg ggagaagatc agagaaggat ttgctctcca agcgcttaaa tccagctttg   5160

atcaaaaaac aaggacattt gtccttacaa caaatgctcc tttaccttta tgaaaatacg   5220

gaccattagg tttccaaaat gggccgaatt tcaaaacaca agattgaagg cttgttttcc   5280

aaaatgatga taaccaaata gccgcgctaa gagtccagga gcaagatcgc ccagaaaaat   5340

caagcgaaga taaagacaag caaaaatgga ttaaatttaa agttgttatc cctgaagaaa   5400

tgtttaattc cggtaatata cgttttgttg gggtaatgca gatccaaggt cctaatactt   5460

tatgacttcc agtgattaat tcttcggtta tctatgactt ctatcgcgga acaggagatt   5520

ctaatgatgt cgccaatctt aatgtagctc cttgacaggt taaaacaatc gcatttacaa   5580

ataacgcctt taataatgtt ttcaaagagt ttaatatctc taaaaaaata gtagaa       5636
```

<210> SEQ ID NO 8
<211> LENGTH: 1879
<212> TYPE: PRT
<213> ORGANISM: Mycoplasma hyopneumoniae

<400> SEQUENCE: 8

```
Met Lys Asn Lys Lys Ser Thr Leu Leu Leu Ala Thr Ala Ala Ala Ile
 1               5                  10                  15

Ile Gly Ser Thr Val Phe Gly Thr Val Val Gly Leu Ala Ser Lys Val
            20                  25                  30

Lys Tyr Arg Gly Val Asn Pro Thr Gln Gly Val Ile Ser Gln Leu Gly
        35                  40                  45

Leu Ile Asp Ser Val Ala Phe Lys Pro Ser Ile Ala Asn Phe Thr Ser
    50                  55                  60

Asp Tyr Gln Ser Val Lys Lys Ala Leu Leu Asn Gly Lys Thr Phe Asp
65                  70                  75                  80
```

-continued

```
Pro Lys Ser Ser Glu Phe Thr Asp Phe Val Ser Lys Phe Asp Phe Leu
                85                  90                  95

Thr Asn Asn Gly Arg Thr Val Leu Glu Ile Pro Lys Lys Tyr Gln Val
            100                 105                 110

Val Ile Ser Glu Phe Ser Pro Glu Asp Asp Lys Glu Arg Phe Arg Leu
        115                 120                 125

Gly Phe His Leu Lys Glu Lys Leu Glu Asp Gly Asn Ile Ala Gln Ser
    130                 135                 140

Ala Thr Lys Phe Ile Tyr Leu Leu Pro Leu Asp Met Pro Lys Ala Ala
145                 150                 155                 160

Leu Gly Gln Tyr Ser Tyr Ile Val Asp Lys Asn Phe Asn Asn Leu Ile
                165                 170                 175

Ile His Pro Leu Ser Asn Phe Ser Ala Gln Ser Ile Lys Pro Leu Ala
            180                 185                 190

Leu Thr Arg Ser Ser Asp Phe Ile Ala Lys Leu Asn Gln Phe Asn Asn
        195                 200                 205

Gln Asp Glu Leu Trp Val Tyr Leu Glu Lys Phe Phe Asp Leu Glu Ala
    210                 215                 220

Leu Lys Ala Asn Ile Arg Leu Gln Thr Ala Asp Phe Ser Phe Glu Lys
225                 230                 235                 240

Gly Asn Leu Val Asp Pro Phe Val Tyr Ser Phe Ile Arg Asn Pro Gln
                245                 250                 255

Asn Gln Lys Glu Trp Ala Ser Asp Leu Asn Gln Asp Gln Lys Thr Val
            260                 265                 270

Arg Leu Tyr Leu Arg Thr Glu Phe Ser Pro Gln Ala Lys Thr Ile Leu
        275                 280                 285

Lys Asp Tyr Lys Tyr Lys Asp Glu Thr Phe Leu Ser Ser Ile Asp Leu
    290                 295                 300

Lys Ala Ser Asn Gly Thr Ser Leu Phe Ala Asn Glu Asn Asp Leu Lys
305                 310                 315                 320

Asp Gln Leu Asp Val Asp Leu Leu Asp Val Ser Asp Tyr Phe Gly Gly
                325                 330                 335

Gln Ser Glu Thr Ile Thr Ser Asn Ser Gln Val Lys Pro Val Pro Ala
            340                 345                 350

Ser Glu Arg Ser Leu Lys Asp Arg Val Lys Phe Lys Lys Asp Gln Gln
        355                 360                 365

Lys Pro Arg Ile Glu Lys Phe Ser Leu Tyr Glu Tyr Asp Ala Leu Ser
    370                 375                 380

Phe Tyr Ser Gln Leu Gln Glu Leu Val Ser Lys Pro Asn Ser Ile Lys
385                 390                 395                 400

Asp Leu Val Asn Ala Thr Leu Ala Arg Asn Leu Arg Phe Ser Leu Gly
                405                 410                 415

Lys Tyr Asn Phe Leu Phe Asp Asp Leu Ala Ser His Leu Asp Tyr Tyr
            420                 425                 430

Phe Leu Val Ser Lys Ala Lys Ile Lys Gln Ser Ser Ile Thr Lys Lys
        435                 440                 445

Leu Phe Ile Glu Leu Pro Ile Lys Ile Ser Leu Lys Ser Ser Ile Leu
    450                 455                 460

Gly Asp Gln Glu Pro Asn Ile Lys Thr Leu Phe Glu Lys Glu Val Thr
465                 470                 475                 480

Phe Lys Leu Asp Asn Phe Arg Asp Val Glu Ile Glu Lys Ala Phe Gly
                485                 490                 495
```

-continued

```
Leu Leu Tyr Pro Gly Val Asn Glu Glu Leu Glu Gln Ala Arg Lys Ala
            500                 505                 510

Gln Arg Ala Ser Phe Glu Lys Glu Lys Ser Lys Lys Gly Leu Lys Glu
        515                 520                 525

Phe Ser Gln Gln Lys Glu Glu Asn Ser Lys Ala Ile Asn Asn Gln Glu
    530                 535                 540

Gly Leu Glu Glu Asp Asp Asn Ile Thr Glu Arg Leu Pro Glu Asn Ser
545                 550                 555                 560

Pro Ile Gln Tyr Gln Gln Glu Asn Ala Gly Leu Gly Ala Ser Pro Asp
                565                 570                 575

Lys Pro Tyr Met Ile Lys Asp Val Gln Asn Gln Arg Tyr Tyr Leu Ala
            580                 585                 590

Lys Ser Gln Ile Gln Glu Leu Ile Lys Ala Lys Asp Tyr Thr Lys Leu
        595                 600                 605

Ala Lys Leu Leu Ser Asn Arg His Thr Tyr Asn Ile Ser Leu Arg Leu
    610                 615                 620

Lys Glu Gln Leu Phe Asp Val Asn Pro Arg Ile Pro Ser Ser Arg Asp
625                 630                 635                 640

Ile Glu Lys Ala Lys Phe Val Leu Asp Lys Thr Glu Lys Asn Lys Tyr
                645                 650                 655

Trp Gln Ile Tyr Ser Ser Ala Ser Pro Val Phe Gln Asn Lys Trp Ser
            660                 665                 670

Leu Phe Gly Tyr Tyr Arg Tyr Leu Leu Gly Leu Asp Pro Lys Gln Thr
        675                 680                 685

Ile His Glu Leu Val Lys Leu Gly Gln Lys Ala Gly Leu Gln Phe Glu
    690                 695                 700

Gly Tyr Glu Asn Leu Pro Ser Asp Phe Asn Leu Glu Asp Leu Lys Asn
705                 710                 715                 720

Ile Arg Ile Lys Thr Pro Leu Phe Ser Gln Lys Asp Asn Phe Lys Leu
                725                 730                 735

Ser Leu Leu Asp Phe Asn Asn Tyr Tyr Asp Gly Glu Ile Lys Ala Pro
            740                 745                 750

Glu Phe Gly Leu Pro Leu Phe Leu Pro Lys Glu Leu Arg Arg Asn Ser
        755                 760                 765

Ser Asn Ser Gly Gly Ser Gln Asn Ser Asn Ser Pro Trp Glu Gln Glu
    770                 775                 780

Ile Ile Ser Gln Phe Lys Asp Gln Asn Leu Ser Asn Gln Asp Gln Leu
785                 790                 795                 800

Ala Gln Phe Ser Thr Lys Ile Trp Glu Lys Ile Ile Gly Asp Glu Asn
                805                 810                 815

Glu Phe Asp Gln Asn Asn Arg Leu Gln Tyr Lys Leu Leu Lys Asp Leu
            820                 825                 830

Gln Glu Ser Trp Ile Asn Lys Thr Arg Asp Asn Leu Tyr Trp Thr Tyr
        835                 840                 845

Leu Gly Asp Lys Leu Lys Val Lys Pro Lys Asn Asn Leu Glu Ala Lys
    850                 855                 860

Phe Arg Gln Ile Ser Asn Leu Gln Glu Leu Leu Thr Ala Phe Tyr Thr
865                 870                 875                 880

Ser Ala Ala Leu Ser Asn Asn Trp Asn Tyr Tyr Gln Asp Ser Gly Ala
                885                 890                 895

Lys Ser Thr Ile Ile Phe Glu Glu Ile Ala Glu Leu Asp Pro Lys Val
            900                 905                 910

Lys Glu Lys Val Gly Ala Asp Val Tyr Gln Leu Lys Phe His Tyr Ala
```

-continued

```
        915                 920                 925

Ile Gly Phe Asp Asp Asn Ala Gly Lys Phe Asn Gln Glu Val Ile Arg
    930                 935                 940

Ser Ser Ser Arg Thr Ile Tyr Leu Lys Thr Ser Gly Lys Ser Lys Leu
945                 950                 955                 960

Glu Ala Asp Thr Ile Asp Gln Leu Asn Gln Ala Val Lys Asn Ala Pro
                965                 970                 975

Leu Gly Leu Gln Ser Phe Tyr Leu Asp Thr Glu Arg Phe Gly Val Phe
            980                 985                 990

Gln Lys Leu Ala Thr Ser Leu Ala Val Gln His Lys Gln Lys Glu Lys
        995                 1000                1005

Thr Leu Pro Lys Lys Leu Asn Asn Asp Gly Tyr Thr Leu Ile His Asp
    1010                1015                1020

Lys Leu Lys Lys Pro Val Ile Pro Gln Ile Ser Ser Ser Pro Glu Lys
1025                1030                1035                1040

Asp Trp Phe Glu Gly Lys Leu Asn Gln Asn Gly Gln Ser Gln Asn Val
                1045                1050                1055

Asn Val Ser Thr Phe Gly Ser Ile Ile Glu Ser Pro Tyr Phe Ser Thr
            1060                1065                1070

Asn Phe Gln Glu Asp Ala Asp Leu Asp Gln Asp Gly Gln Asp Asp Ser
        1075                1080                1085

Arg Gln Gly Asn Asn Ser Leu Asp Asn Gln Glu Ala Gly Leu Leu Lys
    1090                1095                1100

Gln Lys Leu Ala Ile Leu Leu Gly Asn Gln Phe Ile Gln Tyr Tyr Gln
1105                1110                1115                1120

Gln Asn Asp Lys Glu Ile Glu Phe Glu Ile Ile Asn Val Glu Lys Val
                1125                1130                1135

Ser Glu Leu Ser Phe Arg Val Glu Phe Lys Leu Ala Lys Thr Leu Glu
            1140                1145                1150

Asp Asn Gly Lys Thr Ile Arg Val Leu Ser Asp Glu Thr Met Ser Leu
        1155                1160                1165

Ile Val Asn Thr Thr Ile Glu Lys Thr Pro Glu Met Ser Ala Val Pro
    1170                1175                1180

Glu Val Phe Asp Thr Lys Trp Val Glu Gln Tyr Asp Pro Arg Thr Pro
1185                1190                1195                1200

Leu Ala Ala Lys Thr Lys Phe Val Leu Lys Phe Lys Asp Gln Ile Pro
                1205                1210                1215

Val Asp Gly Ser Gly Asn Ile Ser Asp Lys Trp Leu Ala Ser Ile Pro
            1220                1225                1230

Leu Val Ile His Gln Gln Met Leu Arg Leu Ser Pro Val Val Lys Thr
        1235                1240                1245

Ile Arg Glu Leu Gly Leu Lys Thr Glu Gln Gln Gln Gln Gln Gln Gln
    1250                1255                1260

Gln Gln Gln Gln Gln Gln Pro Gln Lys Lys Ala Val Arg Lys Glu Glu
1265                1270                1275                1280

Glu Leu Glu Thr Tyr Asn Pro Lys Asp Glu Phe Asn Ile Leu Asn Pro
                1285                1290                1295

Leu Thr Lys Ala His Arg Leu Thr Leu Ser Asn Leu Val Asn Asn Asp
            1300                1305                1310

Pro Asn Tyr Lys Ile Glu Asp Leu Lys Val Ile Lys Asn Glu Ala Gly
        1315                1320                1325

Asp His Gln Leu Ala Phe Ser Leu Arg Ala Asn Asn Ile Lys Arg Leu
    1330                1335                1340
```

-continued

```
Met Asn Thr Pro Ile Thr Phe Ala Asp Tyr Asn Pro Phe Phe Tyr Tyr
1345                1350                1355                1360

Asn Glu Asp Trp Arg Ser Ile Asp Lys Tyr Leu Asn Asn Lys Gly Asn
                1365                1370                1375

Val Ser Ser His Gln Gln Gln Ala Ala Gly Gly Asn Gln Gly Ser Gly
            1380                1385                1390

Leu Ile Gln Arg Leu Asn Lys Asn Ile Lys Pro Glu Thr Phe Thr Pro
        1395                1400                1405

Ala Leu Ile Ala Leu Lys Asp Arg Asn Asn Thr Asn Leu Ser Asn Tyr
    1410                1415                1420

Ser Asp Lys Ile Ile Met Ile Lys Pro Lys Tyr Leu Val Glu Arg Ser
1425                1430                1435                1440

Ile Gly Val Pro Trp Ser Thr Gly Leu Asp Gly Tyr Ile Gly Ser Glu
                1445                1450                1455

Gln Thr Lys Asp Gly Thr Ser Ser Ser Ser Gln Gln Lys Gly Phe Asp
            1460                1465                1470

Gln Asp Phe Ile Gln Ala Leu Gly Leu Lys Asn Thr Glu Tyr His Gly
        1475                1480                1485

Lys Leu Gly Leu Ser Ile Arg Ile Phe Asp Pro Gly Asn Glu Leu Ala
    1490                1495                1500

Lys Ile Lys Asp Ala Ser Asn Lys Lys Gly Glu Glu Lys Leu Leu Lys
1505                1510                1515                1520

Ser Tyr Asp Leu Phe Lys Asn Tyr Leu Asn Glu Tyr Glu Lys Lys Ser
                1525                1530                1535

Pro Lys Ile Ala Lys Gly Trp Thr Asn Ile His Pro Asp Gln Lys Glu
            1540                1545                1550

Tyr Pro Asn Pro Asn Gln Lys Leu Pro Glu Asn Tyr Leu Asn Leu Val
        1555                1560                1565

Leu Asn Gln Pro Trp Lys Val Thr Leu Tyr Asn Ser Ser Asp Phe Ile
    1570                1575                1580

Thr Asn Leu Phe Val Glu Pro Glu Gly Ser Asp Arg Gly Ser Gly Thr
1585                1590                1595                1600

Lys Leu Lys Gln Val Ile Gln Lys Gln Val Asn Asn Asn Tyr Ala Asp
                1605                1610                1615

Trp Gly Ser Ala Tyr Leu Thr Phe Trp Tyr Asp Lys Asn Ile Ile Thr
            1620                1625                1630

Asn Gln Pro Asn Val Ile Thr Ala Asn Ile Ala Asp Val Phe Ile Lys
        1635                1640                1645

Asp Val Lys Glu Leu Glu Asp Asn Thr Lys Leu Ile Ala Pro Asn Ile
    1650                1655                1660

Thr Gln Trp Trp Pro Asn Ile Ser Gly Ser Lys Glu Lys Phe Tyr Lys
1665                1670                1675                1680

Pro Thr Val Phe Phe Gly Asn Trp Glu Asn Glu Asn Ser Ser Met Asn
                1685                1690                1695

Ser Gln Ala Gln Thr Pro Thr Trp Glu Lys Ile Arg Glu Gly Phe Ala
            1700                1705                1710

Leu Gln Ala Leu Lys Ser Ser Phe Asp Gln Lys Thr Arg Thr Phe Val
        1715                1720                1725

Leu Thr Thr Asn Ala Pro Leu Pro Leu Trp Lys Tyr Gly Pro Leu Gly
    1730                1735                1740

Phe Gln Asn Gly Pro Asn Phe Lys Thr Gln Asp Trp Arg Leu Val Phe
1745                1750                1755                1760
```

-continued

```
Gln Asn Asp Asp Asn Gln Ile Ala Ala Leu Arg Val Gln Glu Gln Asp
                1765                1770                1775

Arg Pro Glu Lys Ser Ser Glu Asp Lys Asp Lys Gln Lys Trp Ile Lys
            1780                1785                1790

Phe Lys Val Val Ile Pro Glu Glu Met Phe Asn Ser Gly Asn Ile Arg
        1795                1800                1805

Phe Val Gly Val Met Gln Ile Gln Gly Pro Asn Thr Leu Trp Leu Pro
    1810                1815                1820

Val Ile Asn Ser Ser Val Ile Tyr Asp Phe Tyr Arg Gly Thr Gly Asp
1825                1830                1835                1840

Ser Asn Asp Val Ala Asn Leu Asn Val Ala Pro Trp Gln Val Lys Thr
                1845                1850                1855

Ile Ala Phe Thr Asn Asn Ala Phe Asn Asn Val Phe Lys Glu Phe Asn
            1860                1865                1870

Ile Ser Lys Lys Ile Val Glu
        1875


<210> SEQ ID NO 9
<211> LENGTH: 3003
<212> TYPE: DNA
<213> ORGANISM: Mycoplasma hyopneumoniae

<400> SEQUENCE: 9

ttgattttaa ttgaagaaat taaggaaatc aaaaaattta tggaaaacac caacttgcac     60

tacaaaaaaa aaaaaaaaaa aagcactaac ctttctagaa aaaatctttt aacaattggg    120

gccgcagttt ttttcggaat tgcaataatc acaattccgc ttgtcaccgt tgctaattga    180

aagatcaaag atccacgact tcaagtacaa aatcaagcaa aattaattac aaatattcaa    240

ctaaaagatg agtatcaaaa tggaaattta agctattttg atcttaaaaa acagcttttt    300

aatgctgata atactaaaaa aactgggatt gactatagcc agttttttga tttttaccaa    360

aaaaataaca cgagcctacc aattaatttt gccactgatt atggctgaaa tcgttacaaa    420

cttgatgttt ttgatctaaa accacttgat caagaacaat cttttgaaat ttattatcgt    480

ttagtatatc aactacctga tgataaaaag gcaatttctg atcttttaac ccaaaaagtt    540

atctgaaatt atctccctga ttattcactt gctaatttcg ctaatttttc aagttcaaaa    600

ttggaaaaac taagagctta taccaacaag gaatttagtt tatcaaccaa aaaagaactt    660

acaaaattag taaaattaga agactttgaa aagcaagtaa actgggcaat aaataataat    720

gaagcccgca aaattattaa taaatatttt aatttagaag aaattattgc cgagattctt    780

aataataaag aattttctta tctagatgaa agtggaatat gaaatccgca atatcagatt    840

gaacttgtaa gagatcaaat tttaggtcag gattttttag caaaaacagg tcaaaaagga    900

atttataaat taacatttta tgctgctttt tcgccgaatt ttgctaaaaa aattgcggct    960

gatctcaata aaagttcaaa gtttcatttt ggaattaaca ttgatcttaa taatcttttc   1020

cttgataaaa cagtcgctga aaatattaaa ataactgaat tttctgaaga tgattattac   1080

ccacaaataa attttgaaaa aaatttagaa gccgaaatta atggttgaga ttttctaaat   1140

tattacaata accaaatttt tgcaactcaa aacgagagag aagattttct caagaacctt   1200

atagcaaaaa ttgttagaac tccgcttctg aaaaaagttg aatttgaaaa taaattatcc   1260

ggtattgatt atgcaaaatt tttaaaatat ttaaaattag atattaaatt agatgctaat   1320

tcaactaaat tggcttttaa aaataaccaa attgttgcca aaattttcgg aaaaaattatt   1380

cttagaaatg ctgaaaatca aattgtcgct gaaaaaaact tttcccaaac tattgaacat   1440
```

-continued

```
ctaaaccgtc tcgggcaaaa tgatgctgaa ttagtaaagc aaattaaaca gacaaaattt   1500

gaatttaaac cagaaactag aaaaaaaatt gcaaaccaaa agggtgcgcc aaaatcagaa   1560

attcttgcac tcttaaatgc caataaattt gataaattaa aaaatatcct tgaaaatggt   1620

gattattatg gctatgaatt taacgaagat cgcttaaaat tattagttca taattcacaa   1680

ttacctaatg ttgaagaatt tgcaaaatta agtgtagttc ctgagaaaat gtctgaggga   1740

attattaatc tttggaataa gtcatttaaa acaaatcaag aggttagtac atttttatct   1800

ttacttgcaa aaagggatat cagttttgtt gcaaaatatt gatatgatct tttaaataaa   1860

tttaaattaa ttgatccaaa aacacaatgg cctgaaaatc ttgaccaaaa tagtttattt   1920

aaacatttaa gtcaaataaa aattcagcct cctgagaaaa aagcagtttc actgacctcc   1980

gatttttgac ttttttcatt aaataatgac tacctaattt cccctgatta tcttaataat   2040

agtttttacc ttcactcaaa tttaaaaaat actttggact taatcaaaac tgaaagcgca   2100

tttaacacga gagattttgt cgaacatata agagaacttg caaaatcaat taaaccaaaa   2160

gattttatcc aagaaaaagg taaaaatcca attacaaatc ttagtgaatt tctagttgct   2220

ttttattcgc ttatttattc aaaggatcaa ggacttcttg ctgaatcact cgggcaaaat   2280

ttagactata aaattcagtt tgaactcgaa cctataagcc taaatgtagc agttagtcag   2340

gaaaaaacta atccaaataa taatttaaga ttaaataata atttaagatt aaaatattga   2400

tataaaattg gttcagttga tcaaaatggg aatttaattc aagtgattta ccaaacaaaa   2460

aaagaaactt tggatcttgt agttaatgaa aataataaat tgcttagtga agatgtagaa   2520

aaattaaatg aaattgctac taattttcca agtgcagacc aaattatttt ccttaaaaaa   2580

gaagattata cccaacttgt tgatagtata aaacaagtaa ttaaaacgga aaatactcca   2640

gttaaaattg ataatcagat caaaaatcta cctttttagtc aattttttga aaataattac   2700

ccagattatg gtttttatat aataaaaaca agtaaaaatt tagaaagtag taaacctgaa   2760

gcagcaaaag ttgctgcaaa accttcagca gccaagccag tagcagctaa accagaacaa   2820

caagaaattc atcaaagcga agaaattccc ggagttctta ctaatacaat atctcaactt   2880

ggcaatcaga tacgacataa ttttgattta tatgtataca aaaaagatca gccacagatt   2940

cactcaagta agccagttag ggtaattatt attgaaagtt cagaatcact atttgcttta   3000

aaa                                                                  3003
```

<210> SEQ ID NO 10
<211> LENGTH: 1001
<212> TYPE: PRT
<213> ORGANISM: Mycoplasma hyopneumoniae

<400> SEQUENCE: 10

```
Met Ile Leu Ile Glu Glu Ile Lys Glu Ile Lys Lys Phe Met Glu Asn
 1               5                  10                  15

Thr Asn Leu His Tyr Lys Lys Lys Lys Lys Lys Ser Thr Asn Leu Ser
            20                  25                  30

Arg Lys Asn Leu Leu Thr Ile Gly Ala Ala Val Phe Phe Gly Ile Ala
        35                  40                  45

Ile Ile Thr Ile Pro Leu Val Thr Val Ala Asn Trp Lys Ile Lys Asp
    50                  55                  60

Pro Arg Leu Gln Val Gln Asn Gln Ala Lys Leu Ile Thr Asn Ile Gln
65                  70                  75                  80

Leu Lys Asp Glu Tyr Gln Asn Gly Asn Leu Ser Tyr Phe Asp Leu Lys
```

-continued

```
                85                  90                  95

Lys Gln Leu Phe Asn Ala Asp Asn Thr Lys Lys Thr Gly Ile Asp Tyr
            100                 105                 110

Ser Gln Phe Phe Asp Phe Tyr Gln Lys Asn Asn Thr Ser Leu Pro Ile
        115                 120                 125

Asn Phe Ala Thr Asp Tyr Gly Trp Asn Arg Tyr Lys Leu Asp Val Phe
    130                 135                 140

Asp Leu Lys Pro Leu Asp Gln Glu Gln Ser Phe Glu Ile Tyr Tyr Arg
145                 150                 155                 160

Leu Val Tyr Gln Leu Pro Asp Asp Lys Lys Ala Ile Ser Asp Leu Leu
                165                 170                 175

Thr Gln Lys Val Ile Trp Asn Tyr Leu Pro Asp Tyr Ser Leu Ala Asn
            180                 185                 190

Phe Ala Asn Phe Ser Ser Ser Lys Leu Glu Lys Leu Arg Ala Tyr Thr
        195                 200                 205

Asn Lys Glu Phe Ser Leu Ser Thr Lys Lys Glu Leu Thr Lys Leu Val
    210                 215                 220

Lys Leu Glu Asp Phe Glu Lys Gln Val Asn Trp Ala Ile Asn Asn Asn
225                 230                 235                 240

Glu Ala Arg Lys Ile Ile Asn Lys Tyr Phe Asn Leu Glu Glu Ile Ile
                245                 250                 255

Ala Glu Ile Leu Asn Asn Lys Glu Phe Ser Tyr Leu Asp Glu Ser Gly
            260                 265                 270

Ile Trp Asn Pro Gln Tyr Gln Ile Glu Leu Val Arg Asp Gln Ile Leu
        275                 280                 285

Gly Gln Asp Phe Leu Ala Lys Thr Gly Gln Lys Gly Ile Tyr Lys Leu
    290                 295                 300

Thr Phe Tyr Ala Ala Phe Ser Pro Asn Phe Ala Lys Lys Ile Ala Ala
305                 310                 315                 320

Asp Leu Asn Lys Ser Ser Lys Phe His Phe Gly Ile Asn Ile Asp Leu
                325                 330                 335

Asn Asn Leu Phe Leu Asp Lys Thr Val Ala Glu Asn Ile Lys Ile Thr
            340                 345                 350

Glu Phe Ser Glu Asp Asp Tyr Tyr Pro Gln Ile Asn Phe Glu Lys Asn
        355                 360                 365

Leu Glu Ala Glu Ile Asn Gly Trp Asp Phe Leu Asn Tyr Tyr Asn Asn
    370                 375                 380

Gln Ile Phe Ala Thr Gln Asn Glu Arg Glu Asp Phe Leu Lys Asn Leu
385                 390                 395                 400

Ile Ala Lys Ile Val Arg Thr Pro Leu Leu Lys Lys Val Glu Phe Glu
                405                 410                 415

Asn Lys Leu Ser Gly Ile Asp Tyr Ala Lys Phe Leu Lys Tyr Leu Lys
            420                 425                 430

Leu Asp Ile Lys Leu Asp Ala Asn Ser Thr Lys Leu Ala Phe Lys Asn
        435                 440                 445

Asn Gln Ile Val Ala Lys Ile Phe Gly Lys Ile Ile Leu Arg Asn Ala
    450                 455                 460

Glu Asn Gln Ile Val Ala Glu Lys Asn Phe Ser Gln Thr Ile Glu His
465                 470                 475                 480

Leu Asn Arg Leu Gly Gln Asn Asp Ala Glu Leu Val Lys Gln Ile Lys
                485                 490                 495

Gln Thr Lys Phe Glu Phe Lys Pro Glu Thr Arg Lys Lys Ile Ala Asn
            500                 505                 510
```

-continued

```
Gln Lys Gly Ala Pro Lys Ser Glu Ile Leu Ala Leu Leu Asn Ala Asn
        515                 520                 525

Lys Phe Asp Lys Leu Lys Asn Ile Leu Glu Asn Gly Asp Tyr Tyr Gly
    530                 535                 540

Tyr Glu Phe Asn Glu Asp Arg Leu Lys Leu Leu Val His Asn Ser Gln
545                 550                 555                 560

Leu Pro Asn Val Glu Glu Phe Ala Lys Leu Ser Val Val Pro Glu Lys
                565                 570                 575

Met Ser Glu Gly Ile Ile Asn Leu Trp Asn Lys Ser Phe Lys Thr Asn
            580                 585                 590

Gln Glu Val Ser Thr Phe Leu Ser Leu Leu Ala Lys Arg Asp Ile Ser
        595                 600                 605

Phe Val Ala Lys Tyr Trp Tyr Asp Leu Leu Asn Lys Phe Lys Leu Ile
    610                 615                 620

Asp Pro Lys Thr Gln Trp Pro Glu Asn Leu Asp Gln Asn Ser Leu Phe
625                 630                 635                 640

Lys His Leu Ser Gln Ile Lys Ile Gln Pro Pro Glu Lys Lys Ala Val
                645                 650                 655

Ser Leu Thr Ser Asp Phe Trp Leu Phe Ser Leu Asn Asn Asp Tyr Leu
            660                 665                 670

Ile Ser Pro Asp Tyr Leu Asn Asn Ser Phe Tyr Leu His Ser Asn Leu
        675                 680                 685

Lys Asn Thr Leu Asp Leu Ile Lys Thr Glu Ser Ala Phe Asn Thr Arg
    690                 695                 700

Asp Phe Val Glu His Ile Arg Glu Leu Ala Lys Ser Ile Lys Pro Lys
705                 710                 715                 720

Asp Phe Ile Gln Glu Lys Gly Lys Asn Pro Ile Thr Asn Leu Ser Glu
                725                 730                 735

Phe Leu Val Ala Phe Tyr Ser Leu Ile Tyr Ser Lys Asp Gln Gly Leu
            740                 745                 750

Leu Ala Glu Ser Leu Gly Gln Asn Leu Asp Tyr Lys Ile Gln Phe Glu
        755                 760                 765

Leu Glu Pro Ile Ser Leu Asn Val Ala Val Ser Gln Glu Lys Thr Asn
    770                 775                 780

Pro Asn Asn Asn Leu Arg Leu Asn Asn Asn Leu Arg Leu Lys Tyr Trp
785                 790                 795                 800

Tyr Lys Ile Gly Ser Val Asp Gln Asn Gly Asn Leu Ile Gln Val Ile
                805                 810                 815

Tyr Gln Thr Lys Lys Glu Thr Leu Asp Leu Val Val Asn Glu Asn Asn
            820                 825                 830

Lys Leu Leu Ser Glu Asp Val Glu Lys Leu Asn Glu Ile Ala Thr Asn
        835                 840                 845

Phe Pro Ser Ala Asp Gln Ile Ile Phe Leu Lys Lys Glu Asp Tyr Thr
    850                 855                 860

Gln Leu Val Asp Ser Ile Lys Gln Val Ile Lys Thr Glu Asn Thr Pro
865                 870                 875                 880

Val Lys Ile Asp Asn Gln Ile Lys Asn Leu Pro Phe Ser Gln Phe Phe
                885                 890                 895

Glu Asn Asn Tyr Pro Asp Tyr Gly Phe Tyr Ile Ile Lys Thr Ser Lys
            900                 905                 910

Asn Leu Glu Ser Ser Lys Pro Glu Ala Ala Lys Val Ala Ala Lys Pro
        915                 920                 925
```

-continued

```
Ser Ala Ala Lys Pro Val Ala Ala Lys Pro Glu Gln Gln Glu Ile His
    930                 935                 940

Gln Ser Glu Glu Ile Pro Gly Val Leu Thr Asn Thr Ile Ser Gln Leu
945                 950                 955                 960

Gly Asn Gln Ile Arg His Asn Phe Asp Leu Tyr Val Tyr Lys Lys Asp
                965                 970                 975

Gln Pro Gln Ile His Ser Ser Lys Pro Val Arg Val Ile Ile Ile Glu
            980                 985                 990

Ser Ser Glu Ser Leu Phe Ala Leu Lys
        995                 1000
```

<210> SEQ ID NO 11
<211> LENGTH: 2871
<212> TYPE: DNA
<213> ORGANISM: Mycoplasma hyopneumoniae

<400> SEQUENCE: 11

```
atgaaaaaaa acaagctaaa atatttaatt ttctcaatta ttggaattag tacaattata     60

agtcttgctg ttacaattcc ttatgcactt tcatcccaag ccgaaaaata taatctagaa    120

ctaaattctt ataacattga tcttggaaaa gcacaaaatt tgaactcaag aactaatttt    180

aatagtgctg aatttgataa attagttgca aatttaaagg taaaacctaa atttgccaag    240

cgactaaacg cttttgatgc tctaaatttt cactttgata aatcttatag tttcgatcta    300

gctgatgcag ttgatttaag tagtctaagt caaaaatatc ctgatctaag ttttaaattg    360

gttatccctg ataataaatc caggtttgaa atcaaagaaa ataagctaaa aaatatcgga    420

cttaatgtaa ctaacacttc aaaaaccata aattatacag caaaattcga ccttgatttc    480

tcaggtcaag aaaagtcttt ccaatttcta cccgaaaatt tcactggcca aattagtctt    540

agaaatcttg aatcacttaa aggaaaaacc gcaactgaaa tagcaatttt attttataat    600

gcttgactaa aacggtttaa taaactttct gattcaaaaa ttgccttata tgaaactttt    660

ggcgaatttg gtggggcttc ctttagccta aattctgaac caatttttat ccttccagaa    720

aattttgaaa tcaaaccgga tctaaaagat aataaactag tttttgcaag tataaatgat    780

gaaaaaaatg agcttgttct taatatggtt ttatatgata aaacagctaa aactgagaaa    840

atttttcccc ttagatttgt tgatctccca aaaacaaatc agaaatatgg ggaaaaattt    900

ttagcaagtt ttttgaaaaa ctatgaattt aatagtgaaa tttcaaaata tctagccaaa    960

aataacttag atattgcaca attattttca ttaccttctg atccaaaaag tcttgattta   1020

actaaatttg agtcctgatt tattcaaaaa tcagtgccaa atacaacttt ttttgctgat   1080

attaaaggtt taattcctaa ttttgagacc aaaaaagcag ctttttttagt taaaaaacct   1140

gaaaaagttg gtcagaataa gaatttatta actattaatt taaaattaga aggaactttt   1200

ttagtaaatg atcaagttcc tgcaggtcta aatttgactc aggataaaca ctatacttat   1260

aatttcgact ttgactacga tgcaacacaa gaaatttatt ctggatattt tcgaaatgcg   1320

cttgaattat ttgatgctag aacggcaaaa aatcttgata atttaaaact tgaggtcaaa   1380

aacgatcttc cagtaacggt tttcgcctca acaattaata caaaaattgc ccatctttta   1440

aataaacccc ttgaacttaa gggaattact aaaaaaatga gtcctttatt tgattttctt   1500

aatttttcaa caagtaaaaa tgaaaaatta gaaacaaaaa tggctccacc aaatgctaag   1560

atgcaaaatg ttggtgcaat tttatttaat gaagaggtaa aacaacaaga aagtcaggta   1620

aaggatcagg caaaacaaga aaaatcaagt aaagattccc aaagtaaaca aactgatcaa   1680
```

-continued

```
agtgaaaaag aaccaaaagt tgaaactaaa acaatccagg cagaaaatgg aggaacttat   1740

ttatctaaac tttttgaaaa tttagaaaaa actagtttcc caacaaacac tctattatat   1800

ttatcaactt tttatcggga taaatttatt ttaaaattag aactaaaagc tgaaggaata   1860

acaaaagaaa cacttgagat taaaattgac aaagttgctc ctgataataa agcttatcaa   1920

gcattagtcc aaagtacaaa tacggattta ttccttgatt gacgatcaaa tataaccaca   1980

acaacagaaa aataccaaaa taaaccagta attgcatcga ttagcgcact aaataatccg   2040

aatttaaaat ttaaggtaaa tccagaacct tcaaataaat cgcagcaaaa agtacatcta   2100

gatcaagccg gtatttattt agccgaaggg ggaataagtc ttgaaaactt aagtcaagaa   2160

caagcaaaaa atcttaaact tgatgaaggc aagacaattt tttatgcctt taaacccact   2220

aaattatcac gaagatcact tttaagatat tttctattaa gcgcaagtga taattctagt   2280

tcaaaattca gtttattaat cgaaccagaa atattactaa ccgggtttaa taaaattggt   2340

gctgattttg aaaaggtaga gcaaaataat aaaaatcaat taaaatggac cgatgcctca   2400

ggtgggctgc aaaaaacttt taacgggact tatcaagata tttattattt cctttacaa    2460

cttctccaac ataataaagt tgcgctttat cctaaaaatc aatcagataa atcacatgat   2520

ttcctcaacg ctccggctgc tacaatggtt ctagtggcaa cagttgaaag cgaaaataca   2580

gaaaaatacc ttaaaatgaa gctttttca agtgattatc aaaatgggaa aaaggaaatt    2640

tttacctgaa aaaccaaaat tgagagccaa tttcaaaatc tcgatctagc taaaaatcta   2700

actttaggta caacaaaaag caataatcaa gaaaatattg acaaagaaca acaagatgat   2760

agtagaaaac cgaccggaat aacactaaaa ggttttgccc tctttgataa accaaaagat   2820

aatcaaaaat ataataatat ccttgaaaaa ttccttagcg aatatatgga a            2871
```

<210> SEQ ID NO 12
<211> LENGTH: 957
<212> TYPE: PRT
<213> ORGANISM: Mycoplasma hyopneumoniae

<400> SEQUENCE: 12

```
Met Lys Lys Asn Lys Leu Lys Tyr Leu Ile Phe Ser Ile Ile Gly Ile
 1               5                  10                  15

Ser Thr Ile Ile Ser Leu Ala Val Thr Ile Pro Tyr Ala Leu Ser Ser
            20                  25                  30

Gln Ala Glu Lys Tyr Asn Leu Glu Leu Asn Ser Tyr Asn Ile Asp Leu
        35                  40                  45

Gly Lys Ala Gln Asn Leu Asn Ser Arg Thr Asn Phe Asn Ser Ala Glu
    50                  55                  60

Phe Asp Lys Leu Val Ala Asn Leu Lys Val Lys Pro Lys Phe Ala Lys
65                  70                  75                  80

Arg Leu Asn Ala Phe Asp Ala Leu Asn Phe His Phe Asp Lys Ser Tyr
                85                  90                  95

Ser Phe Asp Leu Ala Asp Ala Val Asp Leu Ser Ser Leu Ser Gln Lys
            100                 105                 110

Tyr Pro Asp Leu Ser Phe Lys Leu Val Ile Pro Asp Asn Lys Ser Arg
        115                 120                 125

Phe Glu Ile Lys Glu Asn Lys Leu Lys Asn Ile Gly Leu Asn Val Thr
    130                 135                 140

Asn Thr Ser Lys Thr Ile Asn Tyr Thr Ala Lys Phe Asp Leu Asp Phe
145                 150                 155                 160

Ser Gly Gln Glu Lys Ser Phe Gln Phe Leu Pro Glu Asn Phe Thr Gly
```

-continued

```
                165                 170                 175

Gln Ile Ser Leu Arg Asn Leu Glu Ser Leu Lys Gly Lys Thr Ala Thr
            180                 185                 190

Glu Ile Ala Ile Leu Phe Tyr Asn Ala Trp Leu Lys Arg Phe Asn Lys
        195                 200                 205

Leu Ser Asp Ser Lys Ile Ala Leu Tyr Glu Thr Phe Gly Glu Phe Gly
    210                 215                 220

Gly Ala Ser Phe Ser Leu Asn Ser Glu Pro Ile Phe Ile Leu Pro Glu
225                 230                 235                 240

Asn Phe Glu Ile Lys Pro Asp Leu Lys Asp Asn Lys Leu Val Phe Ala
                245                 250                 255

Ser Ile Asn Asp Glu Lys Asn Glu Leu Val Leu Asn Met Val Leu Tyr
            260                 265                 270

Asp Lys Thr Ala Lys Thr Glu Lys Ile Phe Pro Leu Arg Phe Val Asp
        275                 280                 285

Leu Pro Lys Thr Asn Gln Lys Tyr Gly Glu Lys Phe Leu Ala Ser Phe
    290                 295                 300

Leu Lys Asn Tyr Glu Phe Asn Ser Glu Ile Ser Lys Tyr Leu Ala Lys
305                 310                 315                 320

Asn Asn Leu Asp Ile Ala Gln Leu Phe Ser Leu Pro Ser Asp Pro Lys
                325                 330                 335

Ser Leu Asp Leu Thr Lys Phe Glu Ser Trp Phe Ile Gln Lys Ser Val
            340                 345                 350

Pro Asn Thr Thr Phe Phe Ala Asp Ile Lys Gly Leu Ile Pro Asn Phe
        355                 360                 365

Glu Thr Lys Lys Ala Ala Phe Leu Val Lys Lys Pro Glu Lys Val Gly
    370                 375                 380

Gln Asn Lys Asn Leu Leu Thr Ile Asn Leu Lys Leu Glu Gly Thr Phe
385                 390                 395                 400

Leu Val Asn Asp Gln Val Pro Ala Gly Leu Asn Leu Thr Gln Asp Lys
                405                 410                 415

His Tyr Thr Tyr Asn Phe Asp Phe Asp Tyr Asp Ala Thr Gln Glu Ile
            420                 425                 430

Tyr Ser Gly Tyr Phe Arg Asn Ala Leu Glu Leu Phe Asp Ala Arg Thr
        435                 440                 445

Ala Lys Asn Leu Asp Asn Leu Lys Leu Glu Val Lys Asn Asp Leu Pro
    450                 455                 460

Val Thr Val Phe Ala Ser Thr Ile Asn Thr Lys Ile Ala His Leu Leu
465                 470                 475                 480

Asn Lys Pro Leu Glu Leu Lys Gly Ile Thr Lys Lys Met Ser Pro Leu
                485                 490                 495

Phe Asp Phe Leu Asn Phe Ser Thr Ser Lys Asn Glu Lys Leu Glu Thr
            500                 505                 510

Lys Met Ala Pro Pro Asn Ala Lys Met Gln Asn Val Gly Ala Ile Leu
        515                 520                 525

Phe Asn Glu Glu Val Lys Gln Gln Glu Ser Gln Val Lys Asp Gln Ala
    530                 535                 540

Lys Gln Glu Lys Ser Ser Lys Asp Ser Gln Ser Lys Gln Thr Asp Gln
545                 550                 555                 560

Ser Glu Lys Glu Pro Lys Val Glu Thr Lys Thr Ile Gln Ala Glu Asn
                565                 570                 575

Gly Gly Thr Tyr Leu Ser Lys Leu Phe Glu Asn Leu Glu Lys Thr Ser
            580                 585                 590
```

-continued

```
Phe Pro Thr Asn Thr Leu Leu Tyr Leu Ser Thr Phe Tyr Arg Asp Lys
        595                 600                 605

Phe Ile Leu Lys Leu Glu Leu Lys Ala Glu Gly Ile Thr Lys Glu Thr
    610                 615                 620

Leu Glu Ile Lys Ile Asp Lys Val Ala Pro Asp Asn Lys Ala Tyr Gln
625                 630                 635                 640

Ala Leu Val Gln Ser Thr Asn Thr Asp Leu Phe Leu Asp Trp Arg Ser
                645                 650                 655

Asn Ile Thr Thr Thr Thr Glu Lys Tyr Gln Asn Lys Pro Val Ile Ala
            660                 665                 670

Ser Ile Ser Ala Leu Asn Asn Pro Asn Leu Lys Phe Lys Val Asn Pro
        675                 680                 685

Glu Pro Ser Asn Lys Ser Gln Gln Lys Val His Leu Asp Gln Ala Gly
    690                 695                 700

Ile Tyr Leu Ala Glu Gly Gly Ile Ser Leu Glu Asn Leu Ser Gln Glu
705                 710                 715                 720

Gln Ala Lys Asn Leu Lys Leu Asp Glu Gly Lys Thr Ile Phe Tyr Ala
                725                 730                 735

Phe Lys Pro Thr Lys Leu Ser Arg Arg Ser Leu Leu Arg Tyr Phe Leu
            740                 745                 750

Leu Ser Ala Ser Asp Asn Ser Ser Ser Lys Phe Ser Leu Leu Ile Glu
        755                 760                 765

Pro Glu Ile Leu Leu Thr Gly Phe Asn Lys Ile Gly Ala Asp Phe Glu
    770                 775                 780

Lys Val Glu Gln Asn Asn Lys Asn Gln Leu Lys Trp Thr Asp Ala Ser
785                 790                 795                 800

Gly Gly Leu Gln Lys Thr Phe Asn Gly Thr Tyr Gln Asp Ile Tyr Tyr
                805                 810                 815

Phe Leu Leu Gln Leu Leu Gln His Asn Lys Val Ala Leu Tyr Pro Lys
            820                 825                 830

Asn Gln Ser Asp Lys Ser His Asp Phe Leu Asn Ala Pro Ala Ala Thr
        835                 840                 845

Met Val Leu Val Ala Thr Val Glu Ser Glu Asn Thr Glu Lys Tyr Leu
    850                 855                 860

Lys Met Lys Leu Phe Ser Ser Asp Tyr Gln Asn Gly Lys Lys Glu Ile
865                 870                 875                 880

Phe Thr Trp Lys Thr Lys Ile Glu Ser Gln Phe Gln Asn Leu Asp Leu
                885                 890                 895

Ala Lys Asn Leu Thr Leu Gly Thr Thr Lys Ser Asn Asn Gln Glu Asn
            900                 905                 910

Ile Asp Lys Glu Gln Gln Asp Asp Ser Arg Lys Pro Thr Gly Ile Thr
        915                 920                 925

Leu Lys Gly Phe Ala Leu Phe Asp Lys Pro Lys Asp Asn Gln Lys Tyr
    930                 935                 940

Asn Asn Ile Leu Glu Lys Phe Leu Ser Glu Tyr Met Glu
945                 950                 955
```

<210> SEQ ID NO 13
<211> LENGTH: 2835
<212> TYPE: DNA
<213> ORGANISM: Mycoplasma hyopneumoniae

<400> SEQUENCE: 13

```
atgaagttag caaaattact taaaaaacct ttttgattaa taacaacaat tgccggaatt      60
```

-continued

```
agtcttagtt tatcagccgc tgttggtata gttgtcggaa ttaattctta taataaatca    120
tattattctt atctaaatga aaatccaagt cagctaaaaa ctactaaaac aacaaaaata    180
tcccagcaag attttgataa aatagtctca aatttaaaaa ttagggataa ttttaagaaa    240
atatcagcaa aaacagcttt atcagcggta aaaaatgatt tataccggta tgacttagtt    300
cgggcttttg aattttcaag tttagaaact aacaactatc aaattagttt tgatttagaa    360
aatgcagtag ttgatcaaaa ttcaattaaa aatgtgctag tttttgcaaa atctgaaaaa    420
gatcaagtaa catattcaaa acaaattgaa cttaaagggt ttgctcaaga tgatgaagct    480
gcaggcgatc ttgttaaatt ccaaattgat caaagaaaat cctttgttaa tctttataaa    540
tttgattatt ctttttctga atttcaaaga attcttagcg aaaattatcg acaaattaga    600
aatacaaatt cttttacaag gttggcaaat gctttgattt cctcaaaagc gagtctttca    660
ctttataatt ccttagggca accagtattt ttagatgaaa attatcgctt agaaccagtt    720
ttgaattcaa aaaaagaatt aaatttacta gaaaaaaata agaaattgta tttagaactt    780
aatttagttg aaaaagagag ccaaaagaaa attaatttaa cactagaaat ccgtccatta    840
ttaacaaatc aagaatttac tagtgagtta aaaactttat ttgaatcaaa tttagaccaa    900
aatcttagcc taaatcttga actaaaaaat gctcttttcc atgatagaac cagtttttct    960
gagtatttat atggaagtcc acagcaaaga actaaaactg atgaagtaaa acagaaagct   1020
aaggaattaa aggatctttt tggttttaga tcagcaaaat tctgacagga tacaaaattt   1080
ggaacttttt atgtaataat taagccccaa cttttagatc ctgcaaaaat tagtcaagaa   1140
gataagaaaa aacttttagc tgataaaaaa atccgttttg aagttctaac taccttaaaa   1200
agaaaagcgc ttgatcaaca agatgttctc actgatcttc cagttttagt cgatctaagc   1260
cttgattcta ataaatacga aacagccata agtcaaattt ttaattcaac aaagacaacc   1320
aaagaattta aaatgcaaga atatgaagat agagcgaagt tatcaaccaa agaaatcaaa   1380
gaaacaattg ataaattagc aaatcttgcc gcaaaagtta gtaatttatc cgaaccaagt   1440
gatgaagttg ttcgtgctgt ctatttatta aatacaggga aatatctttt tgatgatgag   1500
atccagcaag aaaaaactaa tcttaaaaaa ataatagaac aagcccgaat gaaagctgac   1560
accaagaatt tggctccaaa agtacctagt cctattcaaa aaccaactac atctgcaact   1620
tctagtggaa ctactaagac atcaacaggg acagaaaaaa aagtttcagt aagtgctttt   1680
tctgatataa ttagtatgaa aaaccaacct gaacaaacaa ctaagaacgg tcaggtccaa   1740
gcttcttcta caagtcagag tccaaaatca agtcttagcc aaaacagcgg acaaaattca   1800
ataactttag aagaaaaatt tggacataca atttgaaagt tactaaatac atcacaaatt   1860
tataattttg aaaacaccca agggcaatat acaatctcaa tagaggatga taaattagtt   1920
tttgacttta agcttgtatc aaaagcagat cgagcaatta tttatcaagg atctaaaatt   1980
agtcttggtg gtctaattaa ttctgataag tctgcctatg atgagattaa acaatttagc   2040
ccagatcttt tccttgatgc aacaatagga gaacaatctg attataaaaa caagcaaaaa   2100
aaagattata ctttaaaatc gttaagagat ttaatgggta atggctttgt ttataaacca   2160
gaaactaaat cgaatccaca agaaaatgta ctaaaattac aaacaggatc agagcaaaaa   2220
aaacctctac cagggcttag atcaggatta atttatattg catttaccgt taataatatc   2280
aataaaaatg attataaacc tcattatcta ataagagata aaaatgataa aggtgtcttc   2340
attcagagat atcaagataa ggaagaacca aacgcttttg agattagaat tgattcatat   2400
```

-continued gagcctgatg acttcaggga taaacaattt caggctgctg atacgatatt agatgcaagt 2460
ggttcaattg atcctcgatc aaagaaaaaa attattctcc gtcaaaacgc tgattattta 2520
ttagtagttt ataagtcaaa aaaagatatt gtaacagagc tttattcact accttcagca 2580
caagataata acaaagaaaa gattgttaaa ataaaaaata gaaaatcatt tccctctcaa 2640
ggttatacag ttcaaggttc attattatat tctttattta gtcctaataa aattggagat 2700
agtcagaagc cagcccaaca accgccagct gtaagtataa aagcaatagc attatttgat 2760
aaaaaatcat ttacaaacga tacagaaaaa atgcgtttaa taaataatgc ttttattagt 2820
aattatataa aacaa 2835

<210> SEQ ID NO 14
<211> LENGTH: 945
<212> TYPE: PRT
<213> ORGANISM: Mycoplasma hyopneumoniae

<400> SEQUENCE: 14

Met Lys Leu Ala Lys Leu Leu Lys Lys Pro Phe Trp Leu Ile Thr Thr
1 5 10 15

Ile Ala Gly Ile Ser Leu Ser Leu Ser Ala Ala Val Gly Ile Val Val
20 25 30

Gly Ile Asn Ser Tyr Asn Lys Ser Tyr Tyr Ser Tyr Leu Asn Glu Asn
35 40 45

Pro Ser Gln Leu Lys Thr Thr Lys Thr Thr Lys Ile Ser Gln Gln Asp
50 55 60

Phe Asp Lys Ile Val Ser Asn Leu Lys Ile Arg Asp Asn Phe Lys Lys
65 70 75 80

Ile Ser Ala Lys Thr Ala Leu Ser Ala Val Lys Asn Asp Leu Tyr Arg
85 90 95

Tyr Asp Leu Val Arg Ala Phe Glu Phe Ser Ser Leu Glu Thr Asn Asn
100 105 110

Tyr Gln Ile Ser Phe Asp Leu Glu Asn Ala Val Val Asp Gln Asn Ser
115 120 125

Ile Lys Asn Val Leu Val Phe Ala Lys Ser Glu Lys Asp Gln Val Thr
130 135 140

Tyr Ser Lys Gln Ile Glu Leu Lys Gly Phe Ala Gln Asp Asp Glu Ala
145 150 155 160

Ala Gly Asp Leu Val Lys Phe Gln Ile Asp Gln Arg Lys Ser Phe Val
165 170 175

Asn Leu Tyr Lys Phe Asp Tyr Ser Phe Ser Glu Phe Gln Arg Ile Leu
180 185 190

Ser Glu Asn Tyr Arg Gln Ile Arg Asn Thr Asn Ser Phe Thr Arg Leu
195 200 205

Ala Asn Ala Leu Ile Ser Ser Lys Ala Ser Leu Ser Leu Tyr Asn Ser
210 215 220

Leu Gly Gln Pro Val Phe Leu Asp Glu Asn Tyr Arg Leu Glu Pro Val
225 230 235 240

Leu Asn Ser Lys Lys Glu Leu Asn Leu Leu Glu Lys Asn Lys Lys Leu
245 250 255

Tyr Leu Glu Leu Asn Leu Val Glu Lys Glu Ser Gln Lys Lys Ile Asn
260 265 270

Leu Thr Leu Glu Ile Arg Pro Leu Leu Thr Asn Gln Glu Phe Thr Ser
275 280 285

Glu Leu Lys Thr Leu Phe Glu Ser Asn Leu Asp Gln Asn Leu Ser Leu

-continued

```
    290                 295                 300

Asn Leu Glu Leu Lys Asn Ala Leu Phe His Asp Arg Thr Ser Phe Ser
305                 310                 315                 320

Glu Tyr Leu Tyr Gly Ser Pro Gln Gln Arg Thr Lys Thr Asp Glu Val
                325                 330                 335

Lys Gln Lys Ala Lys Glu Leu Lys Asp Leu Phe Gly Phe Arg Ser Ala
            340                 345                 350

Lys Phe Trp Gln Asp Thr Lys Phe Gly Thr Phe Tyr Val Ile Ile Lys
        355                 360                 365

Pro Gln Leu Leu Asp Pro Ala Lys Ile Ser Gln Glu Asp Lys Lys Lys
    370                 375                 380

Leu Leu Ala Asp Lys Lys Ile Arg Phe Glu Val Leu Thr Thr Leu Lys
385                 390                 395                 400

Arg Lys Ala Leu Asp Gln Gln Asp Val Leu Thr Asp Leu Pro Val Leu
                405                 410                 415

Val Asp Leu Ser Leu Asp Ser Asn Lys Tyr Glu Thr Ala Ile Ser Gln
            420                 425                 430

Ile Phe Asn Ser Thr Lys Thr Thr Lys Glu Phe Lys Met Gln Glu Tyr
        435                 440                 445

Glu Asp Arg Ala Lys Leu Ser Thr Lys Glu Ile Lys Glu Thr Ile Asp
    450                 455                 460

Lys Leu Ala Asn Leu Ala Ala Lys Val Ser Asn Leu Ser Glu Pro Ser
465                 470                 475                 480

Asp Glu Val Val Arg Ala Val Tyr Leu Leu Asn Thr Gly Lys Tyr Leu
                485                 490                 495

Phe Asp Asp Glu Ile Gln Gln Glu Lys Thr Asn Leu Lys Lys Ile Ile
            500                 505                 510

Glu Gln Ala Arg Met Lys Ala Asp Thr Lys Asn Leu Ala Pro Lys Val
        515                 520                 525

Pro Ser Pro Ile Gln Lys Pro Thr Thr Ser Ala Thr Ser Ser Gly Thr
    530                 535                 540

Thr Lys Thr Ser Thr Gly Thr Glu Lys Lys Val Ser Val Ser Ala Phe
545                 550                 555                 560

Ser Asp Ile Ile Ser Met Lys Asn Gln Pro Glu Gln Thr Thr Lys Asn
                565                 570                 575

Gly Gln Val Gln Ala Ser Ser Thr Ser Gln Ser Pro Lys Ser Ser Leu
            580                 585                 590

Ser Gln Asn Ser Gly Gln Asn Ser Ile Thr Leu Glu Glu Lys Phe Gly
        595                 600                 605

His Thr Ile Trp Lys Leu Leu Asn Thr Ser Gln Ile Tyr Asn Phe Glu
    610                 615                 620

Asn Thr Gln Gly Gln Tyr Thr Ile Ser Ile Glu Asp Asp Lys Leu Val
625                 630                 635                 640

Phe Asp Phe Lys Leu Val Ser Lys Ala Asp Arg Ala Ile Ile Tyr Gln
                645                 650                 655

Gly Ser Lys Ile Ser Leu Gly Gly Leu Ile Asn Ser Asp Lys Ser Ala
            660                 665                 670

Tyr Asp Glu Ile Lys Gln Phe Ser Pro Asp Leu Phe Leu Asp Ala Thr
        675                 680                 685

Ile Gly Glu Gln Ser Asp Tyr Lys Asn Lys Gln Lys Lys Asp Tyr Thr
    690                 695                 700

Leu Lys Ser Leu Arg Asp Leu Met Gly Asn Gly Phe Val Tyr Lys Pro
705                 710                 715                 720
```

-continued

```
Glu Thr Lys Ser Asn Pro Gln Glu Asn Val Leu Lys Leu Gln Thr Gly
                725                 730                 735

Ser Glu Gln Lys Lys Pro Leu Pro Gly Leu Arg Ser Gly Leu Ile Tyr
            740                 745                 750

Ile Ala Phe Thr Val Asn Asn Ile Asn Lys Asn Asp Tyr Lys Pro His
        755                 760                 765

Tyr Leu Ile Arg Asp Lys Asn Asp Lys Gly Val Phe Ile Gln Arg Tyr
    770                 775                 780

Gln Asp Lys Glu Glu Pro Asn Ala Phe Glu Ile Arg Ile Asp Ser Tyr
785                 790                 795                 800

Glu Pro Asp Asp Phe Arg Asp Lys Gln Phe Gln Ala Ala Asp Thr Ile
                805                 810                 815

Leu Asp Ala Ser Gly Ser Ile Asp Pro Arg Ser Lys Lys Lys Ile Ile
            820                 825                 830

Leu Arg Gln Asn Ala Asp Tyr Leu Leu Val Val Tyr Lys Ser Lys Lys
        835                 840                 845

Asp Ile Val Thr Glu Leu Tyr Ser Leu Pro Ser Ala Gln Asp Asn Asn
    850                 855                 860

Lys Glu Lys Ile Val Lys Ile Lys Asn Arg Lys Ser Phe Pro Ser Gln
865                 870                 875                 880

Gly Tyr Thr Val Gln Gly Ser Leu Leu Tyr Ser Leu Phe Ser Pro Asn
                885                 890                 895

Lys Ile Gly Asp Ser Gln Lys Pro Ala Gln Gln Pro Pro Ala Val Ser
            900                 905                 910

Ile Lys Ala Ile Ala Leu Phe Asp Lys Lys Ser Phe Thr Asn Asp Thr
        915                 920                 925

Glu Lys Met Arg Leu Ile Asn Asn Ala Phe Ile Ser Asn Tyr Ile Lys
    930                 935                 940

Gln
945
```

<210> SEQ ID NO 15
<211> LENGTH: 1380
<212> TYPE: DNA
<213> ORGANISM: Mycoplasma hyopneumoniae

<400> SEQUENCE: 15

```
gtgattgagg gcttaaaatc aaaggcaaat actcaaaaaa cagaaaaaaa tagccccaca      60

caaccgaaaa aaccagaggt ttcactagct aaaacaacag aaaattcagc aaaaacagtc     120

aaggtaagca cttttgcaga agaagctaag ggtcaaagtc aaagtcagca aacacaacca     180

gtttccactt catcgcctca aactagtcaa aattcagttt ctaattccac aagcagtacg     240

aatttagcct tagaaaatga aaaatttggg acaagcattt gaacagcttt taatttcgct     300

aatatttata atcttgaaaa tacaaaaagc gaatatgaga tctcaacttt aggaaataag     360

ctattttttg attttaaatt agttgataaa actaatcaaa atctaatttt ggctcagtcc     420

aaaattagtc ttaataatat tattaattct aataaatctg cctatgatat aattaagaaa     480

ttcaatcccg atgtatttct agatggaaca attaattatc aagatcaagg aaaagataaa     540

aaagaattta tcctaaaaga tttaagtgat aataaattaa tatttaaatc agaagatgca     600

attcaaactg atcaaggttt agagctaaag aaacctttga aattaagccc gacaacgaac     660

tcttcttcta ctacttcaca aaagactaat aaaaaggatg atattggagt gttttgacta     720

gcgcttcaag ttaataatat aacagatttc aaaaatcatc atctaatatc cgatggaaaa     780
```

-continued

```
ggaaatggaa taattcttaa caaatacaag gtcaaggatg aaactggtta tcaattagga    840

ctagaatatc ctggaaggaa tgaaaataat tttattactg atattgttga tctagtcgac    900

ggttttatca aatttatttt tggatgaaaa caagaccaaa ataatagtag ttttttggac    960

acaccctcac ttttaattga ttttaacaag tataaaaaca aaaaaaatac tgaatttatc   1020

aaggcgaata caaaaattct tttagaggtt gtagaaaaca atgatcgact ttctgtttca   1080

gtattttctt ctcaagcagg aaaaaatcat aaacaaatta tagaaaatag aatgcataga   1140

agtttacatt ataaaaaagc agacaaagcc aaagaaggtg taagcccaat cccaagtttt   1200

actgatattt taaatgaatt acaaattgga gctactgata gcgatccaaa aactcaaaag   1260

gcaccagtaa cattcaaagc gtttatgatg tcaaatgata aaaatctagt atttggatca   1320

aacattaata atcaagaaat tcgccaagcg cttattgacg cttatatagt tgataagaat   1380
```

<210> SEQ ID NO 16
<211> LENGTH: 460
<212> TYPE: PRT
<213> ORGANISM: Mycoplasma hyopneumoniae

<400> SEQUENCE: 16

```
Val Ile Glu Gly Leu Lys Ser Lys Ala Asn Thr Gln Lys Thr Glu Lys
 1               5                  10                  15

Asn Ser Pro Thr Gln Pro Lys Lys Pro Glu Val Ser Leu Ala Lys Thr
            20                  25                  30

Thr Glu Asn Ser Ala Lys Thr Val Lys Val Ser Thr Phe Ala Glu Glu
        35                  40                  45

Ala Lys Gly Gln Ser Gln Ser Gln Gln Thr Gln Pro Val Ser Thr Ser
    50                  55                  60

Ser Pro Gln Thr Ser Gln Asn Ser Val Ser Asn Ser Thr Ser Ser Thr
65                  70                  75                  80

Asn Leu Ala Leu Glu Asn Glu Lys Phe Gly Thr Ser Ile Trp Thr Ala
                85                  90                  95

Phe Asn Phe Ala Asn Ile Tyr Asn Leu Glu Asn Thr Lys Ser Glu Tyr
            100                 105                 110

Glu Ile Ser Thr Leu Gly Asn Lys Leu Phe Phe Asp Phe Lys Leu Val
        115                 120                 125

Asp Lys Thr Asn Gln Asn Leu Ile Leu Ala Gln Ser Lys Ile Ser Leu
    130                 135                 140

Asn Asn Ile Ile Asn Ser Asn Lys Ser Ala Tyr Asp Ile Ile Lys Lys
145                 150                 155                 160

Phe Asn Pro Asp Val Phe Leu Asp Gly Thr Ile Asn Tyr Gln Asp Gln
                165                 170                 175

Gly Lys Asp Lys Lys Glu Phe Ile Leu Lys Asp Leu Ser Asp Asn Lys
            180                 185                 190

Leu Ile Phe Lys Ser Glu Asp Ala Ile Gln Thr Asp Gln Gly Leu Glu
        195                 200                 205

Leu Lys Lys Pro Leu Lys Leu Ser Pro Thr Thr Asn Ser Ser Ser Thr
    210                 215                 220

Thr Ser Gln Lys Thr Asn Lys Lys Asp Asp Ile Gly Val Phe Trp Leu
225                 230                 235                 240

Ala Leu Gln Val Asn Asn Ile Thr Asp Phe Lys Asn His His Leu Ile
                245                 250                 255

Ser Asp Gly Lys Gly Asn Gly Ile Ile Leu Asn Lys Tyr Lys Val Lys
            260                 265                 270
```

-continued

```
Asp Glu Thr Gly Tyr Gln Leu Gly Leu Glu Tyr Pro Gly Arg Asn Glu
        275                 280                 285

Asn Asn Phe Ile Thr Asp Ile Val Asp Leu Val Asp Gly Phe Ile Lys
    290                 295                 300

Phe Ile Phe Gly Trp Lys Gln Asp Gln Asn Asn Ser Ser Phe Leu Asp
305                 310                 315                 320

Thr Pro Ser Leu Leu Ile Asp Phe Asn Lys Tyr Lys Asn Lys Lys Asn
                325                 330                 335

Thr Glu Phe Ile Lys Ala Asn Thr Lys Ile Leu Leu Glu Val Val Glu
            340                 345                 350

Asn Asn Asp Arg Leu Ser Val Ser Val Phe Ser Ser Gln Ala Gly Lys
        355                 360                 365

Asn His Lys Gln Ile Ile Glu Asn Arg Met His Arg Ser Leu His Tyr
    370                 375                 380

Lys Lys Ala Asp Lys Ala Lys Glu Gly Val Ser Pro Ile Pro Ser Phe
385                 390                 395                 400

Thr Asp Ile Leu Asn Glu Leu Gln Ile Gly Ala Thr Asp Ser Asp Pro
                405                 410                 415

Lys Thr Gln Lys Ala Pro Val Thr Phe Lys Ala Phe Met Met Ser Asn
            420                 425                 430

Asp Lys Asn Leu Val Phe Gly Ser Asn Ile Asn Asn Gln Glu Ile Arg
        435                 440                 445

Gln Ala Leu Ile Asp Ala Tyr Ile Val Asp Lys Asn
    450                 455                 460


<210> SEQ ID NO 17
<211> LENGTH: 1353
<212> TYPE: DNA
<213> ORGANISM: Mycoplasma hyopneumoniae

<400> SEQUENCE: 17

atgaagttag caaaattact taaaaaacct ttttgattaa taacaacaat tgccggaatt      60

agtcttagtt tatcagccgc tgttggtaca gttgtcggaa ttaattctta taataaatca     120

tattattctt atctaaatca gatcccgagt cagctaaaag tagcaaaaaa tgctaaaatt     180

agtcaggaaa aatttgattc aattgtttta aatcttaaaa ttaaagataa ttttaaaaaa     240

tgatcggcaa aaacagtttt aactgctgcc aaaagtgatc tttatcgtta taatcttgtt     300

tctgcttttg atttaagtga actaataaac aatgattatt tagtaagttt tgatcttgaa     360

aatgcagtag ttgatcaaaa ttcaattaaa aatgttgtta tttatgcaaa atctgataag     420

gatcaaataa cttattcaaa acaaattgta cttaaaggct ttggaaatac agaacaagcg     480

agaactaatt ttgattttag ccaaattgat tcaagcaagt cttttgttga tctttcaagg     540

gcaaatctaa ctttgacgga attccaaatt ttacttgccc aaaattttga aaatgaaaga     600

ggaagtaatt gattttcacg acttgaaaga gctttggttg catcaaaagc gagtctttca     660

ctttataatt ccttaggaga acccgtattt ttaggcccag attatcaatt agacccagtt     720

ttggaccgaa aaaaattatt aactttgtta aataaagatg gaaaattagt tcttggactt     780

aatttagtgc aaatttcaac taaaaaaact atgaatttaa atcttgaagt tcgcggcgcg     840

atttcaaatc aggaaatttc taaaattcta aaatcctgac ttgaaacaaa tcttcaaggc     900

aaattaaaaa ccaaagatga tttgcaaatg gcactagtaa aagataaaat tagcctctct     960

gattattgat atggatctcc gaattcaaaa gtaaatacat cccaaatttt aacaaaaagt    1020
```

-continued

```
aaagaattta aagatctttt tgatttaagt gagacaaatt tttttcttaa taccaaaatc   1080

ggaactgtct atttaagtat tattcccaaa cttttagatc caagtcagat ttctgttgtt   1140

gataagaaaa aactagttga aaatcaaaaa attcgctttg aaattactgc ttctttaaaa   1200

cgaaaagcta ttgataaaaa atttatcatc caggatcttc cagtttttgt tgatctaaaa   1260

gttgatttta ataaatacca agccgctgtt gcccaaatgt ttggaacgat aaaagcagtt   1320

aaagaatttt caatgcctga agatcaagat gca                               1353
```

<210> SEQ ID NO 18
<211> LENGTH: 451
<212> TYPE: PRT
<213> ORGANISM: Mycoplasma hyopneumoniae

<400> SEQUENCE: 18

```
Met Lys Leu Ala Lys Leu Leu Lys Lys Pro Phe Trp Leu Ile Thr Thr
 1               5                  10                  15

Ile Ala Gly Ile Ser Leu Ser Leu Ser Ala Ala Val Gly Thr Val Val
            20                  25                  30

Gly Ile Asn Ser Tyr Asn Lys Ser Tyr Tyr Ser Tyr Leu Asn Gln Ile
        35                  40                  45

Pro Ser Gln Leu Lys Val Ala Lys Asn Ala Lys Ile Ser Gln Glu Lys
    50                  55                  60

Phe Asp Ser Ile Val Leu Asn Leu Lys Ile Lys Asp Asn Phe Lys Lys
65                  70                  75                  80

Trp Ser Ala Lys Thr Val Leu Thr Ala Ala Lys Ser Asp Leu Tyr Arg
                85                  90                  95

Tyr Asn Leu Val Ser Ala Phe Asp Leu Ser Glu Leu Ile Asn Asn Asp
            100                 105                 110

Tyr Leu Val Ser Phe Asp Leu Glu Asn Ala Val Val Asp Gln Asn Ser
        115                 120                 125

Ile Lys Asn Val Val Ile Tyr Ala Lys Ser Asp Lys Asp Gln Ile Thr
    130                 135                 140

Tyr Ser Lys Gln Ile Val Leu Lys Gly Phe Gly Asn Thr Glu Gln Ala
145                 150                 155                 160

Arg Thr Asn Phe Asp Phe Ser Gln Ile Asp Ser Ser Lys Ser Phe Val
                165                 170                 175

Asp Leu Ser Arg Ala Asn Leu Thr Leu Thr Glu Phe Gln Ile Leu Leu
            180                 185                 190

Ala Gln Asn Phe Glu Asn Glu Arg Gly Ser Asn Trp Phe Ser Arg Leu
        195                 200                 205

Glu Arg Ala Leu Val Ala Ser Lys Ala Ser Leu Ser Leu Tyr Asn Ser
    210                 215                 220

Leu Gly Glu Pro Val Phe Leu Gly Pro Asp Tyr Gln Leu Asp Pro Val
225                 230                 235                 240

Leu Asp Arg Lys Lys Leu Leu Thr Leu Leu Asn Lys Asp Gly Lys Leu
                245                 250                 255

Val Leu Gly Leu Asn Leu Val Gln Ile Ser Thr Lys Lys Thr Met Asn
            260                 265                 270

Leu Asn Leu Glu Val Arg Gly Ala Ile Ser Asn Gln Glu Ile Ser Lys
        275                 280                 285

Ile Leu Lys Ser Trp Leu Glu Thr Asn Leu Gln Gly Lys Leu Lys Thr
    290                 295                 300

Lys Asp Asp Leu Gln Met Ala Leu Val Lys Asp Lys Ile Ser Leu Ser
305                 310                 315                 320
```

-continued

Asp Tyr Trp Tyr Gly Ser Pro Asn Ser Lys Val Asn Thr Ser Gln Ile
325 330 335

Leu Thr Lys Ser Lys Glu Phe Lys Asp Leu Phe Asp Leu Ser Glu Thr
340 345 350

Asn Phe Phe Leu Asn Thr Lys Ile Gly Thr Val Tyr Leu Ser Ile Ile
355 360 365

Pro Lys Leu Leu Asp Pro Ser Gln Ile Ser Val Val Asp Lys Lys Lys
370 375 380

Leu Val Glu Asn Gln Lys Ile Arg Phe Glu Ile Thr Ala Ser Leu Lys
385 390 395 400

Arg Lys Ala Ile Asp Lys Lys Phe Ile Ile Gln Asp Leu Pro Val Phe
405 410 415

Val Asp Leu Lys Val Asp Phe Asn Lys Tyr Gln Ala Ala Val Ala Gln
420 425 430

Met Phe Gly Thr Ile Lys Ala Val Lys Glu Phe Ser Met Pro Glu Asp
435 440 445

Gln Asp Ala
450

<210> SEQ ID NO 19
<211> LENGTH: 5637
<212> TYPE: DNA
<213> ORGANISM: Mycoplasma hyopneumoniae

<400> SEQUENCE: 19
atgaaaaaca aaaaatcaac attactatta gccacagcgg cggcaattat tggttcaact 60
gtttttggga cagttgttgg cttggcttca aaagttaaat atcggggtgt aaatccaact 120
caaggagtaa tatctcaatt aggactgatt gattctgttg catttaaacc ttcgattgca 180
aattttacaa gcgattatca aagtgttaaa aaagcacttt taaatgggaa aacctttgat 240
ccaaaaagtt cagaatttac tgattttgtc tcaaaatttg actttttgac taataatggg 300
agaaccgttt tggagatccc gaaaaaatat caggtggtta tctcggaatt tagccccgag 360
gatgataaag aacgttttcg tcttggattt catctaaaag aaaaacttga agatggaaat 420
atagctcaat cagcaactaa atttatttat cttttaccac ttgatatgcc caaagcggcc 480
ctgggtcaat attcttatat cgttgataaa aattttaata atttaattat ccatccttta 540
tctaattttt ctgctcaatc aataaagccg cttgcactga cccgttcaag tgattttata 600
gcaaaactta atcagtttaa aaatcaggac gaactttgag tttatcttga aaaattcttt 660
gatcttgaag ctctaaaagc aaatattcgt ttgcagacag ccgattttag ttttgaaaaa 720
ggcaatttag ttgatccttt tgtttattct tttattagaa atccgcaaaa tggaaaagaa 780
tgagctagtg atcttaatca agatcaaaaa accgtcagac tttatcttcg aaccgaattt 840
agtcctcagg ctaaaaccat tttaaaagac tataaataca aagatgagac tttcttaagt 900
agtatcgatt taaaagcaag taatggaact agtttatttg ctaatgaaaa tgatctaaaa 960
gatcaattag atgttgatct tttagatgtc tctgattatt ttggaggcca atcagagaca 1020
attactagta attcccaagt taaacctgtc cctgctagtg agagatcttt aaaagatcgg 1080
gttaaattta aaaaagatca gcaaaaacca agaattgaga aatttagttt atatgaatat 1140
gatgctctaa gtttttattc ccaacttcag gaattagttt ctaaacctaa ttcaattaaa 1200
gatttagtta atgcaacttt agctcgtaat cttcggtttt cattaggaaa atataatttt 1260
ctttttgatg atttagccag tcatcttgat tatacttttt tagtttcaaa agcaaaaatt 1320

-continued

```
aaacaaagtt caattacaaa aaaattattc attgaattac caatcaaaat tagtcttaaa   1380
tcttcaattt taggtgatca agaacctaat attaaaactt tattcgaaaa agaagtaact   1440
tttaaattag ataacttccg tgatgttgaa atcgaaaaag cttttggact tttatatcca   1500
ggtgttaatg aagaacttga acaagcccga agagagcaaa gagcaagttt ggaaaaagaa   1560
aaagcgaaaa agggtcttaa agaatttagc cagcaaaaag atgagaattt aaaagcaata   1620
aataatcaag atggtcttga agaagatgat aatattactg aaagacttcc tgagaattcc   1680
ccgattcaat atcagcaaga aaaggccggt ttaggttcaa gtccggataa accttatatg   1740
ataaaggatg tccaaaatca acgttattat ctagcaaaat cacaaattca agaactaatt   1800
aaggccaaag attataccaa attagccaaa cttttatcca atagacatac ttataatatt   1860
tctttaagat taaaagaaca actttttgaa gtaaatccaa gaattccaag ctctagagat   1920
atagaaaatg caaaatttgt tctagataaa accgaaaaaa ataaatactg gcagatttat   1980
tcaagtgctt ctcctgcttt ccaaaataaa tgatcacttt ttggatatta ccgttattta   2040
ttaggtcttg atccaaaaca aacaatccac gaattagtaa aattaggaca aaaagcgggt   2100
cttcaatttg aaggatatga aaatcttcct tctgatttca atcttgaaga tcttaagaat   2160
attaggatta aaacaccttt atttagtcaa aaagataatt tcaaattatc tttacttgat   2220
tttaataatt attatgatgg tgaaattaaa gccccagaat ttggtcttcc tttattttta   2280
ccaaaagaat taagaaaaaa tagttcaaat attggtagtt ctcaaaactc taatagccct   2340
tgagaacaag aaattattag ccaatttaaa gatcaaaatc tatctaatca ggatcagtta   2400
gcccagttta gtactaaaat ctgggaaaaa atcattggtg atgaaaacga atttgatcaa   2460
aataacaggc ttcagtataa acttttaaaa gatcttcaag aatcttgaat taacaaaact   2520
cgcgataatc tttattggac ttatctaggt gataaactta aagttaaacc aaaaaaataat   2580
ttagatgcta aatttagaca aatttccaat ttacaagagc ttttaactgc tttttatacc   2640
tcagctgctc tttctaataa ctgaaattat tatcaagatt caggggcaaa gtcaactatt   2700
atttttgaag aaatagctga gctagatcca aaagtaaaag aaaaagtagg agctgatgtt   2760
tatcaattaa aattccatta tgcaatcggt tttgatgata atgctggcaa gtttaatcaa   2820
gaagtaattc gttcttcaag tagaacaatt tatcttaaaa cctcagggaa atccaaatta   2880
gaagcagata caattgatca acttaatcaa gcagttgaaa atgcaccttt aggtcttcaa   2940
agtttttatc ttgatactga aagatttggg gttttccaaa aattagcaac ttccttagca   3000
gttcaacata aacaaaaaga aaaaccacta cctaaaaaac taaataatga tggctatact   3060
ttaattcatg ataaacttaa aaaaccagta attccccaaa ttagttcaag tcccgaaaaa   3120
gattgatttg aaggtaaatt aaatcaaaac gggcaaagcc aaaatgtaaa tgtctcaact   3180
tttggttcaa taatcgagtc cccttatttt agtactaatt tccaagaaga agctgattta   3240
gaccaagaag gacaagatga ttcaaaacaa ggaaataaga gcctagataa tcaagaagca   3300
ggtcttttaa aacaaaaact ggcaatttta ttagggaatc aatttatcca atattatcaa   3360
caaaatgata aagaaattga attcgagatt atcaatgttg agaaagtttc agagcttagt   3420
ttccgcgttg aatttaaatt agcaaaaact cttgaagaca acggaaaaac tattcgagtt   3480
ttatcagatg agacaatgtc attaattgtt aatactacaa ttgaaaaagc accagaaatg   3540
agtgctgctc ccgaagtatt cgatactaaa tgggttgagc aatatgatcc aagaaccccg   3600
cttgcggcta agacaaagtt tgtcttaaaa ttcaaagatc aaataccagt tgatgccagc   3660
```

-continued

```
ggaaatattt ctgataaatg actagcaagt attcctttgg tgattcacca gcaaatgttg   3720
cgtcttagcc cggtagttaa aacaataaga gagcttggtc taaaaactga acaacaacaa   3780
caacaacaac aacaacaaca aaagaaagct gttagaaaag aagaagaact ggaaacctat   3840
aatccaaaag acgagtttaa tattcttaat cctttaacaa aagctcaccg tcttacctta   3900
tcaaatttag taaataatga tccaaattat aaaattgaag atttaaaagt aatcaaaaat   3960
gaagcaggtg atcatcaatt agaattttct ctaagagcta ataatatcaa aagattaatg   4020
aatacaccaa ttacttttgc tgattataat cccttttttct attttaatga ggactgaaga   4080
aatatagata aatatttaaa taataaagga aatgtgagtt ctcaacaaca acaacaacaa   4140
caacaacaac caggcggggg taatcaaggc tcgggtctaa tccaaagact taataaaaat   4200
attaagcccg aaacttttac ccccgcactc atagctctta aacgagataa taatactaat   4260
ctttctaact attctgataa aataataatg atcaaaccaa aatatttggt tgaacgatca   4320
attggtgttc cctgatcaac cggccttgat ggttatattg gttcagaaca actcaagggc   4380
ggaacttcct caaacggtca aaagcgattt aagcaagatt ttattcaggc tttaggtctt   4440
aaaaacactg aatatcatgg taaactaggt ctttcaatta gaatttttga tcctggaaat   4500
gaactagcaa aaattaagga tgcttcaaat aaaaaagggg aagaaaaact gttaaaatca   4560
tatgatttat ttaaaaacta tttaaatgaa tatgagaaaa aatcccctaa aattgctaag   4620
ggatgaacaa atattcatcc tgatcaaaaa gaatatccaa atccaaatca aaaactacct   4680
gaaaattatc ttaacctagt tttaaatcaa ccttgaaagg ttactttata taattcaagt   4740
gattttatta ctaatttatt tgttgaacct gaaggctcag atcggggatc tggagcaaaa   4800
ttaaaacaag taatccagaa gcaagttaat aataactatg ctgactgggg gtctgcatat   4860
ctcacgttct ggtatgataa agatatcatt accaatcagc caaatgttat aactgctaac   4920
attgctgatg tctttattaa agatgtaaag gaacttgaag ataatacaaa actaattgct   4980
ccaaatatta ctcaatgatg gccaaatatt agcggctcaa aggagaaatt ttataagcca   5040
acagtgtttt ttggtaattg agaaaatgaa aacagcaata tgaattccca ggggcagacc   5100
cctacctggg agaagatcag agaaggattt gctctccaag cgcttaaatc cagctttgat   5160
caaaaaacaa ggacatttgt ccttacaaca aatgctcctt tacctttatg aaaatacgga   5220
ccattaggtt tccaaaatgg gccgaatttc aaaacacaag attgaaggct tgttttccaa   5280
aatgatgata accaaatagc cgcgctaaga gtccaggagc aagatcgccc agaaaaatca   5340
agcgaagata aagacaagca aaaatggatt aaatttaaag ttgttatccc tgaagaaatg   5400
tttaattccg gtaatatacg ttttgttggg gtaatgcaga tccaaggtcc taatacttta   5460
tgacttccag tgattaattc ttcggttatc tatgacttct atcgcggaac aggagattct   5520
aacgatgtcg ccaatcttaa tgtagctcct tgacaggtta aaacaatcgc atttacaaat   5580
aacgccttta ataatgtttt caaagagttt aatatctcta aaaaaatagt agaataa      5637
```

<210> SEQ ID NO 20
<211> LENGTH: 1878
<212> TYPE: PRT
<213> ORGANISM: Mycoplasma hyopneumoniae

<400> SEQUENCE: 20

```
Met Lys Asn Lys Lys Ser Thr Leu Leu Leu Ala Thr Ala Ala Ala Ile
 1               5                  10                  15

Ile Gly Ser Thr Val Phe Gly Thr Val Val Gly Leu Ala Ser Lys Val
            20                  25                  30
```

-continued

```
Lys Tyr Arg Gly Val Asn Pro Thr Gln Gly Val Ile Ser Gln Leu Gly
        35                  40                  45

Leu Ile Asp Ser Val Ala Phe Lys Pro Ser Ile Ala Asn Phe Thr Ser
    50                  55                  60

Asp Tyr Gln Ser Val Lys Lys Ala Leu Leu Asn Gly Lys Thr Phe Asp
65                  70                  75                  80

Pro Lys Ser Ser Glu Phe Thr Asp Phe Val Ser Lys Phe Asp Phe Leu
                85                  90                  95

Thr Asn Asn Gly Arg Thr Val Leu Glu Ile Pro Lys Lys Tyr Gln Val
            100                 105                 110

Val Ile Ser Glu Phe Ser Pro Glu Asp Asp Lys Glu Arg Phe Arg Leu
        115                 120                 125

Gly Phe His Leu Lys Glu Lys Leu Glu Asp Gly Asn Ile Ala Gln Ser
    130                 135                 140

Ala Thr Lys Phe Ile Tyr Leu Leu Pro Leu Asp Met Pro Lys Ala Ala
145                 150                 155                 160

Leu Gly Gln Tyr Ser Tyr Ile Val Asp Lys Asn Phe Asn Asn Leu Ile
                165                 170                 175

Ile His Pro Leu Ser Asn Phe Ser Ala Gln Ser Ile Lys Pro Leu Ala
            180                 185                 190

Leu Thr Arg Ser Ser Asp Phe Ile Ala Lys Leu Asn Gln Phe Lys Asn
        195                 200                 205

Gln Asp Glu Leu Trp Val Tyr Leu Glu Lys Phe Phe Asp Leu Glu Ala
    210                 215                 220

Leu Lys Ala Asn Ile Arg Leu Gln Thr Ala Asp Phe Ser Phe Glu Lys
225                 230                 235                 240

Gly Asn Leu Val Asp Pro Phe Val Tyr Ser Phe Ile Arg Asn Pro Gln
                245                 250                 255

Asn Gly Lys Glu Trp Ala Ser Asp Leu Asn Gln Asp Gln Lys Thr Val
            260                 265                 270

Arg Leu Tyr Leu Arg Thr Glu Phe Ser Pro Gln Ala Lys Thr Ile Leu
        275                 280                 285

Lys Asp Tyr Lys Tyr Lys Asp Glu Thr Phe Leu Ser Ser Ile Asp Leu
    290                 295                 300

Lys Ala Ser Asn Gly Thr Ser Leu Phe Ala Asn Glu Asn Asp Leu Lys
305                 310                 315                 320

Asp Gln Leu Asp Val Asp Leu Leu Asp Val Ser Asp Tyr Phe Gly Gly
                325                 330                 335

Gln Ser Glu Thr Ile Thr Ser Asn Ser Gln Val Lys Pro Val Pro Ala
            340                 345                 350

Ser Glu Arg Ser Leu Lys Asp Arg Val Lys Phe Lys Lys Asp Gln Gln
        355                 360                 365

Lys Pro Arg Ile Glu Lys Phe Ser Leu Tyr Glu Tyr Asp Ala Leu Ser
    370                 375                 380

Phe Tyr Ser Gln Leu Gln Glu Leu Val Ser Lys Pro Asn Ser Ile Lys
385                 390                 395                 400

Asp Leu Val Asn Ala Thr Leu Ala Arg Asn Leu Arg Phe Ser Leu Gly
                405                 410                 415

Lys Tyr Asn Phe Leu Phe Asp Asp Leu Ala Ser His Leu Asp Tyr Thr
            420                 425                 430

Phe Leu Val Ser Lys Ala Lys Ile Lys Gln Ser Ser Ile Thr Lys Lys
        435                 440                 445
```

-continued

```
Leu Phe Ile Glu Leu Pro Ile Lys Ile Ser Leu Lys Ser Ser Ile Leu
    450                 455                 460

Gly Asp Gln Glu Pro Asn Ile Lys Thr Leu Phe Glu Lys Glu Val Thr
465                 470                 475                 480

Phe Lys Leu Asp Asn Phe Arg Asp Val Glu Ile Glu Lys Ala Phe Gly
                485                 490                 495

Leu Leu Tyr Pro Gly Val Asn Glu Glu Leu Glu Gln Ala Arg Arg Glu
            500                 505                 510

Gln Arg Ala Ser Leu Glu Lys Glu Lys Ala Lys Lys Gly Leu Lys Glu
        515                 520                 525

Phe Ser Gln Gln Lys Asp Glu Asn Leu Lys Ala Ile Asn Asn Gln Asp
    530                 535                 540

Gly Leu Glu Glu Asp Asp Asn Ile Thr Glu Arg Leu Pro Glu Asn Ser
545                 550                 555                 560

Pro Ile Gln Tyr Gln Gln Glu Lys Ala Gly Leu Gly Ser Ser Pro Asp
                565                 570                 575

Lys Pro Tyr Met Ile Lys Asp Val Gln Asn Gln Arg Tyr Tyr Leu Ala
            580                 585                 590

Lys Ser Gln Ile Gln Glu Leu Ile Lys Ala Lys Asp Tyr Thr Lys Leu
        595                 600                 605

Ala Lys Leu Leu Ser Asn Arg His Thr Tyr Asn Ile Ser Leu Arg Leu
    610                 615                 620

Lys Glu Gln Leu Phe Glu Val Asn Pro Arg Ile Pro Ser Ser Arg Asp
625                 630                 635                 640

Ile Glu Asn Ala Lys Phe Val Leu Asp Lys Thr Glu Lys Asn Lys Tyr
                645                 650                 655

Trp Gln Ile Tyr Ser Ser Ala Ser Pro Ala Phe Gln Asn Lys Trp Ser
            660                 665                 670

Leu Phe Gly Tyr Tyr Arg Tyr Leu Leu Gly Leu Asp Pro Lys Gln Thr
        675                 680                 685

Ile His Glu Leu Val Lys Leu Gly Gln Lys Ala Gly Leu Gln Phe Glu
    690                 695                 700

Gly Tyr Glu Asn Leu Pro Ser Asp Phe Asn Leu Glu Asp Leu Lys Asn
705                 710                 715                 720

Ile Arg Ile Lys Thr Pro Leu Phe Ser Gln Lys Asp Asn Phe Lys Leu
                725                 730                 735

Ser Leu Leu Asp Phe Asn Asn Tyr Tyr Asp Gly Glu Ile Lys Ala Pro
            740                 745                 750

Glu Phe Gly Leu Pro Leu Phe Leu Pro Lys Glu Leu Arg Lys Asn Ser
        755                 760                 765

Ser Asn Ile Gly Ser Ser Gln Asn Ser Asn Ser Pro Trp Glu Gln Glu
    770                 775                 780

Ile Ile Ser Gln Phe Lys Asp Gln Asn Leu Ser Asn Gln Asp Gln Leu
785                 790                 795                 800

Ala Gln Phe Ser Thr Lys Ile Trp Glu Lys Ile Ile Gly Asp Glu Asn
                805                 810                 815

Glu Phe Asp Gln Asn Asn Arg Leu Gln Tyr Lys Leu Leu Lys Asp Leu
            820                 825                 830

Gln Glu Ser Trp Ile Asn Lys Thr Arg Asp Asn Leu Tyr Trp Thr Tyr
        835                 840                 845

Leu Gly Asp Lys Leu Lys Val Lys Pro Lys Asn Asn Leu Asp Ala Lys
    850                 855                 860

Phe Arg Gln Ile Ser Asn Leu Gln Glu Leu Leu Thr Ala Phe Tyr Thr
```

-continued

```
865                 870                 875                 880

Ser Ala Ala Leu Ser Asn Asn Trp Asn Tyr Tyr Gln Asp Ser Gly Ala
                885                 890                 895

Lys Ser Thr Ile Ile Phe Glu Glu Ile Ala Glu Leu Asp Pro Lys Val
            900                 905                 910

Lys Glu Lys Val Gly Ala Asp Val Tyr Gln Leu Lys Phe His Tyr Ala
        915                 920                 925

Ile Gly Phe Asp Asp Asn Ala Gly Lys Phe Asn Gln Glu Val Ile Arg
    930                 935                 940

Ser Ser Ser Arg Thr Ile Tyr Leu Lys Thr Ser Gly Lys Ser Lys Leu
945                 950                 955                 960

Glu Ala Asp Thr Ile Asp Gln Leu Asn Gln Ala Val Glu Asn Ala Pro
                965                 970                 975

Leu Gly Leu Gln Ser Phe Tyr Leu Asp Thr Glu Arg Phe Gly Val Phe
            980                 985                 990

Gln Lys Leu Ala Thr Ser Leu Ala Val Gln His Lys Gln Lys Glu Lys
        995                 1000                1005

Pro Leu Pro Lys Lys Leu Asn Asn Asp Gly Tyr Thr Leu Ile His Asp
    1010                1015                1020

Lys Leu Lys Lys Pro Val Ile Pro Gln Ile Ser Ser Ser Pro Glu Lys
1025                1030                1035                1040

Asp Trp Phe Glu Gly Lys Leu Asn Gln Asn Gly Gln Ser Gln Asn Val
                1045                1050                1055

Asn Val Ser Thr Phe Gly Ser Ile Ile Glu Ser Pro Tyr Phe Ser Thr
            1060                1065                1070

Asn Phe Gln Glu Glu Ala Asp Leu Asp Gln Glu Gly Gln Asp Asp Ser
        1075                1080                1085

Lys Gln Gly Asn Lys Ser Leu Asp Asn Gln Glu Ala Gly Leu Leu Lys
    1090                1095                1100

Gln Lys Leu Ala Ile Leu Leu Gly Asn Gln Phe Ile Gln Tyr Tyr Gln
1105                1110                1115                1120

Gln Asn Asp Lys Glu Ile Glu Phe Glu Ile Ile Asn Val Glu Lys Val
                1125                1130                1135

Ser Glu Leu Ser Phe Arg Val Glu Phe Lys Leu Ala Lys Thr Leu Glu
            1140                1145                1150

Asp Asn Gly Lys Thr Ile Arg Val Leu Ser Asp Glu Thr Met Ser Leu
        1155                1160                1165

Ile Val Asn Thr Thr Ile Glu Lys Ala Pro Glu Met Ser Ala Ala Pro
    1170                1175                1180

Glu Val Phe Asp Thr Lys Trp Val Glu Gln Tyr Asp Pro Arg Thr Pro
1185                1190                1195                1200

Leu Ala Ala Lys Thr Lys Phe Val Leu Lys Phe Lys Asp Gln Ile Pro
                1205                1210                1215

Val Asp Ala Ser Gly Asn Ile Ser Asp Lys Trp Leu Ala Ser Ile Pro
            1220                1225                1230

Leu Val Ile His Gln Gln Met Leu Arg Leu Ser Pro Val Val Lys Thr
        1235                1240                1245

Ile Arg Glu Leu Gly Leu Lys Thr Glu Gln Gln Gln Gln Gln Gln Gln
    1250                1255                1260

Gln Gln Gln Lys Lys Ala Val Arg Lys Glu Glu Glu Leu Glu Thr Tyr
1265                1270                1275                1280

Asn Pro Lys Asp Glu Phe Asn Ile Leu Asn Pro Leu Thr Lys Ala His
                1285                1290                1295
```

-continued

```
Arg Leu Thr Leu Ser Asn Leu Val Asn Asn Asp Pro Asn Tyr Lys Ile
            1300                1305                1310

Glu Asp Leu Lys Val Ile Lys Asn Glu Ala Gly Asp His Gln Leu Glu
        1315                1320                1325

Phe Ser Leu Arg Ala Asn Asn Ile Lys Arg Leu Met Asn Thr Pro Ile
    1330                1335                1340

Thr Phe Ala Asp Tyr Asn Pro Phe Phe Tyr Phe Asn Glu Asp Trp Arg
1345                1350                1355                1360

Asn Ile Asp Lys Tyr Leu Asn Asn Lys Gly Asn Val Ser Ser Gln Gln
                1365                1370                1375

Gln Gln Gln Gln Gln Gln Gln Pro Gly Gly Gly Asn Gln Gly Ser Gly
            1380                1385                1390

Leu Ile Gln Arg Leu Asn Lys Asn Ile Lys Pro Glu Thr Phe Thr Pro
        1395                1400                1405

Ala Leu Ile Ala Leu Lys Arg Asp Asn Asn Thr Asn Leu Ser Asn Tyr
    1410                1415                1420

Ser Asp Lys Ile Ile Met Ile Lys Pro Lys Tyr Leu Val Glu Arg Ser
1425                1430                1435                1440

Ile Gly Val Pro Trp Ser Thr Gly Leu Asp Gly Tyr Ile Gly Ser Glu
                1445                1450                1455

Gln Leu Lys Gly Gly Thr Ser Ser Asn Gly Gln Lys Arg Phe Lys Gln
            1460                1465                1470

Asp Phe Ile Gln Ala Leu Gly Leu Lys Asn Thr Glu Tyr His Gly Lys
        1475                1480                1485

Leu Gly Leu Ser Ile Arg Ile Phe Asp Pro Gly Asn Glu Leu Ala Lys
    1490                1495                1500

Ile Lys Asp Ala Ser Asn Lys Lys Gly Glu Glu Lys Leu Leu Lys Ser
1505                1510                1515                1520

Tyr Asp Leu Phe Lys Asn Tyr Leu Asn Glu Tyr Glu Lys Lys Ser Pro
                1525                1530                1535

Lys Ile Ala Lys Gly Trp Thr Asn Ile His Pro Asp Gln Lys Glu Tyr
            1540                1545                1550

Pro Asn Pro Asn Gln Lys Leu Pro Glu Asn Tyr Leu Asn Leu Val Leu
        1555                1560                1565

Asn Gln Pro Trp Lys Val Thr Leu Tyr Asn Ser Ser Asp Phe Ile Thr
    1570                1575                1580

Asn Leu Phe Val Glu Pro Glu Gly Ser Asp Arg Gly Ser Gly Ala Lys
1585                1590                1595                1600

Leu Lys Gln Val Ile Gln Lys Gln Val Asn Asn Asn Tyr Ala Asp Trp
                1605                1610                1615

Gly Ser Ala Tyr Leu Thr Phe Trp Tyr Asp Lys Asp Ile Ile Thr Asn
            1620                1625                1630

Gln Pro Asn Val Ile Thr Ala Asn Ile Ala Asp Val Phe Ile Lys Asp
        1635                1640                1645

Val Lys Glu Leu Glu Asp Asn Thr Lys Leu Ile Ala Pro Asn Ile Thr
    1650                1655                1660

Gln Trp Trp Pro Asn Ile Ser Gly Ser Lys Glu Lys Phe Tyr Lys Pro
1665                1670                1675                1680

Thr Val Phe Phe Gly Asn Trp Glu Asn Glu Asn Ser Asn Met Asn Ser
                1685                1690                1695

Gln Gly Gln Thr Pro Thr Trp Glu Lys Ile Arg Glu Gly Phe Ala Leu
            1700                1705                1710
```

-continued

```
Gln Ala Leu Lys Ser Ser Phe Asp Gln Lys Thr Arg Thr Phe Val Leu
        1715                1720                1725

Thr Thr Asn Ala Pro Leu Pro Leu Trp Lys Tyr Gly Pro Leu Gly Phe
    1730                1735                1740

Gln Asn Gly Pro Asn Phe Lys Thr Gln Asp Trp Arg Leu Val Phe Gln
1745                1750                1755                1760

Asn Asp Asp Asn Gln Ile Ala Ala Leu Arg Val Gln Glu Gln Asp Arg
                1765                1770                1775

Pro Glu Lys Ser Ser Glu Asp Lys Asp Lys Gln Lys Trp Ile Lys Phe
            1780                1785                1790

Lys Val Val Ile Pro Glu Glu Met Phe Asn Ser Gly Asn Ile Arg Phe
        1795                1800                1805

Val Gly Val Met Gln Ile Gln Gly Pro Asn Thr Leu Trp Leu Pro Val
    1810                1815                1820

Ile Asn Ser Ser Val Ile Tyr Asp Phe Tyr Arg Gly Thr Gly Asp Ser
1825                1830                1835                1840

Asn Asp Val Ala Asn Leu Asn Val Ala Pro Trp Gln Val Lys Thr Ile
                1845                1850                1855

Ala Phe Thr Asn Asn Ala Phe Asn Asn Val Phe Lys Glu Phe Asn Ile
            1860                1865                1870

Ser Lys Lys Ile Val Glu
        1875
```

<210> SEQ ID NO 21
<211> LENGTH: 45
<212> TYPE: DNA
<213> ORGANISM: Artificial Sequence
<220> FEATURE:
<223> OTHER INFORMATION: Oligonucleotide

<400> SEQUENCE: 21
gataatttta aaaaatggtc ggcaaaaaca gttttaactg ctgcc 45

<210> SEQ ID NO 22
<211> LENGTH: 45
<212> TYPE: DNA
<213> ORGANISM: Artificial Sequence
<220> FEATURE:
<223> OTHER INFORMATION: Oligonucleotide

<400> SEQUENCE: 22
ggcagcagtt aaaactgttt ttgccgacca tttttttaaaa ttatc 45

<210> SEQ ID NO 23
<211> LENGTH: 38
<212> TYPE: DNA
<213> ORGANISM: Artificial Sequence
<220> FEATURE:
<223> OTHER INFORMATION: Oligonucleotide

<400> SEQUENCE: 23
gaaagaggaa gtaattggtt ttcacgactt gaaagagc 38

<210> SEQ ID NO 24
<211> LENGTH: 38
<212> TYPE: DNA
<213> ORGANISM: Artificial Sequence
<220> FEATURE:
<223> OTHER INFORMATION: Oligonucleotide

<400> SEQUENCE: 24

-continued

```
gctctttcaa gtcgtgaaaa ccaattactt cctctttc                             38


<210> SEQ ID NO 25
<211> LENGTH: 41
<212> TYPE: DNA
<213> ORGANISM: Artificial Sequence
<220> FEATURE:
<223> OTHER INFORMATION: Oligonucleotide

<400> SEQUENCE: 25

ctaaaattct aaaatcctgg cttgaaacaa atcttcaagg c                         41


<210> SEQ ID NO 26
<211> LENGTH: 41
<212> TYPE: DNA
<213> ORGANISM: Artificial Sequence
<220> FEATURE:
<223> OTHER INFORMATION: Oligonucleotide

<400> SEQUENCE: 26

gccttgaaga tttgtttcaa gccaggattt tagaatttta g                         41


<210> SEQ ID NO 27
<211> LENGTH: 34
<212> TYPE: DNA
<213> ORGANISM: Artificial Sequence
<220> FEATURE:
<223> OTHER INFORMATION: Oligonucleotide

<400> SEQUENCE: 27

gcctctctga ttattggtat ggatctccga attc                                 34


<210> SEQ ID NO 28
<211> LENGTH: 34
<212> TYPE: DNA
<213> ORGANISM: Artificial Sequence
<220> FEATURE:
<223> OTHER INFORMATION: Oligonucleotide

<400> SEQUENCE: 28

gaattcggag atccatacca ataatcagag aggc                                 34


<210> SEQ ID NO 29
<211> LENGTH: 31
<212> TYPE: DNA
<213> ORGANISM: Artificial Sequence
<220> FEATURE:
<223> OTHER INFORMATION: Oligonucleotide

<400> SEQUENCE: 29

gggacaagca tttggacagc ttttaatttc g                                    31


<210> SEQ ID NO 30
<211> LENGTH: 31
<212> TYPE: DNA
<213> ORGANISM: Artificial Sequence
<220> FEATURE:
<223> OTHER INFORMATION: Oligonucleotide

<400> SEQUENCE: 30

cgaaattaaa agctgtccaa atgcttgtcc c                                    31


<210> SEQ ID NO 31
<211> LENGTH: 18
<212> TYPE: DNA
<213> ORGANISM: Artificial Sequence
```

-continued

<220> FEATURE:
<223> OTHER INFORMATION: Oligonucleotide

<400> SEQUENCE: 31
tccgacgatg acgataag 18

<210> SEQ ID NO 32
<211> LENGTH: 18
<212> TYPE: DNA
<213> ORGANISM: Artificial Sequence
<220> FEATURE:
<223> OTHER INFORMATION: Oligonucleotide

<400> SEQUENCE: 32
tggaaaatta gttcttgg 18

<210> SEQ ID NO 33
<211> LENGTH: 18
<212> TYPE: DNA
<213> ORGANISM: Artificial Sequence
<220> FEATURE:
<223> OTHER INFORMATION: Oligonucleotide

<400> SEQUENCE: 33
agtttccact tcatcgcc 18

<210> SEQ ID NO 34
<211> LENGTH: 15
<212> TYPE: PRT
<213> ORGANISM: Artificial Sequence
<220> FEATURE:
<223> OTHER INFORMATION: Tryptic peptide fragment

<400> SEQUENCE: 34

Glu Leu Glu Asp Asn Thr Lys Leu Ile Ala Pro Asn Ile Arg Gln
1 5 10 15

<210> SEQ ID NO 35
<211> LENGTH: 36
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 4, 6, 18, 30
<223> OTHER INFORMATION: N=Inosine

<400> SEQUENCE: 35
gaantngaag ataatacnaa attaattgcn cctaat 36

<210> SEQ ID NO 36
<211> LENGTH: 12
<212> TYPE: PRT
<213> ORGANISM: Artificial Sequence
<220> FEATURE:
<223> OTHER INFORMATION: N-terminal peptide

<400> SEQUENCE: 36

Asp Phe Leu Thr Asn Asn Gly Arg Thr Val Leu Glu
1 5 10

<210> SEQ ID NO 37
<211> LENGTH: 32
<212> TYPE: DNA
<213> ORGANISM: Artificial Sequence
<220> FEATURE:

-continued

<223> OTHER INFORMATION: Oligonucleotide

<400> SEQUENCE: 37
gaacaatttg atcacaagat cctgaatata cc 32

<210> SEQ ID NO 38
<211> LENGTH: 35
<212> TYPE: DNA
<213> ORGANISM: Artificial Sequence
<220> FEATURE:
<223> OTHER INFORMATION: Oligonucleotide

<400> SEQUENCE: 38
aattcctctg atcattattt agattttaat tcctg 35

<210> SEQ ID NO 39
<211> LENGTH: 9
<212> TYPE: PRT
<213> ORGANISM: Artificial Sequence
<220> FEATURE:
<223> OTHER INFORMATION: Antigen

<400> SEQUENCE: 39

Thr Ser Ser Gln Lys Asp Pro Ser Thr
1 5

<210> SEQ ID NO 40
<211> LENGTH: 12
<212> TYPE: PRT
<213> ORGANISM: Artificial Sequence
<220> FEATURE:
<223> OTHER INFORMATION: Antigen

<400> SEQUENCE: 40

Val Asn Gln Asn Phe Lys Val Lys Phe Gln Ala Leu
1 5 10

<210> SEQ ID NO 41
<211> LENGTH: 7
<212> TYPE: PRT
<213> ORGANISM: Artificial Sequence
<220> FEATURE:
<223> OTHER INFORMATION: N-terminal peptide

<400> SEQUENCE: 41

Ala Asp Glu Lys Thr Ser Ser
1 5

<210> SEQ ID NO 42
<211> LENGTH: 7
<212> TYPE: PRT
<213> ORGANISM: Artificial Sequence
<220> FEATURE:
<223> OTHER INFORMATION: N-terminal peptide

<400> SEQUENCE: 42

Ser Lys Lys Ser Lys Thr Phe
1 5